(12) United States Patent
Retter et al.

(10) Patent No.: US 6,656,480 B2
(45) Date of Patent: Dec. 2, 2003

(54) COMPOSITIONS AND METHODS FOR THE TREATMENT AND DIAGNOSIS OF BREAST CANCER

(75) Inventors: Marc W. Retter, Carnation, WA (US); Davin C. Dillon, Redmond, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/429,755

(22) Filed: Oct. 28, 1999

(65) Prior Publication Data

US 2002/0111467 A1 Aug. 15, 2002

Related U.S. Application Data

(63) Continuation-in-part of application No. 09/289,198, filed on Apr. 9, 1999, which is a continuation-in-part of application No. 09/062,451, filed on Apr. 17, 1998, now Pat. No. 6,344,550, which is a continuation-in-part of application No. 08/991,789, filed on Dec. 11, 1997, now Pat. No. 6,225,054, which is a continuation-in-part of application No. 08/838,762, filed as application No. PCT/US97/00485 on Jan. 10, 1997, now abandoned, and a continuation-in-part of application No. 08/700,014, filed on Aug. 20, 1996, now abandoned, which is a continuation-in-part of application No. 08/585,392, filed on Jan. 11, 1996, now abandoned.

(51) Int. Cl.[7] .................... A61K 39/00; C07K 14/00

(52) U.S. Cl. .................... 424/277.1; 424/184.1; 424/185.1; 530/300; 530/350; 530/806; 530/828; 435/69.1; 436/64; 436/813; 514/2; 536/23.1

(58) Field of Search ............... 530/300, 350, 530/806, 828; 536/23.1; 424/184.1, 185.1, 277.1; 514/2–12; 435/69.1; 436/64, 813

(56) References Cited

U.S. PATENT DOCUMENTS

| | | | |
|---|---|---|---|
| 5,231,012 A | 7/1993 | Mosmann et al. | 435/69.52 |
| 5,428,145 A | 6/1995 | Okamoto et al. | 536/23.72 |
| 5,516,650 A | 5/1996 | Foster et al. | 435/68.1 |
| 5,523,225 A | 6/1996 | Kraus | 435/240.1 |
| 5,585,270 A | 12/1996 | Grotendorst et al. | 435/252.3 |
| 5,811,535 A | 9/1998 | Adamou et al. | 536/23.5 |
| 5,872,237 A | 2/1999 | Feder et al. | 536/23.5 |
| 5,912,143 A | 6/1999 | Bandman et al. | 435/69.1 |
| 6,225,054 B1 | 5/2001 | Frudakis et al. | 435/6 |
| 6,329,505 B1 | 12/2001 | Xu et al. | 530/350 |
| 6,344,550 B1 | 2/2002 | Frudakis et al. | 536/23.5 |
| 2002/0009738 A1 * | 1/2002 | Houghton et al. | 435/6 |
| 2002/0022248 A1 * | 2/2002 | Xu et al. | 435/69.1 |
| 2002/0051977 A1 * | 5/2002 | Xu et al. | 435/6 |
| 2002/0068285 A1 * | 6/2002 | Frudakis et al. | 435/6 |
| 2002/0165371 A1 * | 11/2002 | Frudakis et al. | 536/23.1 |
| 2002/0183251 A1 * | 12/2002 | Xu et al. | 514/12 |
| 2002/0192763 A1 * | 12/2002 | Xu et al. | 435/69.7 |
| 2002/0193296 A1 * | 12/2002 | Xu et al. | 514/12 |
| 2003/0088062 A1 * | 5/2003 | Xu et al. | 530/350 |

FOREIGN PATENT DOCUMENTS

| | | |
|---|---|---|
| CA | 2044940 A1 | 12/1992 |
| EP | 0475623 A1 | 3/1992 |
| EP | 1033401 A2 | 9/2000 |
| GB | 2273099 A | 6/1994 |
| WO | WO 91/02062 | 2/1991 |
| WO | WO 92/10573 | 6/1992 |
| WO | WO 92/15680 | 9/1992 |
| WO | WO 94/11514 | 5/1994 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 97/25426 | 7/1997 |
| WO | WO 97/25431 | 7/1997 |
| WO | WO 98/45328 | 10/1998 |
| WO | WO 99/06550 * | 2/1999 |
| WO | WO 99/31236 | 6/1999 |
| WO | WO 00/61753 | 10/2000 |
| WO | WO 01/25272 | 4/2001 |
| WO | WO 01/51628 | 7/2001 |

OTHER PUBLICATIONS

Wei et al. Protection against mammary tumor growth by vaccination with full–length, modoified human Erb—2 DNA. International Journal of Cancer, vol. 81, pp. 748–754, 1999.*

Geysen et al. Cognitive features of continuous antigenic determinants. J. of Molecular Recognition, vol. 1, pp. 32–40, 1988.*

Russell et al. Structural features can be unconserved in proteins with similar folds. Journal of Molecular Biology, vol. 244, pp. 332–350, 1994.*

Adams et al., Genbank Accession No. Q60347, 1993.

Adams et al., Genbank Accession No. Q61250, 1993.

Anderson et al., "Sequence and organization of the human mitochondrial genome," *Nature* 290:457–465, 1981.

Bauer et al., "Identification of differentially expressed mRNA species by an improved display technique (DDRT–PCR)," *Nucleic Acids Research* 21(18):4272–4280, 1993.

(List continued on next page.)

*Primary Examiner*—Mary K. Zeman
(74) *Attorney, Agent, or Firm*—Seed IP Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

8 Claims, 19 Drawing Sheets

OTHER PUBLICATIONS

Bernard et al., "Cloning and Sequencing of Pro–α1(XI) Collagen cDNA Demonstrates That Type XI Belongs to the Fibrillar Class of Collagens and Reveals That the Expression of the Gene Is Not Restricted to Cartilagenous Tissue," *J. Biol. Chem.* 263(32):17159–17166, 1988.

Bratthauer et al., "Expression of LINE–1 Retrotransposons in Human Breast Cancer," *Cancer* 73:2333–2336, 1994.

Byrne et al., "A Screening Method to Identify Genes Commonly Overexpressed in Carcinomas and the Identification of a Novel Complementary DNA Sequence," *Cancer Research* 55:2869–2903, 1995.

Chai et al., Genbank Accession No. U03644, 1994.

Charnock–Jones et al., "Extension of incomplete cDNAs (ESTs) by biotin/streptavidin–mediated walking using polymerase chain reaction," *J. Biotechno.* 35:205–215, Jun. 1994.

Chen and Sager, "Differential Expression of Human Tissue Factor in Normal Mammary Epithelial Cells and in Carcinomas," *Molecular Medicine* 1(2):153–160, 1995.

Cordonnier et al., "Isolation of Novel Human Endogenous Retrovirus–Like Elements with Foamy Virus–Related pol Sequence," *Journal of Virology* 69(9):5890–5897, 1995.

Databank Genebank Accession No. Z34289, 1995.

Ezzell, "Cancer "Vaccines": An Idea Whose Time Has Come?," *The Journal of NIH Research* 7:46–49, 1995.

Frank et al., Genbank Accession No. Q70049, 1994.

Gura, "Systems for Identifying New Drugs Are Often Faulty," *Science* 278:1041–1042, 1997.

Haltmeier et al., "Identification of S71–Related Human Endogenous Retroviral Sequences with Full–Length pol Genes," *Virology* 209:550–560, 1995.

Hillier et al., Genbank Accession No. H80165, 1995.
Hillier et al., Genbank Accession No. R19532, 1995.
Hillier et al., Genbank Accession No. R55637, 1995.
Hillier et al., Genbank Accession No. R60426, 1995.
Hillier et al., Genbank Accession No. T83348, 1995.
Hillier et al., Genbank Accession No. R35308, 1995.

Keydar et al., "Properties of retrovirus–like particles produced by a human breast carcinoma cell line: Immunological relationship with mouse mammary tumor virus proteins," *Proc. Natl. Acad. Sci.* USA 81:4188–92, 1984.

Leib–Mösch and Seifarth, "Evolution and Biological Significance of Human Retroelements," *Virus Genes* 11(2/3):133–145, 1996.

Leib–Mösch et al., "Endogenous Retroviral Elements in Human DNA," *Cancer Research* 50:5636s–5642s, 1994.

Leib–Mösch et al., "Genomic Distribution and Transcription of Solitary HERV–K LTRs," *Genomics* 18:261–269, 1993.

Liang et al., "Differential Display of Eukaryotic Messenger RNA by Means of the Polymerase Chain Reaction," *Science* 257:967–971, 1992.

Matsubara et al., Genbank Accession No. T24124, 1995.

Wang et al., "Detection of Mammary Tumor Virus ENV Gene–like Sequences in Human Breast Cancer," *Cancer Research* 55:5173–5179, 1995.

Watson and Fleming, "Isolation of Differentially Expressed Sequence Tags from Human Breast Cancer," *Cancer Research* 54(17):4598–4602, 1994.

Werner et al., "S71 Is a Phylogenetically Distinct Human Endogenous Retroviral Element with Structural and Sequence Homology to Simian Sarcoma Virus (SSV)," *Virology* 174:225–238, 1990.

Yoshioka et al., "Pro–α1(XI) Collagen. Structure Of The Amino–Terminal Propeptide And Expression Of The Gene In Tumor Cell Lines," *J. Biol. Chem.* 265(11):6423–6426, 1990.

Critical Synergy: The Biotechnology Industry and Intellectual Property Protection, Presentation of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C., pp. 75, 100–107. 1994.

Ahmed et al., "Characterization of a retrovirus isolated form normal mink cells co–cultivated with a dog mammary tumour," *J. Gen. Virol.* 42:179–184, 1979.

Bakker et al., "Generation of antimelanoma cytotoxic T lymphocytes for healthy donors after presentation of melanoma–associated antigen–derived epitopes by dendritic cells in vivo," *Cancer Research* 55:5330–5334, Nov. 15, 1995.

Cease et al., "T cell clones specific for an amphipathic α–helical region of sperm whale myoglobin show differing fine specificities for synthetic peptides," *Journal of Experimental Medicine* 164:1779–1784, Nov. 1986.

Derks et al., "Synthesis of a viral protein with molecular weight of 30,000 (p30) by leukemic cells and antibodies cross–reacting with simian sarcoma virus p30 in serum of a chronic myeloid leukemia patient," *Cancer Research* 42:681–686, Feb. 1982.

Hehlmann et al., "Detection and biochemical characterization of antigens in human leukemic sera that cross–react with primate C–type viral proteins (M 30,000)[1]," *Cancer Research* 43:392–399, Jan. 1983.

Herbrink et al., "Detection of antibodies cross–reactive with type C RNA tumor viral p30 protein in human sera and exudate fluids," *Cancer Research* 40:166–173, Jan. 1980.

Hopp, T., "Computer prediction of protein surface features and antigenic determinants," *Molecular Basis of Cancer* Part B: Macromolecular Recognition, Chemotherapy, and Immunology:367–377, 1985.

Jerabek et al., "Detection and immunochemical characterization of a primate type C retrovirus–related p30 protein in normal human placentas," *Proc. Natl. Acad. Sci. USA* 81:6501–6505, Oct. 1984.

Kast et al., "Role of HLA–A motifs in identification of potential CTL epitopes in human papillmavirus type 16 E6 and E7 proteins," *J. Immunol.* 152:3904–3912, 1994.

Kawakami et al., "Recognition of multiple epitopes in the human melanoma antigen gp100 by tumor–infiltrating T lymphocytes associated with in vivo tumor regression," *J. Immunol.* 154:3961–3968, 1995.

Maeda et al., "Serum antibody reacting with placental syncytiotrophoblast in sera of patients with autoimmune diseases—a possible relation to type C RNA retroviruses," *Clin. Exp. Immunol.* 60:645–653, 1985.

Margalit et al., "Prediction of immunodominant helper T cell antigenic sites from the primary sequence," *The Journal of Immunology* 138(7):2213–2229, Apr. 1, 1987.

McCombs, R., "Role of oncornaviruses in carcinoma of the prostate," *Cancer Treatment Reports* 61(2):131–132, Mar./Apr. 1977.

Porter–Jordan and Lippman et al., "Overview of the biologic markers of breast cancer," *Breast Cancer* 8(1):73–100, Feb. 1994.

Rammensee et al., "MHC ligands and peptide motifs: first listing," *Immunogenetics* 41:178–228, 1995.

Rothbard and Taylor, "A sequence pattern common to T cell epitopes," *The EMBO Journal* 7(1):93–100, Jan. 1988.

Sette et al., "The relationship between class I binding affinity and immunogenicity of potential cytotoxic T cell epitopes," *J. Immunol.* 153:5586–5592, 1994.

Smith et al., "Expression of antigenic crossreactivity to RD114 p30 protein in a human fibrosarcoma cell line," *Proc. Natl. Acad. Sci. USA* 74(2):744–748, Feb. 1977.

Spouge et al., "Strong conformational propensities enhance T cell antigenicity," *The Journal of Immunology* 138(1):204–212, Jan. 1987.

Tsai et al., "In vitro immunization and expansion of antigen–specific cytotoxic T–lymphocytes for adoptive immunotherapy using peptide pulsed dendritic cells," *Critical Reviews in Immunology* 18:65–75, 1998.

Vaczi and Toth, "Studies on antigens of C–type primate viruses and antibodies to them at patients wit myeloid leukemia and potentially preleukemic hematological disorders," *Arch. Geschwulstforsch* 50(8):769–777, 1980.

Visseren et al., "CTL specific for the tyrosinase autoantigen can be induced form healthy donor blood to lyse melanoma cells," *J. Immunol* 154:3991–3998, 1995.

Vitiello et al., "Analysis of the HLA–restricted influenza specific cytotoxic T lymphcyte response in transgenic mice carrying a chimeric human–mouse class I major histocompatability complex," *J. Exp. Med.* 173:1007–1015, Apr. 1991.

Wiley and Cunningham, "A steady state model for analyzing the cellular binding, internalization and degradation of polypeptide ligands," *Cell* 25:433–440, Aug. 1981.

GenBank Accession No. Z34289, "*H. sapiens* mRNA for nucleolar phosphoprotein p130," Jun. 1, 1995.

Ahn and Kunkel, "The structural and functional diversity of dystrophin," *Nature Genetics* 3:283–291, Apr. 1993.

Attwood, T.K., "The Babel of Bioinformatices," *Science* 290:471–473, Oct. 20, 2000.

Boon, T., "Toward a Genetic Analysis of Tumor Rejection Antigens," *Adv. Cancer Res.* 58:177–210, 1982.

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue," *Journal of Cell Biology* 111:2129–2138, Nov. 1990.

Cawthon et al., "cDNA Sequence and Genomic Structure of *EV12B*, a Gene Lying with an Intron of the Neurofibromatosis Type 1 gene," *Genomics* 9: 446–460, 1991.

Curti, B.D., "Physical barriers to drug delivery in tumors," *Critical Reviews in Oncology/Hematology* 14:29–39, 1993.

Dermer, G.B., "Another Anniversary for the War on Cancer," *Bio/Technology* 12:320, Mar. 1994.

Drexler, H. "Recent Results on the Biology of Hodgkin and Reed–Sternberg cells. II. Continuous Cell Lines," *Leukemia and Lymphoma* 9: 1–25, 1993.

Embleton, M.J., "Monoclonal Antibodies to Osteogenic Sarcoma Antigens," in Monoclonal Antibodies and Cancer, *Immunology Series* 23, Wright, Jr. G.L. (ed.), Marcel Dekker, New York, NY, 1984, pp. 181–207.

Freshney, R.I., *Culture of Animal Cells: A Manual of Basic Technique*, Alan R. Liss, Inc., New York, 1983, pp. 3–4.

GenBank Accession No. AA533501, Aug. 1, 1997.
GenBank Accession No. AC018804, Feb. 11, 2003.
GenBank Accession No. AI804733, Jul. 6, 1999.
GenBank Accession No. AQ063365, Jul. 30, 1998.
GenBank Accession No. AQ124119, Aug. 31, 1998.
Geneseq (Derwent) Accession No. AAV68996, Jan. 22, 1999.
Genseq (Derwent) Accession No. AAL10921, Dec. 7, 2001.
Genseq (Derwent) Accession No. AAL11383, Dec. 7, 2001.
Genseq (Derwent) Accession No. AAL11455, Dec. 7, 2001.
Genseq (Derwent) Accession No. AAL13620, Dec. 7, 2001.
Genseq (Derwent) Accession No. AAL18685, Dec. 7, 2001.
Genseq (Derwent) Accession No. AAL20282, Dec. 7, 2001.
Genseq (Derwent) Accession No. AAL20354, Dec. 7, 2001.
Genseq (Derwent) Accession No. AAL22489. Dec. 7, 2001.

Gerhold and Caskey, "It's the genes! EST access to human genome content," *BioEssays* 18(12): 973–981, 1996.

Gillies and Wesolowski et al., "Antigen binding and biological activities of engineered mutant chimeric antibodies with human tumor specificities," *Hum. Antibod. Hybridomas* 1(1): 47–54, 1990.

Harris et al., "Polycystic Kidney Disease 1: Identification and Analysis of the Primary Defect," *Journal of the American Society of Nephrology* 6(4): 1125–1133, Oct. 1995.

Hartwell et al., "Integrating Genetic Approaches into the Discovery of Anticancer Drugs," *Science* 278: 1064–1068, Nov. 7, 1997.

Hsu, T.C., "Karyology of Cells in Culture," in Tissue Culture: Methods and Applications, Kurse, Jr et al. (eds.), Academic Press, New York, 1973, pp. 764–767.

Jain, R. K., "Barriers to Drug Delivery in Solid Tumors," *Scientific American* 271(1): 58–65, Jul. 1994.

Johnstone and Thorpe (eds.), *Immunochemistry in Practice*, Second Edition, Blackwell Scientific Publications, Oxford England, 1987, pp. 49–50.

Lazar et al., "Transforming Growth Factor α: Mutation of Aspartic Acid 47 and Leucine 48 Results in Different Biological Activities," *Molecular and Cellular Biology* 8: 1247–1252, Mar. 1988.

Tao and Morrison, "Studies of Aglycosylated Chimeric Mouse–Human IgG. Role of Carbohydrate in the Structure and Effector Functions Mediated by the Human IgG Constant Region," *Journal of Immunity* 143(8): 2595–2601, Oct. 15, 1989.

Venter et al., "Genome sequence analysis: scientific objectives and practical strategies," *Trends in Biotechnology* 10:8–11, Jan./Feb. 1992.

Walter, G., "Production of use of antibodies against synthetic peptides," *Journal of Immunological Methods* 88: 149–161, 1986.

Wells and Peitsch, "The chemokine information source: identification and characterization of novel chemokines using the WorldWideWeb and Expressed Sequence Tag Databases," *Journal of Leukocyte Biology* 61:545–550, May 1997.

* cited by examiner

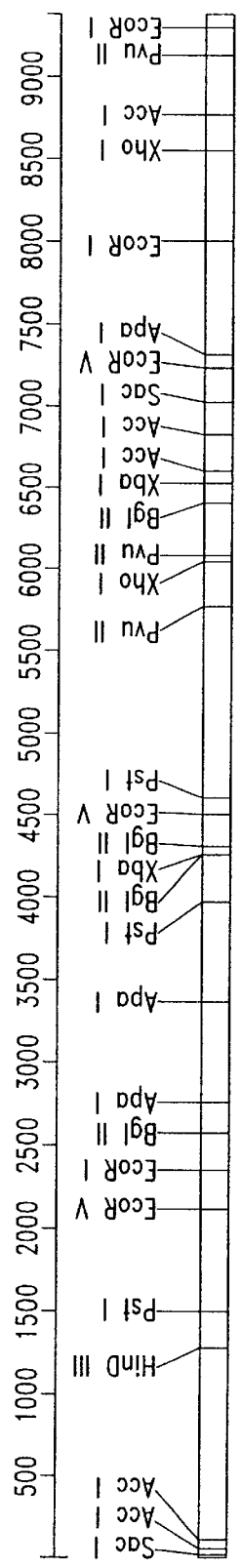
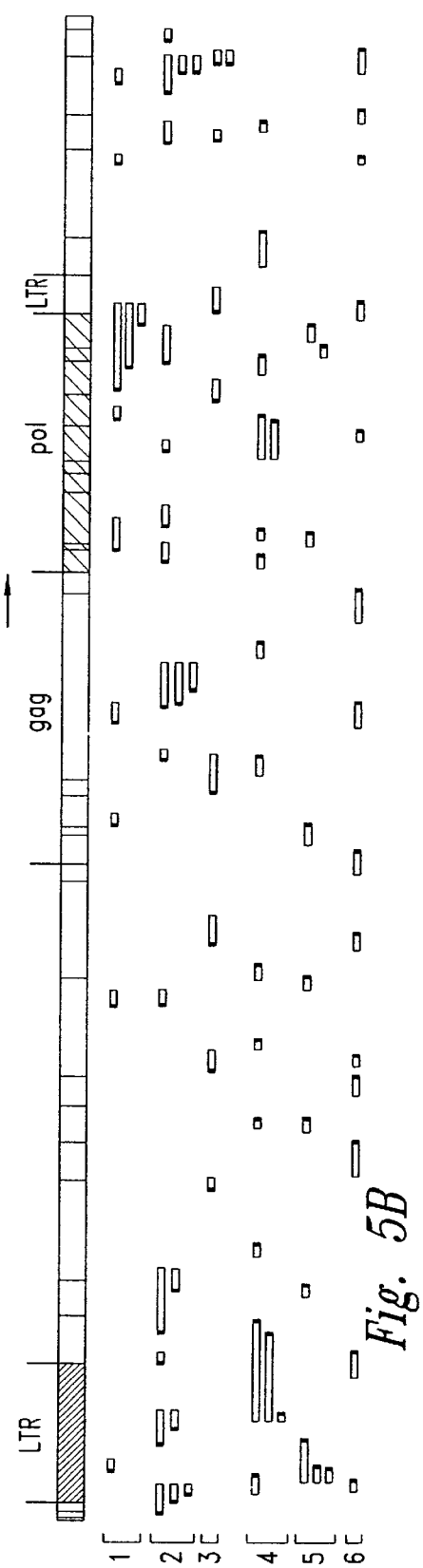
Fig. 5A
Fig. 5B

NUCLEOTIDE SEQUENCE OF THE REPRESENTATIVE BREAST-TUMOR SPECIFIC cDNA B18Ag1

```
TTA GAG ACC CAA TTG GGA CCT AAT TGG GAC CCA AAT TTC TCA AGT GGA    48
Leu Glu Thr Gln Leu Gly Pro Asn Trp Asp Pro Asn Phe Ser Ser Gly
 1           5                   10                  15

GGG AGA ACT TTT GAC GAT TTC CAC CGG TAT CTC CTC GTG GGT ATT CAG    96
Gly Arg Thr Phe Asp Asp Phe His Arg Tyr Leu Leu Val Gly Ile Gln
             20                  25                  30

GGA GCT GCC CAG AAA CCT ATA AAC TTG TCT AAG GCG ATT GAA GTC GTC   144
Gly Ala Ala Gln Lys Pro Ile Asn Leu Ser Lys Ala Ile Glu Val Val
         35                  40                  45

CAG GGG CAT GAT GAG TCA CCA GGA GTG TTT TTA GAG CAC CTC CAG GAG   192
Gln Gly His Asp Glu Ser Pro Gly Val Phe Leu Glu His Leu Gln Glu
     50                  55                  60

GCT TAT CGG ATT TAC ACC CCT TTT GAC CTG GCA GCC CCC GAA AAT AGC   240
Ala Tyr Arg Ile Tyr Thr Pro Phe Asp Leu Ala Ala Pro Glu Asn Ser
 65                  70                  75                  80

CAT GCT CTT AAT TTG GCA TTT GTG GCT CAG GCA GCC CCA GAT AGT AAA   288
His Ala Leu Asn Leu Ala Phe Val Ala Gln Ala Ala Pro Asp Ser Lys
             85                  90                  95

AGG AAA CTC CAA AAA CTA GAG GGA TTT TGC TGG AAT GAA TAC CAG TCA   336
Arg Lys Leu Gln Lys Leu Glu Gly Phe Cys Trp Asn Glu Tyr Gln Ser
         100                 105                 110

GCT TTT AGA GAT AGC CTA AAA GGT TTT                               363
Ala Phe Arg Asp Ser Leu Lys Gly Phe
         115                 120
```

Fig. 6

NUCLEOTIDE SEQUENCE OF THE REPRESENTATIVE BREAST-TUMOR SPECIFIC cDNA B17Ag1

```
GC TGGGCACAGT GGCTCATACC TGTAATCCTG ACCGTTTCAG AGGCTCAGGT      60

CG CTTGAGCCCA AGATTTCAAG ACTAGTCTGG GTAACATAGT GAGACCCTAT     120

AA AAATAAAAAA ATGAGCCTGG TGTAGTGGCA CACACCAGCT GAGGAGGGAG    180

CT AGGAGA                                                     196
```

Fig. 7

NUCLEOTIDE SEQUENCE OF THE REPRESENTATIVE
BREAST-TUMOR SPECIFIC cDNA B17Ag2

```
GC TTGGGGGCTC TGACTAGAAA TTCAAGGAAC CTGGGATTCA AGTCCAACTG   60

AC TTACACTGTG GNCTCCAATA AACTGCTTCT TTCCTATTCC CTCTCTATTA   120

AA GGAAAACGAT GTCTGTGTAT AGCCAAGTCA GNTATCCTAA AAGGAGATAC   180

AT TAAATATCAG AATGTAAAAC CTGGGAACCA GGTTCCCAGC CTGGGATTAA   240

CA AGAAGACTGA ACAGTACTAC TGTGAAAAGC CCGAAGNGGC AATATGTTCA   300

TT GAAGGATGGC TGGGAGAATG AATGCTCTGT CCCCCAGTCC CAAGCTCACT   360

CT CCTTTATAGC CTAGGAGA                                     388
```

*Fig. 8*

NUCLEOTIDE SEQUENCE OF THE REPRESENTATIVE
BREAST-TUMOR SPECIFIC cDNA B13Ag2a

```
GC CTATAATCAT GTTTCTCATT ATTTTCACAT TTTATTAACC AATTTCTGTT   60

AA AATATGAGGG AAATATATGA AACAGGGAGG CAATGTTCAG ATAATTGATC   120

TG ATTTCTACAT CAGATGCTCT TTCCTTTCCT GTTTATTTCC TTTTTATTTC   180

GG TCGAATGTAA TAGCTTTGTT TCAAGAGAGA GTTTTGGCAG TTTCTGTAGC   240

CT GCTCATGTCT CCAGGCATCT ATTTGCACTT TAGGAGGTGT CGTGGGAGAC   300

CT ATTTTTTCCA TATTTGGGCA ACTACTA                           337
```

*Fig. 9*

NUCLEOTIDE SEQUENCE OF THE REPRESENTATIVE BREAST-TUMOR SPECIFIC cDNA B13Ag1b

```
GC CATACAGTGC CTTTCCATTT ATTTAACCCC CACCTGAACG GCATAAACTG   60

GC TGGTGTTTTT TACTGTAAAC AATAAGGAGA CTTTGCTCTT CATTTAAACC  120

AT TTCATATTTT ACGCTCGAGG GTTTTACCG GTTCCTTTTT ACACTCCTTA  180

TT TAAGTCGTTT GGAACAAGAT ATTTTTTCTT TCCTGGCAGC TTTTAACATT  240

TT TGTGTCTGGG GGACTGCTGG TCACTGTTTC TCACAGTTGC AAATCAAGGC  300

CC AAGAAAAAAA AATTTTTTTG TTTTATTTGA AACTGGACCG GATAAACGGT  360

CG GCTGCTGTAT ATAGTTTTAA ATGGTTTATT GCACCTCCTT AAGTTGCACT  420

GG GGGGNTTTTG NATAGAAAGT NTTTANTCAC ANAGTCACAG GGACTTTTNT  480

NA CTGAGCTAAA AAGGGCTGNT TTTCGGGTGG GGGCAGATGA AGGCTCACAG  540

TC TCTTAGAGGG GGGAACTNCT A                                571
```

*Fig. 10*

NUCLEOTIDE SEQUENCE OF THE REPRESENTATIVE
BREAST-TUMOR SPECIFIC cDNA B13Ag1a

| | | | | |
|---|---|---|---|---|
| TA ATAACTTAAA | TATATTTTGA | TCACCCACTG | GGGTGATAAG | ACAATAGATA 60 |
| TT TCCAAAAAGC | ATAAAACCAA | AGTATCATAC | CAAACCAAAT | TCATACTGCT 120 |
| CC GCACTGAAAC | TTCACCTTCT | AACTGTCTAC | CTAACCAAAT | TCTACCCTTC 180 |
| GG TGCGTGCTCA | CTACTCTTTT | TTTTTTTTTT | TTTNTTTGG | AGATGGAGTC 240 |
| CA GCCCAGGGGT | GGAGTACAAT | GGCACAACCT | CAGCTCACTG | NAACCTCCGC 300 |
| TT CATGAGATTC | TCCTGNTTCA | GCCTTCCCAG | TAGCTGGGAC | TACAGGTGTG 360 |
| TG CCTGGNTAAT | CTTTTTTNGT | TTTNGGGTAG | AGATGGGGGT | TTTACATGTT 420 |
| TG GTNTCGAACT | CCTGACCTCA | AGTGATCCAC | CCACCTCAGG | CTCCCAAAGT 480 |
| TA CAGACATGAG | CCACTGNGCC | CAGNCCTGGT | GCATGCTCAC | TTCTCTAGGC 540 |

*Fig. 11*

NUCLEOTIDE SEQUENCE OF THE REPRESENTATIVE
BREAST-TUMOR SPECIFIC cDNA B11Ag1

| | |
|---|---|
| TG CACATGCAGA ATATTCTATC GGTACTTCAG CTATTACTCA TTTTGATGGC | 60 |
| AG CCTATCCTCA AGATGAGTAT TTAGAAAGAA TTGATTTAGC GATAGACCAA | 120 |
| GC ACTCTGACTA CACGAAATTG TTCAGATGTG ATGGATTTAT GACAGTTGAT | 180 |
| GA GATTATTAAG TGATTATTTT AAAGGGAATC CATTAATTCC AGAATATCTT | 240 |
| TC AAGATGATAT AGAAATAGAA CAGAAAGAGA CTACAAATGA AGATGTATCA | 300 |
| TA TTGAAGAGCC TATAGTAGAA AATGAATTAG CTGCATTTAT TAGCCTTACA | 360 |
| TT TTCCTGATGA ATCTTATATT CAGCCATCGA CATAGCATTA CCTGATGGGC | 420 |
| GA ATAATAGAAA CTGGGTGCGG GGCTATTGAT GAATTCATCC NCAGTAAATT | 480 |
| AC AAAATATAAC TCGATTGCAT TTGGATGATG GAATACTAAA TCTGGCAAAA | 540 |
| GG AGCTACTAGT AACCTCTCTT TTTGAGATGC AAAATTTTCT TTAGGGTTT | 600 |
| CT ACTTTACGGA TATTGGAGCA TAACGGGA | 638 |

*Fig. 12*

NUCLEOTIDE SEQUENCE OF THE REPRESENTATIVE
BREAST-TUMOR SPECIFIC cDNA B3CA3c

ACTGATGGAT GTCGCCGGAG GCGAGGGGCC TTATCTGATG CTCGGCTGCC TGTTCGTGAT  60

GTGCGCGGCG ATTGGGCTGT TTATCTCAAA CACCGCCACG GCGGTGCTGA TGGCGCCTAT  120

TGCCTTAGCG GCGGCGAAGT CAATGGGCGT CTCACCCTAT CCTTTTGCCA TGGTGGTGGC  180

GATGGCGGCT TCGGCGGCGT TTATGACCCC GGTCTCCTCG CCGGTTAACA CCCTGGTGCT  240

TGGCCCTGGC AAGTACTCAT TTAGCGATTT TGTCAAAATA GGCGTG  286

*Fig. 13*

NUCLEOTIDE SEQUENCE OF THE REPRESENTATIVE
BREAST-TUMOR SPECIFIC cDNA B9CG1

AG CAGCCCCTTC TTCTCAATTT CATCTGTCAC TACCCTGGTG TAGTATCTCA  60

CA TTTTTATAGC CTCCTCCCTG GTCTGTCTTT TGATTTTCCT GCCTGTAATC  120

AC ATAACTGCAA GTAAACATTT CTAAAGTGTG GTTATGCTCA TGTCACTCCT  180

AA ATAGTTTCCA TTACCGTCTT AATAAAATTC GGATTTGTTC TTTNCTATTN  240

CA CCTATGACCG AA  262

*Fig. 14*

NUCLEOTIDE SEQUENCE OF THE REPRESENTATIVE
BREAST-TUMOR SPECIFIC cDNA B9CG3

```
AG CAAAGCCAGT GGTTTGAGCT CTCTACTGTG TAAACTCCTA AACCAAGGCC    60

TA AATGGTGGCA GGATTTTTAT TATAAACATG TACCCATGCA AATTTCCTAT   120

GA TATATTCTTC TACATTTAAA CAATAAAAAT AATCTATTTT TAAAAGCCTA   180

AG TTAGGTAAGA GTGTTTAATG AGAGGGTATA AGGTATAAAT CACCAGTCAA   240

TG CCTATGACCG A                                            261
```

Fig. 15

NUCLEOTIDE SEQUENCE OF THE REPRESENTATIVE
BREAST-TUMOR SPECIFIC cDNA B2CA2

```
GG GCATGGACGC AGACGCCTGA CGTTTGGCTG AAAATCTTTC ATTGATTCGT    60

AT AGGAAAATTC CCAAAGAGGG AATGTCCTGT TGCTCGCCAG TTTTTNTGTT   120

GG ANAAGGCAAN GAGCTCTTCA GACTATTGGN ATTNTCGTTC GGTCTTCTGC   180

CG NCTTGCNANG ATCTTCAT                                     208
```

Fig. 16

NUCLEOTIDE SEQUENCE OF THE REPRESENTATIVE
BREAST-TUMOR SPECIFIC cDNA B3CA1

| | |
|---|---|
| GG GCATGGACGC AGACGCCTGA CGTTTGGCTG AAAATCTTTC ATTGATTCGT | 60 |
| AT AGGAAAATTC CCAAAGAGGG AATGTCCTGT TGCTCGCCAG TTTTTNTGTT | 120 |
| GG ANAAGGCAAN GAGCTCTTCA GACTATTGGN ATTNTCGTTC GGTCTTCTGC | 180 |
| CG NCTTGCNANG ATCTTCAT | 208 |

*Fig. 17*

NUCLEOTIDE SEQUENCE OF THE REPRESENTATIVE
BREAST-TUMOR SPECIFIC cDNA B3CA2

| | |
|---|---|
| GG GCATGGACGC AGACGCCTGA CGTTTGGCTG AAAATCTTTC ATTGATTCGT | 60 |
| AT AGGAAAATTC CCAAAGAGGG AATGTCCTGT TGCTCGCCAG TTTTTNTGTT | 120 |
| GG ANAAGGCAAN GAGCTCTTCA GACTATTGGN ATTNTCGTTC GGTCTTCTGC | 180 |
| CG NCTTGCNANG ATCTTCAT | 208 |

*Fig. 18*

NUCLEOTIDE SEQUENCE OF THE REPRESENTATIVE
BREAST-TUMOR SPECIFIC cDNA B3CA3

| | |
|---|---|
| AG GGAGCAAGGA GAAGGCATGG AGAGGCTCAN GCTGGTCCTG GCCTACGACT | 60 |
| CT GTCGCCGGGG ATGGTGGAGA ACTGAAGCGG GACCTCCTCG AGGTCCTCCG | 120 |
| TC NCCGTCCAGG AGGAGGGTCT TTCCGTGGTC TNGGAGGAGC GGGGGGAGAA | 180 |
| TC ATGGTCNACA TCCC | 204 |

*Fig. 19*

NUCLEOTIDE SEQUENCE OF THE REPRESENTATIVE
BREAST-TUMOR SPECIFIC cDNA B4CA1

TC AGGAGCGGGT AGAGTGGCAC CATTGAGGGG ATATTCAAAA ATATTATTTT    60

TG ATAGTTGCTG AGTTTTTCTT TGACCCATGA GTTATATTGG AGTTTATTTT    120

CC AATCGCATGG ACATGTTAGA CTTATTTTCT GTTAATGATT NCTATTTTA    180

GA TTTGAGAAAT TGGTTNTTAT TATATCAATT TTTGGTATTT GTTGAGTTTG    240

GC TTAGTATGTG ACCA                                          264

Fig. 20

SEQUENCE LISTING

<160> NUMBER OF SEQ ID NOS: 315

<210> SEQ ID NO 1
<211> LENGTH: 363
<212> TYPE: DNA
<213> ORGANISM: Homo sapien

<400> SEQUENCE: 1

```
ttagagaccc aattgggacc taattgggac ccaaatttct caagtggagg gagaactttt      60
gacgatttcc accggtatct cctcgtgggt attcagggag ctgcccagaa acctataaac     120
ttgtctaagg cgattgaagt cgtccagggg catgatgagt caccaggagt gtttttagag     180
cacctccagg aggcttatcg gatttacacc ccttttgacc tggcagcccc cgaaaatagc     240
catgctctta atttggcatt tgtggctcag gcagcccag atagtaaaag gaaactccaa     300
aaactagagg gattttgctg gaatgaatac cagtcagctt ttagagatag cctaaaaggt     360
ttt                                                                    363
```

<210> SEQ ID NO 2
<211> LENGTH: 121
<212> TYPE: PRT
<213> ORGANISM: Homo sapien

<400> SEQUENCE: 2

```
Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
                20                  25                  30

Gly Ala Ala Gln Lys Pro Ile Asn Leu Ser Lys Ala Ile Glu Val Val
            35                  40                  45

Gln Gly His Asp Glu Ser Pro Gly Val Phe Leu Glu His Leu Gln Glu
        50                  55                  60

Ala Tyr Arg Ile Tyr Thr Pro Phe Asp Leu Ala Ala Pro Glu Asn Ser
65                  70                  75                  80

His Ala Leu Asn Leu Ala Phe Val Ala Gln Ala Ala Pro Asp Ser Lys
                85                  90                  95

Arg Lys Leu Gln Lys Leu Glu Gly Phe Cys Trp Asn Glu Tyr Gln Ser
                100                 105                 110
```

Ala Phe Arg Asp Ser Leu Lys Gly Phe
     115                 120

<210> SEQ ID NO 3
<211> LENGTH: 1080
<212> TYPE: DNA
<213> ORGANISM: Homo sapien
<220> FEATURE:
<221> NAME/KEY: misc_feature
<222> LOCATION: (1)...(1080)
<223> OTHER INFORMATION: n = A,T,C or G

<400> SEQUENCE: 3

| | | | | | |
|---|---|---|---|---|---|
| tcttagaatc | ttcatacccc | gaactcttgg | gaaaacttta | atcagtcacc | tacagtctac | 60 |
| cacccattta | ggaggagcaa | agctacctca | gctcctccgg | agccgtttta | agatccccca | 120 |
| tcttcaaagc | ctaacagatc | aagcagctct | ccggtgcaca | acctgcgccc | aggtaaatgc | 180 |
| caaaaaggt | cctaaaccca | gcccaggcca | ccgtctccaa | gaaaactcac | caggagaaaa | 240 |
| gtgggaaatt | gactttacag | aagtaaaacc | acaccgggct | gggtacaaat | accttctagt | 300 |
| actggtagac | accttctctg | gatggactga | agcatttgct | accaaaaacg | aaactgtcaa | 360 |
| tatggtagtt | aagttttttac | tcaatgaaat | catccctcga | cgtgggctgc | ctgttgccat | 420 |
| agggtctgat | aatggaacgg | ccttcgcctt | gtctatagtt | taatcagtca | gtaaggcgtt | 480 |
| aaacattcaa | tggaagctcc | attgtgccta | tcgacccaga | gctctgggca | agtagaacgc | 540 |
| atgaactgca | ccctaaaaaa | acactcttac | aaaattaatc | ttaaaaaccg | gtgttaattg | 600 |
| tgttagtctc | cttcccttag | ccctacttag | agttaaggtg | cacccctttac | tgggctgggt | 660 |
| tctttacctt | ttgaaatcat | ntttnggaag | gggctgccta | tctttnctta | actaaaaaan | 720 |
| gcccatttgg | caaaaatttc | ncaactaatt | tntacgtncc | tacgtctccc | caacaggtan | 780 |
| aaaaatctnc | tgccctttc | aaggaaccat | cccatccatt | cctnaacaaa | aggcctgccn | 840 |
| ttcttccccc | agttaactnt | tttttnttaa | aattcccaaa | aaangaaccn | cctgctggaa | 900 |
| aaacncccc | ctccaancc | cggccnaagn | ggaaggttcc | cttgaatccc | nccccncna | 960 |
| anggcccgga | accnttaaan | tngttccngg | gggtnnggcc | taaaagnccn | atttggtaaa | 1020 |
| cctanaaatt | ttttctttttn | taaaaaccac | nntttnnttt | ttcttaaaca | aaaccctntt | 1080 |

<210> SEQ ID NO 4
<211> LENGTH: 1087
<212> TYPE: DNA
<213> ORGANISM: Homo sapien
<220> FEATURE:
<221> NAME/KEY: misc_feature
<222> LOCATION: (1)...(1087)
<223> OTHER INFORMATION: n = A,T,C or G

<400> SEQUENCE: 4

| | | | | | |
|---|---|---|---|---|---|
| tctagagctg | cgcctggatc | ccgccacagt | gaggagacct | gaagaccaga | gaaaacacag | 60 |
| caagtaggcc | ctttaaacta | ctcacctgtg | ttgtcttcta | atttattctg | ttttatttg | 120 |
| tttccatcat | tttaagggt | taaaatcatc | ttgttcagac | ctcagcatat | aaaatgaccc | 180 |
| atctgtagac | ctcaggctcc | aaccataccc | caagagttgt | ctggttttgt | ttaaattact | 240 |
| gccaggtttc | agctgcagat | atccctggaa | ggaatattcc | agattccctg | agtagtttcc | 300 |
| aggttaaaat | cctataggct | tcttctgttt | tgaggaagag | ttcctgtcag | agaaaaacat | 360 |
| gatttggat | ttttaactttt | aatgcttgtg | aaacgctata | aaaaaaattt | ctaccccta | 420 |
| gctttaaagt | actgttagtg | agaaattaaa | attccttcag | gaggattaaa | ctgccatttc | 480 |

```
agttaccta attccaaatg ttttggtggt tagaatcttc tttaatgttc ttgaagaagt      540
gttttatatt ttcccatcna gataaattct ctcncncctt nnttttntnt ctnnttttttt    600 aaaacggant cttgctccgt tgtccangct gggaattttt ttttggccaa tctccgctnc     660
cttgcaanaa tnctgcntcc caaaattacc nccttttttcc cacctccacc ccnnggaatt    720
acctggaatt anaggccccc nccccccccc cggctaattt gttttttgttt ttagtaaaaa    780 acgggtttcc tgttttagtt aggatggccc anntctgacc ccntnatcnt ccccctcngc    840
cctcnaatnt tnggnntang gcttacccc cccngnngtt tttcctccat tnaaattttc     900
tntggantct tgaatnncgg gttttccctt ttaaaccnat tttttttttn nnnccccccan   960 ttttncctcc cccntntnta anggggttt cccaanccgg gtccnccccc angtccccaa    1020
tttttctccc ccccctctt ttttctttnc cccaaaantc ctatcttttc ctnnaaatat    1080 cnantnt                                                              1087

<210> SEQ ID NO 5
<211> LENGTH: 1010
<212> TYPE: DNA
<213> ORGANISM: Homo sapien
<220> FEATURE:
<221> NAME/KEY: misc_feature
<222> LOCATION: (1)...(1010)
<223> OTHER INFORMATION: n = A,T,C or G

<400> SEQUENCE: 5
tctagaccaa gaaatgggag gattttagag tgactgatga tttctctatc atctgcagtt     60
agtaaacatt ctccacagtt tatgcaaaaa gtaacaaaac cactgcagat gacaaacact    120
aggtaacaca catactatct cccaaatacc tacccacaag ctcaacaatt ttaaactgtt    180
aggatcactg gctctaatca ccatgacatg aggtcaccac caaaccatca agcgctaaac    240
agacagaatg tttccactcc tgatccactg tgtgggaaga agcaccgaac ttacccactg    300 ggggcctgc ntcanaanaa aagcccatgc ccccgggtnt nccttnaac cggaacgaat      360 naacccacca tccccacanc tcctctgttc ntgggccctg catcttgtgg cctcntntnc    420
tttnggggan acntggggaa ggtaccccat ttcnttgacc ccncnanaaa accccngtgg    480
ccctttgccc tgattcncnt gggccttttc tcttttccct tttggttgt ttaaattccc    540 aatgtccccn gaaccctctc cntnctgccc aaaacctacc taaattnctc nctangnntt   600
ttcttggtgt tncttttcaa aggtnacctt ncctgttcan ncccacnaa aatttnttcc    660 ntatnntggn cccnnaaaaa nnnatcnncc cnaattgccc gaattggttn ggtttttcct    720
nctgggggaa acccttttaaa tttccccctt ggccggcccc ccttttttcc ccccttttnga  780 aggcaggngg ttcttcccga acttccaatt ncaacagccn tgcccattgn tgaaaccctt    840
ttcctaaaat taaaaaatan ccggttnngg nnggcctctt tcccctccng gngggnngng    900
aaantcctta ccccnaaaaa ggttgcttag ccccngtcc ccactccccc nggaaaatn     960 aaccttttcn aaaaaggaa tataantttn ccactccttn gttctcttcc                1010

<210> SEQ ID NO 6
<211> LENGTH: 950
<212> TYPE: DNA
<213> ORGANISM: Homo sapien
<220> FEATURE:
<221> NAME/KEY: misc_feature
<222> LOCATION: (1)...(950)
<223> OTHER INFORMATION: n = A,T,C or G
```

<400> SEQUENCE: 6

```
tctagagctc gcggccgcga gctctaatac gactcactat agggcgtcga ctcgatctca      60
gctcactgca atctctgccc ccggggtcat gcgattctcc tgcctcagcc ttccaagtag     120
ctgggattac aggcgtgcaa caccacaccc ggctaatttt gtattttta tagagatggg      180
gttttccctt gttggccann atggtctcna acccctgacc tcnngtgatc ccccncccn      240
nganctcnna ctgctgggga tnccgnnnn nnncctcccn ncncnnnnnn ncncnntccn      300
tnntccttnc tcnnnnnnn cnntcnntcc nncttctcnc cnnntnttnt cnncnnccnn      360
cnnnccncnt nccncnnnt tcncntncnn tntccnncnn nntcnncnnn cnnnncntnn      420
ccnntacntc ntnnncnnnt cctctntnn cctcnncnnt cnctncncnt tntctcctcn      480
ntnnnnnnct ccnnnnntct cntcncnncn tncctcnntn nccncncccc ncctcncnnc      540
ctnntttnnn cnncnnntcc ntnccnttcn nntccnntnn cnncntcncn nncnttnttc      600
ccncnntttc cttncncntn nnntntcnnn cncntcnntc ntttnctcct nnntcccnnc      660
tcnnttcncc cnnntccncc cccncctnt ctctcnccn nntnnntntn nnncntccnc       720
tntcncnttc ntcnntncnt tnctntcnnc nncnntncnc tnccntntnt ctnnntcncn      780
tcncntntcn ccntccnttn ctntctcctn tntccttccc ctcncctnct cnttcnccnc      840
ccnntntntn tnncnccnnt nctnnncnnc cntcntttcn tctctnctnn nnntnncctc      900
nnccntncc ctnntncnct nctnntaccn tnctnctccn tcttccttcc                  950
```

<210> SEQ ID NO 7
<211> LENGTH: 1086
<212> TYPE: DNA
<213> ORGANISM: Homo sapien
<220> FEATURE:
<221> NAME/KEY: misc_feature
<222> LOCATION: (1)...(1086)
<223> OTHER INFORMATION: n = A,T,C or G

<400> SEQUENCE: 7

```
tctagagctc gcggccgcga gctcaattaa ccctcactaa agggagtcga ctcgatcaga      60
ctgttactgt gtctatgtag aaagaagtag acataagaga ttccattttg ttctgtacta     120
agaaaaattc ttctgccttg agatgctgtt aatctgtaac cctagcccca accctgtgct     180
cacagagaca tgtgctgtgt tgactcaagg ttcaatggat ttagggctat gctttgttaa     240
aaaagtgctt gaagataata tgcttgttaa aagtcatcac cattctctaa tctcaagtac     300
ccagggacac aatacactgc ggaaggccgc agggacctct gtctaggaaa gccaggtatt     360
gtccaagatt tctccccatg tgatagcctg agatatggcc tcatgggaag ggtaagacct     420
gactgtcccc cagcccgaca tcccccagcc cgacatcccc cagcccgaca cccgaaaagg     480
gtctgtgctg aggaagatta ntaaaagagg aaggctcttt gcattgaagt aagaagaagg     540
ctctgtctcc tgctcgtccc tgggcaataa aatgtcttgg tgttaaaccc gaatgtatgt     600
tctacttact gagaatagga gaaacatccc ttagggctgg aggtgagaca ccctggcggc     660
atactgctct ttaatgcacg agatgtttgt ntaattgcca tccagggcca nccccttccc    720
ttaactttt atganacaaa aactttgttc ncttttcctg cgaacctctc ccctattan       780
cctattggcc tgcccatccc ctccccaaan ggtgaaaana tgttcntaaa tncgagggaa     840
tccaaaacnt tttcccgttg gtcccctttc caacccgtc cctgggccnn tttcctcccc      900
aacntgtccc ggntccttcn ttcccnccc cttcccngan aaaaacccc gtntganggn       960
gccccctcaa attataacct ttccnaaaca aannggttcn aaggtggttt gnttccggtg    1020
```

```
cggctggcct tgaggtcccc cctncacccc aatttggaan ccngttttt ttattgcccn     1080 ntcccc                                                                1086
```

<210> SEQ ID NO 8
<211> LENGTH: 1177
<212> TYPE: DNA
<213> ORGANISM: Homo sapien
<220> FEATURE:
<221> NAME/KEY: misc_feature
<222> LOCATION: (1)...(1177)
<223> OTHER INFORMATION: n = A,T,C or G

<400> SEQUENCE: 8

```
nccntttaga tgttgacaan ntaaacaagc ngctcaggca gctgaaaaaa gccactgata      60
aagcatcctg gagtatcaga gtttactgtt agatcagcct catttgactt cccctcccac    120
atggtgttta aatccagcta cactacttcc tgactcaaac tccactattc ctgttcatga    180
ctgtcaggaa ctgttggaaa ctactgaaac tggccgacct gatcttcaaa atgtgcccct    240
aggaaaggtg gatgccaccg tgttcacaga cagtaccncc ttcctcgaga agggactacg    300
aggggccggt gcanctgtta ccaaggagac tnatgtgttg tgggctcagg ctttaccanc    360
aaacacctca ncncnnaagg ctgaattgat cgccctcact caggctctcg gatggggtaa    420
gggatattaa cgttaacact gacagcaggt acgcctttgc tactgtgcat gtacgtggag    480
ccatctacca ggagcgtggg ctactcactc ggcaggtggc tgtnatccac tgtaaaggga    540
catcaaaagg aaaacnnggc tgttgcccgt ggtaaccana aanctgatcn ncagctcnaa    600
gatgctgtgt tgactttcac tcncncctct taaacttgct gcccacantc tcctttccca    660
accagatctg cctgacaatc cccatactca aaaaaaaaan aanactggcc ccgaacccna    720
accaataaaa acggggangg tnggtngnac nncctgaccc aaaaataatg gatccccgg     780 gctgcaggaa ttcaattcan ccttatcnat accccccaacn ngngggggg ggccngtncc    840 cattnccct ntattnattc tttnnccccc ccccggcnt cctttttnaa ctcgtgaaag      900
ggaaaacctg ncttaccaan ttatcncctg gaccntcccc ttccncggtn gnttanaaaa    960
aaaagcccnc antcccntcc naaatttgca cngaaaggna aggaatttaa cctttatttt   1020
ttnntccttt antttgtnnn cccccttta cccaggcgaa cngccatcnt ttaanaaaaa    1080
aaanagaang tttattttc cttngaacca tcccaatana aancacccgc ngggaacgg     1140 ggnggnaggc cnctcacccc ctttntgtng gnggnc                              1177
```

<210> SEQ ID NO 9
<211> LENGTH: 1146
<212> TYPE: DNA
<213> ORGANISM: Homo sapien
<220> FEATURE:
<221> NAME/KEY: misc_feature
<222> LOCATION: (1)...(1146)
<223> OTHER INFORMATION: n = A,T,C or G

<400> SEQUENCE: 9

```
nccnnttnnt gatgttgtct ttttggcctc tctttggata ctttccctct cttcagaggt      60 gaaagggtc aaaggagct gttgacagtc atcccaggtg ggccaatgtg tccagagtac      120
agactccatc agtgaggtca aagcctgggg cttttcagag aagggaggat tatgggtttt    180
ccaattatac aagtcagaag tagaaagaag ggacataaac caggaagggg gtggagcact    240
catcacccag agggacttgt gcctctctca gtggtagtag aggggctact tcctcccacc    300
```

-continued

```
acggttgcaa ccaagaggca atgggtgatg agcctacagg ggacatancc gaggagacat      360
gggatgaccc taagggagta ggctggtttt aaggcggtgg gactgggtga gggaaactct      420
cctcttcttc agagagaagc agtacagggc gagctgaacc ggctgaaggt cgaggcgaaa      480
acacggtctg gctcaggaag accttggaag taaaattatg aatggtgcat gaatggagcc      540
atggaagggg tgctcctgac caaactcagc cattgatcaa tgttaggaa actgatcagg       600 gaagccggga atttcattaa caacccgcca cacagcttga acattgtgag gttcagtgac      660
ccttcaaggg gccactccac tccaactttg gccattctac tttgcnaaat tccaaaact      720 tccttttta aggccgaatc cntantccct naaaaacnaa aaaaaatctg cnnctattct       780
ggaaaaggcc canccttac caggctggaa gaaatttttnc ctttttttttt ttttgaagg     840 cntttnttaa attgaacctn aattcncccc cccaaaaaaa aacccnccng ggggcggat      900 ttccaaaaac naattcccct accaaaaaac aaaaaccnc ccttnttccc ttccncccct       960 ttctttaat tagggagaga tnaagccccc caatttccng gnctngatnn gtttccccc      1020 ccccccattt ccnaaactt tcccancna ggaanccncc ctttttttng gtcngattna      1080
ncaaccttcc aaaccatttt tccnnaaaaa ntttgntngg ngggaaaaan acctnnttttt    1140 atagan                                                                 1146

<210> SEQ ID NO 10
<211> LENGTH: 545
<212> TYPE: DNA
<213> ORGANISM: Homo sapien

<400> SEQUENCE: 10
cttcattggg tacgggcccc ctcgaggtcg acggtatcga taagcttgat atcgaattcc       60
tgcagcccgg gggatccact agttctagag tcaggaagaa ccaccaacct tcctgatttt     120
tattggctct gagttctgag gccagttttc ttcttctgtt gagtatgcgg gattgtcagg     180
cagatctggc tgtggaaagg agactgtggg cagcaagttt agaggcgtga ctgaaagtca     240
cactgcatct tgagctgctg aatcagcttt ctggttacca cgggcaacag ccgtgttttc     300
cttttgatgt cctttacagt ggattacagc cacctgctga ggtgagtagc ccacgctcct     360
ggtagatggc tccacgtaca tgcacagtag caaaggcgta cctgctgtca gtgttaacgt     420
taatatcctt accccatcgg agagcctgag tgagggcgat caattcagcc cttttgtgct     480
gaggtgtttg ctggttaagc cctgaaccca caacacatct gtctccatgg taacagctgc     540
accgg                                                                  545

<210> SEQ ID NO 11
<211> LENGTH: 196
<212> TYPE: DNA
<213> ORGANISM: Homo sapien

<400> SEQUENCE: 11
tctcctaggc tgggcacagt ggctcatacc tgtaatcctg accgtttcag aggctcaggt       60
ggggggatcg cttgagccca agatttcaag actagtctgg gtaacatagt gagaccctat     120
ctctacgaaa aaataaaaaa atgagcctgg tgtagtggca cacaccagct gaggagggag     180
aatcgagcct aggaga                                                     196

<210> SEQ ID NO 12
<211> LENGTH: 388
<212> TYPE: DNA
<213> ORGANISM: Homo sapien
```

<220> FEATURE:
<221> NAME/KEY: misc_feature
<222> LOCATION: (1)...(388)
<223> OTHER INFORMATION: n = A,T,C or G

<400> SEQUENCE: 12

| | | | | | |
|---|---|---|---|---|---|
| tctcctaggc | ttgggggctc | tgactagaaa | ttcaaggaac | ctgggattca | agtccaactg | 60 |
| tgacaccaac | ttacactgtg | gnctccaata | aactgcttct | ttcctattcc | ctctctatta | 120 |
| aataaaataa | ggaaaacgat | gtctgtgtat | agccaagtca | gntatcctaa | aaggagatac | 180 |
| taagtgacat | taaatatcag | aatgtaaaac | ctgggaacca | ggttcccagc | ctgggattaa | 240 |
| actgacagca | agaagactga | acagtactac | tgtgaaaagc | ccgaagnggc | aatatgttca | 300 |
| ctctaccgtt | gaaggatggc | tgggagaatg | aatgctctgt | cccccagtcc | caagctcact | 360 |
| tactatacct | cctttatagc | ctaggaga | | | | 388 |

<210> SEQ ID NO 13
<211> LENGTH: 337
<212> TYPE: DNA
<213> ORGANISM: Homo sapien

<400> SEQUENCE: 13

| | | | | | |
|---|---|---|---|---|---|
| tagtagttgc | ctataatcat | gtttctcatt | attttcacat | tttattaacc | aatttctgtt | 60 |
| taccctgaaa | aatatgaggg | aaatatatga | acagggagg | caatgttcag | ataattgatc | 120 |
| acaagatatg | atttctacat | cagatgctct | ttcctttcct | gtttatttcc | ttttttatttc | 180 |
| ggttgtgggg | tcgaatgtaa | tagctttgtt | tcaagagaga | gttttggcag | tttctgtagc | 240 |
| ttctgacact | gctcatgtct | ccaggcatct | atttgcactt | taggaggtgt | cgtgggagac | 300 |
| tgagaggtct | attttttcca | tatttgggca | actacta | | | 337 |

<210> SEQ ID NO 14
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 14

| | | | | | |
|---|---|---|---|---|---|
| tagtagttgc | catacagtgc | ctttccattt | atttaacccc | cacctgaacg | gcataaactg | 60 |
| agtgttcagc | tggtgttttt | tactgtaaac | aataaggaga | ctttgctctt | catttaaacc | 120 |
| aaaatcatat | ttcatatttt | acgctcgagg | gttttttaccg | gttcctttttt | acactcctta | 180 |
| aaacagtttt | taagtcgttt | ggaacaagat | attttttctt | tcctggcagc | ttttaacatt | 240 |
| atagcaaatt | tgtgtctggg | ggactgctgg | tcactgtttc | tcacagttgc | aaatcaaggc | 300 |
| atttgcaacc | aagaaaaaaa | aatttttttg | ttttatttga | aactgaccg | gataaacggt | 360 |
| gtttggagcg | gctgctgtat | atagttttaa | atggtttatt | gcacctcctt | aagttgcact | 420 |
| tatgtggggg | gggnttttg | natagaaagt | nttttantcac | anagtcacag | ggacttttnt | 480 |
| cttttggnna | ctgagctaaa | aagggctgnt | tttcgggtgg | gggcagatga | aggctcacag | 540 |
| gaggcctttc | tcttagaggg | gggaactnct | a | | | 571 |

<210> SEQ ID NO 15
<211> LENGTH: 548
<212> TYPE: DNA
<213> ORGANISM: Homo sapien
<220> FEATURE:

<221> NAME/KEY: misc_feature
<222> LOCATION: (1)...(548)
<223> OTHER INFORMATION: n = A,T,C or G

<400> SEQUENCE: 15

```
tatatattta ataacttaaa tatattttga tcacccactg gggtgataag acaatagata    60
taaaagtatt tccaaaaagc ataaaaccaa agtatcatac caaaccaaat tcatactgct   120
tcccccaccc gcactgaaac ttcaccttct aactgtctac ctaaccaaat tctacccttc   180
aagtctttgg tgcgtgctca ctactctttt tttttttttt tttnttttgg agatggagtc   240
tggctgtgca gcccaggggt ggagtacaat ggcacaacct cagctcactg naacctccgc   300
ctcccaggtt catgagattc tcctgnttca gccttcccag tagctgggac tacaggtgtg   360
catcaccatg cctggntaat ctttttttngt tttngggtag agatgggggt tttacatgtt   420
ggccaggntg gtntcgaact cctgacctca agtgatccac ccacctcagg ctcccaaagt   480
gctaggatta cagacatgag ccactgngcc cagncctggt gcatgctcac ttctctaggc   540
aactacta                                                            548
```

<210> SEQ ID NO 16
<211> LENGTH: 638
<212> TYPE: DNA
<213> ORGANISM: Homo sapien
<220> FEATURE:
<221> NAME/KEY: misc_feature
<222> LOCATION: (1)...(638)
<223> OTHER INFORMATION: n = A,T,C or G

<400> SEQUENCE: 16

```
ttccgttatg cacatgcaga atattctatc ggtacttcag ctattactca ttttgatggc    60
gcaatccgag cctatcctca agatgagtat ttagaaagaa ttgatttagc gatagaccaa   120
gctggtaagc actctgacta cacgaaattg ttcagatgtg atggatttat gacagttgat   180
ctttggaaga gattattaag tgattatttt aaagggaatc cattaattcc agaatatctt   240
ggtttagctc aagatgatat agaaatagaa cagaaagaga ctacaaatga agatgtatca   300
ccaactgata ttgaagagcc tatagtagaa aatgaattag ctgcatttat tagccttaca   360
catagcgatt ttcctgatga atcttatatt cagccatcga catagcatta cctgatgggc   420
aaccttacga ataatagaaa ctgggtgcgg ggctattgat gaattcatcc ncagtaaatt   480
tggatatnac aaaatataac tcgattgcat tggatgatg gaatactaaa tctggcaaaa   540
gtaactttgg agctactagt aacctctctt tttgagatgc aaaattttct tttagggttt   600
cttattctct actttacgga tattggagca taacggga                           638
```

<210> SEQ ID NO 17
<211> LENGTH: 286
<212> TYPE: DNA
<213> ORGANISM: Homo sapien

<400> SEQUENCE: 17

```
actgatggat gtcgccggag gcgaggggcc ttatctgatg ctcggctgcc tgttcgtgat    60
gtgcgcggcg attgggctgt ttatctcaaa caccgccacg gcggtgctga tggcgcctat   120
tgccttagcg gcggcgaagt caatgggcgt ctcacctat ccttttgcca tggtggtggc   180
gatggcggct tcggcggcgt ttatgacccc ggtctcctcg ccggttaaca ccctggtgct   240
tggccctggc aagtactcat ttagcgattt tgtcaaaata ggcgtg                  286
```

<210> SEQ ID NO 18
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 18

| | | | | |  |
|---|---|---|---|---|---|
| tcggtcatag | cagccccttc | ttctcaattt | catctgtcac | taccctggtg tagtatctca | 60 |
| tagccttaca | tttttatagc | ctcctccctg | gtctgtcttt | tgattttcct gcctgtaatc | 120 |
| catatcacac | ataactgcaa | gtaaacattt | ctaaagtgtg | gttatgctca tgtcactcct | 180 |
| gtgncaagaa | atagtttcca | ttaccgtctt | aataaaattc | ggatttgttc tttnctattn | 240 |
| tcactcttca | cctatgaccg | aa | | | 262 |

<210> SEQ ID NO 19
<211> LENGTH: 261
<212> TYPE: DNA
<213> ORGANISM: Homo sapien

<400> SEQUENCE: 19

| | | | | |  |
|---|---|---|---|---|---|
| tcggtcatag | caaagccagt | ggtttgagct | ctctactgtg | taaactccta aaccaaggcc | 60 |
| atttatgata | aatggtggca | ggattttat | tataaacatg | tacccatgca aatttcctat | 120 |
| aactctgaga | tatattcttc | tacatttaaa | caataaaaat | aatctatttt taaaagccta | 180 |
| atttgcgtag | ttaggtaaga | gtgtttaatg | agagggtata | aggtataaat caccagtcaa | 240 |
| cgtttctctg | cctatgaccg | a | | | 261 |

<210> SEQ ID NO 20
<211> LENGTH: 294
<212> TYPE: DNA
<213> ORGANISM: Homo sapien
<220> FEATURE:
<221> NAME/KEY: misc_feature
<222> LOCATION: (1)...(294)
<223> OTHER INFORMATION: n = A,T,C or G

<400> SEQUENCE: 20

| | | | | |  |
|---|---|---|---|---|---|
| tacaacgagg | cgacgtcggt | aaaatcggac | atgaagccac | cgctggtctt ttcgtccgag | 60 |
| cgataggcgc | cggccagcca | gcggaacggt | tgcccggatg | gcgaagcgag ccggagttct | 120 |
| tcggactgag | tatgaatctt | gttgtgaaaa | tactcgccgc | cttcgttcga cgacgtcgcg | 180 |
| tcgaaatctt | cganctcctt | acgatcgaag | tcttcgtggg | cgacgatcgc ggtcagttcc | 240 |
| gccccaccga | aatcatggtt | gagccggatg | ctgnccccga | agncctcgtt tgtn | 294 |

<210> SEQ ID NO 21
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 21

| | | | | |  |
|---|---|---|---|---|---|
| ttggtaaagg | gcatggacgc | agacgcctga | cgtttggctg | aaaatctttc attgattcgt | 60 |
| atcaatgaat | aggaaaattc | ccaaagaggg | aatgtcctgt | tgctcgccag ttttttntgtt | 120 |
| gttctcatgg | anaaggcaan | gagctcttca | gactattggn | attntcgttc ggtcttctgc | 180 |

```
caactagtcg ncttgcnang atcttcat                                              208

<210> SEQ ID NO 22
<211> LENGTH: 287
<212> TYPE: DNA
<213> ORGANISM: Homo sapien
<220> FEATURE:
<221> NAME/KEY: misc_feature
<222> LOCATION: (1)...(287)
<223> OTHER INFORMATION: n = A,T,C or G

<400> SEQUENCE: 22
nccnttgagc tgagtgattg agatntgtaa tggttgtaag ggtgattcag gcggattagg    60
gtggcgggtc acccggcagt gggtctcccg acaggccagc aggatttggg gcaggtacgg   120
ngtgcgcatc gctcgactat atgctatggc aggcgagccg tggaaggngg atcaggtcac   180
ggcgctggag ctttccacgg tccatgnatt gngatggctg ttctaggcgg ctgttgccaa   240
gcgtgatggt acgctggctg gagcattgat ttctggtgcc aaggtgg                 287

<210> SEQ ID NO 23
<211> LENGTH: 204
<212> TYPE: DNA
<213> ORGANISM: Homo sapien
<220> FEATURE:
<221> NAME/KEY: misc_feature
<222> LOCATION: (1)...(204)
<223> OTHER INFORMATION: n = A,T,C or G

<400> SEQUENCE: 23
ttgggtaaag ggagcaagga gaaggcatgg agaggctcan gctggtcctg gcctacgact    60
gggccaagct gtcgccgggg atggtggaga actgaagcgg gacctcctcg aggtcctccg   120
ncgttacttc nccgtccagg aggagggtct ttccgtggtc tnggaggagc gggggggagaa  180 gatnctcctc atggtcnaca tccc                                          204

<210> SEQ ID NO 24
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 24
tggattggtc aggagcgggt agagtggcac cattgagggg atattcaaaa atattatttt    60
gtcctaaatg atagttgctg agttttctt tgacccatga gttatattgg agtttatttt   120
ttaactttcc aatcgcatgg acatgttaga cttattttct gttaatgatt nctatttta    180 ttaaattgga tttgagaaat tggttnttat tatatcaatt tttggtattt gttgagtttg   240
acattatagc ttagtatgtg acca                                          264

<210> SEQ ID NO 25
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 25
ttacaacgag gggaaactcc gtctctacaa aaattaaaaa attagccagg tgtggtggtg    60
```

| | |
|---|---|
| tgcacccgca atcccagcta cttgggaggt tgagacacaa gantcaccta natgtgggag | 120 |
| gtcaaggttg catgagtcat gattgtgcca ctgcactcca gcctgggtga cagaccgaga | 180 |
| ccctgcctca anaganaang aataggaagt tcagaaatcn tggntgtggn gcccagcaat | 240 |
| ctgcatctat ncaacccctg caggcaangc tgatgcagcc tangttcaag agctgctgtt | 300 |
| tctggaggca gcagttnggg cttccatcca gtatcacggc cacactcgca cnagccatct | 360 |
| gtcctccgtn tgtnac | 376 |

<210> SEQ ID NO 26
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 26

| | |
|---|---|
| ttacaacgag gggaaactcc gtctctacaa aaattaaaaa attagccagg tgtggtggtg | 60 |
| tgcacctgta atcccagcta cttgggcggc tgagacacaa gaaccaccta aatgtgggag | 120 |
| ggtcaaggtt gcatgagtca tgatcgcgcc actgcactcc agcctgggtg acagactgag | 180 |
| accctgcctc aaaagaaaaa gaataggaag ttcagaaacc ctgggtgtgg ngcccagcaa | 240 |
| tctgcattta acaatccct gcaggcaatg ctgatgcagc taagttcaa gagctgctgt | 300 |
| tctggaggca gnagtaaggg cttccatcca gcatcacggn caacactgca aaagcacctg | 360 |
| tcctcgttgg ta | 372 |

<210> SEQ ID NO 27
<211> LENGTH: 477
<212> TYPE: DNA
<213> ORGANISM: Homo sapien

<400> SEQUENCE: 27

| | |
|---|---|
| ttctgtccac atctacaagt tttatttatt ttgtgggttt tcagggtgac taagtttttc | 60 |
| cctacattga aaagagaagt tgctaaaagg tgcacaggaa atcattttt taagtgaata | 120 |
| tgataatatg ggtccgtgct aatacaact gagacatatt tgttctctgt tttttagag | 180 |
| tcacctctta aagtccaatc ccacaatggt gaaaaaaaaa tagaaagtat ttgttctacc | 240 |
| tttaaggaga ctgcagggat tctccttgaa aacggagtat ggaatcaatc ttaaataaat | 300 |
| atgaaattgg ttggtcttct gggataagaa attcccaact cagtgtgctg aaattcacct | 360 |
| gactttttt gggaaaaaat agtcgaaaat gtcaatttgg tccataaaat acatgttact | 420 |
| attaaaagat atttaaagac aaattctttc agagctctaa gattggtgtg gacagaa | 477 |

<210> SEQ ID NO 28
<211> LENGTH: 438
<212> TYPE: DNA
<213> ORGANISM: Homo sapien
<220> FEATURE:
<221> NAME/KEY: misc_feature
<222> LOCATION: (1)...(438)
<223> OTHER INFORMATION: n = A,T,C or G

<400> SEQUENCE: 28

| | |
|---|---|
| tctncaacct cttgantgtc aaaaaccttn taggctatct ctaaaagctg actggtattc | 60 |
| attccagcaa aatccctcta gttttggag tttccttta ctatctgggg ctgcctgagc | 120 |

-continued

| | |
|---|---|
| cacaaatgcc aaattaagag catggctatt ttcgggggct gacaggtcaa aaggggtgta | 180 |
| aatccgataa gcctcctgga ggtgctctaa aaacactcct ggtgactcat catgcccctg | 240 |
| gacgacttca atcgncttag acaagtttat aggtttctgg gcagctccct gaatacccac | 300 |
| gaggagatac cggtggaaat cgtcaaaagt tctccctcca cttgagaaat ttgggtccca | 360 |
| attaggtccc aattgggtct ctaatcacta ttcctctagc ttcctcctcc ggnctattgg | 420 |
| ttgatgtgag gttgaaga | 438 |

<210> SEQ ID NO 29
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 29

| | |
|---|---|
| aagagggtac cagccccaag ccttgacaac ttccataggg tgtcaagcct gtgggtgcac | 60 |
| agaagtcaaa aattgagttt tgggatcctc agcctagatt tcagaggata taaagaaaca | 120 |
| cctaacacct agatattcag acaaaagttt actacaggga tgaagctttc acggaaaacc | 180 |
| tctactagga aagtacagaa gagaaatgtg ggtttggagc ccccaaacag aatcccctct | 240 |
| agaacactgc ctaatgaaac tgtgagaaga tggccactgt catccagaca ccagaatgat | 300 |
| agacccacca aaaacttatg ccatattgcc tataaaacct acagacactc aatgccagcc | 360 |
| ccatgaaaaa aaaactgaga agaagactgt nccctacaat gccaccggag cagaactgcc | 420 |
| ccaggccatg gaagcacagc tcttatatca atgtgacctg gatgttgaga catggaatcc | 480 |
| nangaaatcn ttttaanact tccacggttn aatgactgcc ctattanatt cngaacttan | 540 |
| atccnggcct gtgacctctt tgctttggcc attccccctt tttggaatgg ctntttttt | 600 |
| cccatgcctg tnccctctta | 620 |

<210> SEQ ID NO 30
<211> LENGTH: 100
<212> TYPE: DNA
<213> ORGANISM: Homo sapien

<400> SEQUENCE: 30

| | |
|---|---|
| ttacaacgag ggggtcaatg tcataaatgt cacaataaaa caatctcttc ttttttttt | 60 |
| tttttttttt tttttttttt tttttttttt tttttttttt | 100 |

<210> SEQ ID NO 31
<211> LENGTH: 762
<212> TYPE: DNA
<213> ORGANISM: Homo sapien
<220> FEATURE:
<221> NAME/KEY: misc_feature
<222> LOCATION: (1)...(762)
<223> OTHER INFORMATION: n = A,T,C or G

<400> SEQUENCE: 31

| | |
|---|---|
| tagtctatgc gccggacaga gcagaattaa attggaagtt gccctccgga ctttctaccc | 60 |
| acactcttcc tgaaaagaga aagaaaagag gcaggaaaga ggttaggatt tcattttcaa | 120 |
| gagtcagcta attaggagag cagagtttag acagcagtag gcaccccatg atacaaaacca | 180 |
| tggacaaagt ccctgtttag taactgccag acatgatcct gctcaggttt tgaaatctct | 240 |
| ctgcccataa aagatggaga gcaggagtgc catccacatc aacacgtgtc caagaaagag | 300 |

```
tctcagggag acaagggtat caaaaaacaa gattcttaat gggaaggaaa tcaaaccaaa      360
aaattagatt tttctctaca tatatataat atacagatat ttaacacatt attccagagg      420
tggctccagt ccttggggct tgagagatgg tgaaaacttt tgttccacat taacttctgc      480
tctcaaattc tgaagtatat cagaatggga caggcaatgt tttgctccac actggggcac      540
agacccaaat ggttctgtgc cgaagaaga gaagcccgaa agacatgaag gatgcttaag       600
gggggttggg aaagccaaat tggtantatc ttttcctcct gcctgtgttc cngaagtctc      660
cnctgaagga attcttaaaa cccttttgtga ggaaatgccc ccttaccatg acaantggtc     720
ccattgcttt tagggngatg gaaacaccaa gggttttgat cc                         762
```

```
<210> SEQ ID NO 32
<211> LENGTH: 276
<212> TYPE: DNA
<213> ORGANISM: Homo sapien

<400> SEQUENCE: 32
tagtctatgc gtgtattaac ctcccctccc tcagtaacaa ccaaagaggc aggagctgtt       60
attaccaacc ccatttaca gatgcatcaa taatgacaga gaagtgaagt gacttgcgca       120
cacaaccagt aaattggcag agtcagattt gaatccatgg agtctggtct gcactttcaa      180
tcaccgaata ccctttctaa gaaacgtgtg ctgaatgagt gcatggataa atcagtgtct      240
actcaacatc tttgcctaga tatcccgcat agacta                                276
```

```
<210> SEQ ID NO 33
<211> LENGTH: 477
<212> TYPE: DNA
<213> ORGANISM: Homo sapien

<400> SEQUENCE: 33
tagtagttgc caaatatttg aaaatttacc cagaagtgat tgaaaacttt ttggaaacaa       60
aaacaaataa agccaaaagg taaaataaaa atatctttgc actctcgtta ttacctatcc      120
ataacttttt caccgtaagc tctcctgctt gttagtgtag tgtggttata ttaaactttt      180
tagttattat ttttattca cttttccact agaaagtcat tattgattta gcacacatgt       240
tgatctcatt tcatttttc ttttttatagg caaaatttga tgctatgcaa caaaaatact      300
caagcccatt atcttttttc cccccgaaat ctgaaaattg caggggacag agggaagtta     360
tcccattaaa aaattgtaaa tatgttcagt ttatgtttaa aaatgcacaa aacataagaa      420
aattgtgttt acttgagctg ctgattgtaa gcagttttat ctcaggggca actacta        477
```

```
<210> SEQ ID NO 34
<211> LENGTH: 631
<212> TYPE: DNA
<213> ORGANISM: Homo sapien

<400> SEQUENCE: 34
tagtagttgc caattcagat gatcagaaat gctgctttcc tcagcattgt cttgttaaac       60
cgcatgccat ttggaacttt ggcagtgaga agccaaaagg aagaggtgaa tgacatatat      120
atatatatat attcaatgaa agtaaaatgt atatgctcat atactttcta gttatcagaa      180
tgagttaagc tttatgccat tgggctgctg catatttaa tcagaagata aagaaaatc       240 tgggcatttt tagaatgtga tacatgtttt tttaaaactg ttaatatta tttcgatatt       300 tgtctaagaa ccggaatgtt cttaaaattt actaaaacag tattgtttga ggaagagaaa     360
```

```
actgtactgt tgccattat tacagtcgta caagtgcatg tcaagtcacc cactctctca    420
ggcatcagta tccacctcat agctttacac attttgacgg ggaatattgc agcatcctca    480
ggcctgacat ctgggaaagg ctcagatcca cctactgctc cttgctcgtt gatttgtttt    540
aaaatattgt gcctggtgtc acttttaagc cacagccctg cctaaaagcc agcagagaac    600
agaacccgca ccattctata ggcaactact a                                   631
```

<210> SEQ ID NO 35
<211> LENGTH: 578
<212> TYPE: DNA
<213> ORGANISM: Homo sapien

<400> SEQUENCE: 35

```
tagtagttgc catcccatat tacagaaggc tctgtataca tgacttattt ggaagtgatc    60
tgttttctct ccaaacccat ttatcgtaat ttcaccagtc ttggatcaat cttggttttcc   120 actgatacca tgaacctac ttggagcaga cattgcacag ttttctgtgg taaaaactaa    180
aggtttattt gctaagctgt catcttatgc ttagtatttt ttttttacag tggggaattg    240
ctgagattac attttgttat tcattagata ctttgggata acttgacact gtcttctttt    300
tttcgctttt aattgctatc atcatgcttt tgaaacaaga acacattagt cctcaagtat    360
tacataagct tgcttgttac gcctggtggt ttaaaggact atctttggcc tcaggttcac    420
aagaatgggc aaagtgtttc cttatgttct gtagttctca ataaaagatt gccaggggcc    480
gggtactgtg gctcgcactg taatcccagc actttgggaa gctgaggctg gcggatcatg    540
ttagggcagg tgttcgaaac cagcctgggc aactacta                            578
```

<210> SEQ ID NO 36
<211> LENGTH: 583
<212> TYPE: DNA
<213> ORGANISM: Homo sapien

<400> SEQUENCE: 36

```
tagtagttgc ctgtaatccc agcaactcag gaggctgggg caggagaatc agttgaacct    60
gggaggcaga agttgtaatt agcaaagatc gcaccattgc acttcagcct gggcaacaag    120
agtgagattc catctcaaaa acaaaaaaaa gaaaagaaa agaaaaggaa aaacgtata     180 aacccagcca aaacaaaatg atcattcttt taataagcaa gactaattta atgtgtttat    240
ttaatcaaag cagttgaatc ttctgagtta ttggtgaaaa tacccatgta gttaatttag    300
ggttcttact tgggtgaacg tttgatgttc acaggttata aaatggttaa caaggaaaat    360
gatgcataaa gaatcttata aactactaaa ataaataaa atataaatgg ataggtgcta    420
tggatggagt ttttgtgtaa tttaaaatct tgaagtcatt ttggatgctc attggttgtc    480
tggtaatttc cattaggaaa aggttatgat atggggaaac tgtttctgga aattgcggaa    540
tgtttctcat ctgtaaaatg ctagtatctc agggcaacta cta                      583
```

<210> SEQ ID NO 37
<211> LENGTH: 716
<212> TYPE: DNA
<213> ORGANISM: Homo sapien
<220> FEATURE:
<221> NAME/KEY: misc_feature
<222> LOCATION: (1)...(716)
<223> OTHER INFORMATION: n = A,T,C or G

<400> SEQUENCE: 37

```
gatctactag tcatntggat tctatccatg gcagctaagc ctttctgaat ggattctact    60
```

```
gctttcttgt tctttaatcc agacccttat atatgtttat gttcacaggc agggcaatgt    120
ttagtgaaaa caattctaaa ttttttattt tgcattttca tgctaatttc cgtcacactc    180
cagcaggctt cctgggagaa taaggagaaa tacagctaaa gacattgtcc ctgcttactt    240
acagcctaat ggtatgcaaa accacttcaa taaagtaaca ggaaaagtac taaccaggta    300
gaatggacca aaactgatat agaaaaatca gaggaagaga ggaacaaata tttactgagt    360
cctagaatgt acaaggcttt ttaattacat attttatgta aggcctgcaa aaacaggtg     420 agtaatcaac atttgtccca ttttacatat aaggaaactg aagcttaaat tgaataattt    480
aatgcataga ttttatagtt agaccatgtt caggtcccta tgttatactt actagctgta    540
tgaatatgag aaaataattt tgttattttc ttggcatcag tattttcatc tgcaaaataa    600
agctaaagtt atttagcaaa cagtcagcat agtgcctgat acatagtagg tgctccaaac    660
atgattacnc tantattngg tattanaaaa atccaatata ggcntggata aaccg         716

<210> SEQ ID NO 38
<211> LENGTH: 688
<212> TYPE: DNA
<213> ORGANISM: Homo sapien
<220> FEATURE:
<221> NAME/KEY: misc_feature
<222> LOCATION: (1)...(688)
<223> OTHER INFORMATION: n = A,T,C or G

<400> SEQUENCE: 38
ttctgtccac atatcatccc actttaattg ttaatcagca aaactttcaa tgaaaaatca     60 tccatttaa ccaggatcac accaggaaac tgaaggtgta ttttttttta ccttaaaaaa    120
aaaaaaaaaa accaaacaaa ccaaaacaga ttaacagcaa agagttctaa aaaatttaca    180
tttctcttac aactgtcatt cagagaacaa tagttcttaa gtctgttaaa tcttggcatt    240
aacagagaaa cttgatgaan agttgtactt ggaatattgt ggattttttt ttttgtctaa    300
tctcccccta ttgttttgcc aacagtaatt taagtttgtg tggaacatcc ccgtagttga    360
agtgtaaaca atgtatagga aggaatatat gataagatga tgcatcacat atgcattaca    420
tgtagggacc ttcacaactt catgcactca gaaaacatgc ttgaagagga ggagaggacg    480
gcccagggtc accatccagg tgccttgagg acagagaatg cagaagtggc actgttgaaa    540
tttagaagac catgtgtgaa tggtttcagg cctgggatgt tgccaccaa gaagtgcctc     600 cgagaaattt ctttcccatt tggaatacag gtggcttga tgggtacggt gggtgaccca    660
acgaagaaaa tgaaattctg ccctttcc                                       688

<210> SEQ ID NO 39
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 39
tagtagttgc cgcnnaccta aaanttggaa agcatgatgt ctaggaaaca tantaaaata     60
gggtatgcct atgtgctaca gagagatgtt agcatttaaa gtgcatantt ttatgtattt    120
tgacaaatgc atatncctct ataatccaca actgattacg aagctattac aattaaaaag    180
tttggccggg cgtggtgggc ggtggctgac gcctgtaatc ccagcacttt gggaggccga    240
```

-continued

```
ggcacgcgga tcacgaggtc gggagttcaa gaccatcctg ctaacacgg tgaaagtcca      300 tctctactaa aaatacgaaa aaattacccc ggcgtggtgg cgggcgcctg tagtcccagc      360
tactccggag gctgaggcag gagaatggcg tgaacccagg acacggagct tgcagtgtgc      420
caacatcacg tcactgccct ccagcctggg ggacaggaac aagantcccg tcctcanaaa      480
agaaaaatac tactnatant ttcnacttta ttttaantta cacagaactn cctcttggta      540
cccccttacc attcatctca cccacctcct atagggcacn nctaa                      585
```

<210> SEQ ID NO 40
<211> LENGTH: 475
<212> TYPE: DNA
<213> ORGANISM: Homo sapien

<400> SEQUENCE: 40

```
tctgtccaca ccaatcttag aagctctgaa aagaatttgt ctttaaatat cttttaatag      60
taacatgtat tttatggacc aaattgacat tttcgactgt ttttccaaa aaagtcaggt       120 gaatttcagc acactgagtt gggaatttct tatcccagaa gaccaaccaa tttcatattt      180
atttaagatt gattccatac tccgttttca aggagaatcc ctgcagtctc cttaaaggta      240
gaacaaatac ttcctatttt tttttcacca ttgtgggatt ggactttaag aggtgactct      300
aaaaaaacag agaacaaata tgtctcagtt gtattaagca cggacccata ttatcatatt      360
cacttaaaaa aatgatttcc tgtgcacctt ttggcaactt ctcttttcaa tgtagggaaa      420
aacttagtca ccctgaaaac ccacaaaata aataaaactt gtagatgtgg acaga          475
```

<210> SEQ ID NO 41
<211> LENGTH: 423
<212> TYPE: DNA
<213> ORGANISM: Homo sapien

<400> SEQUENCE: 41

```
taagagggta catcgggtaa gaacgtaggc acatctagag cttagagaag tctggggtag      60
gaaaaaaatc taagtatta taagggtata ggtaacattt aaaagtaggg ctagctgaca       120
ttatttagaa agaacacata cggagagata agggcaaagg actaagacca gaggaacact     180
aatatttagt gatcacttcc attcttggta aaaatagtaa cttttaagtt agcttcaagg      240 aagattttg gccatgatta gttgtcaaaa gttagttctc ttgggtttat attactaatt       300
ttgttttaag atccttgtta gtgctttaat aaagtcatgt tatatcaaac gctctaaaac      360
attgtagcat gttaaatgtc acaatatact taccatttgt tgtatatggc tgtaccctct      420
cta                                                                    423
```

<210> SEQ ID NO 42
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 42

```
tctcctaggc taatgtgtgt gtttctgtaa agtaaaaag ttaaaatttt taaaataga       60 aaaaagctta tagaataaga atatgaagaa agaaatatt tttgtacatt tgcacaatga       120
gtttatgttt taagctaagt gttattacaa aagagccaaa aaggttttaa aaattaaaac      180
gtttgtaaag ttacagtacc cttatgttaa tttataattg aagaaagaaa aacttttttt       240
```

| | |
|---|---|
| tataaatgta gtgtagccta agcatacagt atttataaag tctggcagtg ttcaataatg | 300 |
| tcctaggcct tcacattcac tcactgactc acccagagca acttccagtc ctgtaagctc | 360 |
| cattcgtggt aagtgcccta tacaggtgca ccatttattt tacagtattt ttactgtacc | 420 |
| ttctctatgt ttccatatgt ttcgatatac aaataccact ggttactatn gcccnacagg | 480 |
| taattccagt aacacggcct gtatacgtct ggtanccta gngaaga | 527 |

<210> SEQ ID NO 43
<211> LENGTH: 331
<212> TYPE: DNA
<213> ORGANISM: Homo sapien

<400> SEQUENCE: 43

| | |
|---|---|
| tcttcaacct cgtaggacaa ctctcatatg cctgggcact atttttaggt tactaccttg | 60 |
| gctgcccttc tttaagaaaa aaaaaagaag aaaaaagaac ttttccacaa gtttctcttc | 120 |
| ctctagttgg aaaattagag aaatcatgtt tttaattttg tgttatttca gatcacaaat | 180 |
| tcaaacactt gtaaacatta agcttctgtt caatcccctg ggaagaggat tcattctgat | 240 |
| atttacggtt caaaagaagt tgtaatattg tgcttggaac acagagaacc agttattaac | 300 |
| ttcctactac tattatataa taaataataa c | 331 |

<210> SEQ ID NO 44
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 44

| | |
|---|---|
| ggcttagtag ttgccaggca aaatarcgtt gattctcctc aggagccacc cccaacaccc | 60 |
| ctgtttgctt ctagacctat acctagacta aagtcccagc agaccctag aggtgaggtt | 120 |
| cagagtgacc cttgaggaga tgtgctacac tagaaaagaa ctgcttgagt tttctaattt | 180 |
| atataagcag aaatctggag aagagtcata ggaatggata ttaagggtgt gagataatgg | 240 |
| cggaaggaat atagagttgg atcaggctgg acttattgat ttgaacccac taagtagaga | 300 |
| ttctgctttt gatgttgcag ctcagggagt taaaaaaggt tttaatggtt ctaatagttt | 360 |
| atttgcttgg ttagctgaaa tatggataaa agatggccca ctgtgagcaa gctggaaatg | 420 |
| cctgatctct ctcagtttaa tgtagaggaa gggatccaaa agtttaggga ganttggatg | 480 |
| ctggraktgg attggtcact ttgrgaccta cccwtcccag ctgggagggt ccagaagata | 540 |
| caccccttgac caacgctttg cgaaatggat ttgtgatggc ggcaactact aa | 592 |

<210> SEQ ID NO 45
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 45

| | |
|---|---|
| ggcttagtag ttgccattgc gagtgcttgc tcaacgagcg ttgaacatgg cggattgtct | 60 |
| agattcaacg gatttgagtt ttaccagcaa agcgaaccaa gcgcggccca gagaattatg | 120 |

```
ggttggttgg ctttgaaaag atggaaatcc tgtaggccta gtcagaaaag ccttcttgca    180
gaacagttgg ttctcgggcg aacgctcatc aagatgccca ttggaaaggc tagcgtgtat    240
ttgggagagc ctgatagcgt gtcttctgat gatgtttgtg cttggacagt gacaaaagat    300
atgcaaagca agtccgaact agacgtcaag cttcgtgagc aaattattgt agactcctac    360
ttatactgtg aggaatgata gccaagggtg gggactttaa gactaaggtg gtttgtactt    420
gcgccgatga tcccaggcag aaagamctga tcgctagttt tatacgggca actactaagc    480
cgaattccag cacactggcg gccgttacta attggatccg anctcggtac cagcttgatg    540
catascttga gttwtctata ntgtcnc                                        567

<210> SEQ ID NO 46
<211> LENGTH: 908
<212> TYPE: DNA
<213> ORGANISM: Homo sapien
<220> FEATURE:
<221> NAME/KEY: misc_feature
<222> LOCATION: (1)...(908)
<223> OTHER INFORMATION: n = A,T,C or G

<400> SEQUENCE: 46
gagcgaaaga ccgagggcag ngnntangng cgangaagcg gagagggcca aaaagcaacc    60
gctttccccg gggggtgccg attcattaag gcaggtggag gacaggtttc ccgatggaag   120
gcggcagggg cgcaagcaat taatgtgagt aggccattca ttagcacccg ggcttaacat   180
ttaagcttcg ggttggtatg tggtgggaat tgtgagcgga taacaatttc acacaggaaa   240
cagctatgac catgattacg ccaagctatt taggtgacat tatagaataa ctcaagttat   300
gcatcaagct tggtaccgag ttcggatcca ctagtaacgg ccgccagtgt gtggaattcg   360
gcttagtagt tgccgaccat ggagtgctac ctaggctaga atacctgagy tcctccctag   420
cctcactcac attaaattgt atcttttcta cattagatgt cctcagcgcc ttatttctgc   480
tggacwatcg ataaattaat cctgatagga tgatagcagc agattaatta ctgagagtat   540
gttaatgtgt catccctcct atataacgta tttgcatttt aatggagcaa ttctggagat   600
aatccctgaa ggcaaaggaa tgaatcttga gggtgagaaa gccagaatca gtgtccagct   660
gcagttgtgg gagaaggtga tattatgtat gtctcagaag tgacaccata tgggcaacta   720
ctaagcccga attccagcac actggcgggc gttactaatg gatccgagct cggtaccaag   780
cttgatgcat agcttgagta tctatagtgt cactaaatag cctggcgtta tcatggtcat   840
agctgtttcc tgtgtgaaat tgttatccgc tcccaattcc ccccaccata cgagccggaa   900
cataaagt                                                            908

<210> SEQ ID NO 47
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 47
tgccaacaag gaaagtttta aatttcccct tgaggattct tggtgatcat caaattcagt    60 ggttttaag gttgtttct gtcaaataac tctaacttta agccaaacag tatatggaag   120
cacagataka atattacaca gataaaagag gagttgatct aaagtaraga tagttggggg   180
ctttaatttc tggaacctag gtctccccat cttcttctgt gctgaggaac ttcttggaag   240
```

```
cggggattct aaagttcttt ggaagacagt ttgaaaacca ccatgttgtt ctcagtacct    300 ttattttaa aaagtaggtg aacattttga gagagaaaag ggcttggttg agatgaagtc     360
cccccccccc cttttttttt ttttagctga aatagatacc ctatgttnaa rgaarggatt    420
attatttacc atgccaytar scacatgctc tttgatgggc nyctccstac cctccttaag    480
```

<210> SEQ ID NO 48
<211> LENGTH: 591
<212> TYPE: DNA
<213> ORGANISM: Homo sapien

<400> SEQUENCE: 48

```
aagagggtac cgagtggaat ttccgcttca ctagtctggt gtggctagtc ggtttcgtgg     60
tggccaacat tacgaacttc caactcaacc gttcttggac gttcaagcgg gagtaccggc    120
gaggatggtg gcgtgaattc tggcctttct ttgccgtggg atcggtagcc gccatcatcg    180
gtatgtttat caagatcttc tttactaacc cgacctctcc gatttacctg cccgagccgt    240
ggtttaacga ggggagggg atccagtcac gcgagtactg gtcccagatc ttcgccatcg    300
tcgtgacaat gcctatcaac ttcgtcgtca ataagttgtg gaccttccga acggtgaagc    360
actccgaaaa cgtccggtgg ctgctgtgcg gtgactccca aaatcttgat aacaacaagg    420
taaccgaatc gcgctaagga accccggcat ctcgggtact ctgcatatgc gtacccctta    480
agccgaattc cagcacactg gcggccgtta ctaattggat ccgaactccg taaccaagcc    540
tgatgcgtaa cttgagttat tctatagtgt ccctaaaata acctggcgtt a             591
```

<210> SEQ ID NO 49
<211> LENGTH: 454
<212> TYPE: DNA
<213> ORGANISM: Homo sapien

<400> SEQUENCE: 49

```
aagagggtac ctgccttgaa atttaaatgt ctaaggaaar tgggagatga ttaagagttg     60
gtgtggcyta gtcacaccaa aatgtattta ttacatcctg ctcctttcta gttgacagga    120
aagaaagctg ctgtgggaa aggagggata aatactgaag ggatttacta aacaaatgtc     180
catcacagag ttttccttttt ttttttttg agacagagtc ttgctctgtc acccaggctg    240
gaatgaagwg gtatgatctc agttgaatgc aacctctacc tcctaggttc aagcgattct    300
catgcctcag cctcctgagc agctgggact ataggcgcat gctaccatgc caggctaatt    360
tttatatttt tattagagac ggggtgttgc catgttggcc aggcaggtct cgaactcctg    420
ggcctcagat gatctgcccc accgtaccct ctta                                454
```

<210> SEQ ID NO 50
<211> LENGTH: 463
<212> TYPE: DNA
<213> ORGANISM: Homo sapien

<400> SEQUENCE: 50

```
aagagggtac caaaaaaaag aaaaaggaaa aaagaaaaa caacttgtat aaggctttct     60
gctgcataca gctttttttt tttaaataaa tggtgccaac aaatgttttt gcattcacac    120
caattgctgg ttttgaaatc gtactcttca aaggtatttg tgcagatcaa tccaatagtg    180
atgccccgta ggttttgtgg actgcccacg ttgtctacct tctcatgtag gagccattga    240
gagactgttt ggacatgcct gtgttcatgt agccgtgatg tccgggggcc gtgtacatca    300
```

| | |
|---|---|
| tgttaccgtg gggtggggtc tgcattggct gctgggcata tggctgggtg cccatcatgc | 360 |
| ccatctgcat ctgcataggg tattgggcg tttgatccat atagccatga ttgctgtggt | 420 |
| agccactgtt catcattggc tgggacatgc tgttaccctc tta | 463 |

<210> SEQ ID NO 51
<211> LENGTH: 399
<212> TYPE: DNA
<213> ORGANISM: Homo sapien

<400> SEQUENCE: 51

| | |
|---|---|
| cttcaacctc ccaaagtgct gggattacag gactgagcca ccacgctcag cctaagcctc | 60 |
| tttttcacta ccctctaagc gatctaccac agtgatgagg ggctaaagag cagtgcaatt | 120 |
| tgattacaat aatggaactt agatttatta attaacaatt tttccttagc atgttggttc | 180 |
| cataattatt aagagtatgg acttacttag aaatgagctt tcattttaag aatttcatct | 240 |
| ttgaccttct ctattagtct gagcagtatg acactatacg tatttatttt aactaaccta | 300 |
| ccttgagcta ttactttta aaaggctata tacatgaatg tgtattgtca actgtaaagc | 360 |
| cccacagtat ttaattatat catgatgtct ttgaggttg | 399 |

<210> SEQ ID NO 52
<211> LENGTH: 392
<212> TYPE: DNA
<213> ORGANISM: Homo sapien

<400> SEQUENCE: 52

| | |
|---|---|
| cttcaacctc aatcaacctt ggtaattgat aaaatcatca cttaactttc tgatataatg | 60 |
| gcaataatta tctgagaaaa aaagtggtg aaagattaaa cttgcatttc tctcagaatc | 120 |
| ttgaaggata tttgaataat tcaaaagcgg aatcagtagt atcagccgaa gaaactcact | 180 |
| tagctagaac gttggaccca tggatctaag tccctgccct tccactaacc agctgattgg | 240 |
| ttttgtgtaa acctcctaca cgcttgggct tggtcgcctc atttgtcaaa gtaaaggctg | 300 |
| aaataggaag ataatgaacc gtgtcttttt ggtctctttt ccatccatta ctctgatttt | 360 |
| acaaagaggc ctgtattccc ctggtgaggt tg | 392 |

<210> SEQ ID NO 53
<211> LENGTH: 179
<212> TYPE: DNA
<213> ORGANISM: Homo sapien
<220> FEATURE:
<221> NAME/KEY: misc_feature
<222> LOCATION: (1)...(179)
<223> OTHER INFORMATION: n = A,T,C or G

<400> SEQUENCE: 53

| | |
|---|---|
| ttcgggtgat gcctcctcag gctacagtga agactggatt acagaaaggt gccagcgaga | 60 |
| tttcagattc ctgtaaacct ctaaagaaaa ggagtcgcgc ctcaactgat gtagaaatga | 120 |
| ctagttcagc atacngagac acntctgact ccgattctag aggactgagt gacctgcan | 179 |

<210> SEQ ID NO 54
<211> LENGTH: 112
<212> TYPE: DNA
<213> ORGANISM: Homo sapien
<220> FEATURE:
<221> NAME/KEY: misc_feature
<222> LOCATION: (1)...(112)
<223> OTHER INFORMATION: n = A,T,C or G

<400> SEQUENCE: 54

```
ttcgggtgat gcctcctcag gctacatcat natagaagca aagtagaana atcnngtttg      60
tgcattttcc cacanacaaa attcaaatga ntggaagaaa ttggganagt at             112
```

<210> SEQ ID NO 55
<211> LENGTH: 225
<212> TYPE: DNA
<213> ORGANISM: Homo sapien

<400> SEQUENCE: 55

```
tgagcttccg cttctgacaa ctcaatagat aatcaaagga caactttaac agggattcac      60
aaaggagtat atccaaatgc aataaaacat ataaaaagga attcagcttc atcatcatca     120
gaagwatgca aattaaaacc ataatgagaa accactatgt cccactagaa tagataaaat     180
cttaaaagac tggtaaaacc aagtgttggt aaggcaagag gagca                    225
```

<210> SEQ ID NO 56
<211> LENGTH: 175
<212> TYPE: DNA
<213> ORGANISM: Homo sapien

<400> SEQUENCE: 56

```
gctcctcttg ccttaccaac acattctcaa aaacctgtta gagtcctaag cattctcctg      60
ttagtattgg gattttaccc ctgtcctata aagatgttat gtaccaaaaa tgaagtggag     120
ggccataccc tgagggaggg gagggatctc tagtgttgtc agaagcggaa gctca          175
```

<210> SEQ ID NO 57
<211> LENGTH: 223
<212> TYPE: DNA
<213> ORGANISM: Homo sapien

<400> SEQUENCE: 57

```
agccatttac cacccatgga tgaatggatt ttgtaattct agctgttgta ttttgtgaat      60
ttgttaattt tgttgttttt ctgtgaaaca catacattgg atatgggagg taaaggagtg     120
tcccagttgc tcctggtcac tccctttata gccattactg tcttgtttct tgtaactcag     180
gttaggtttt ggtctctctt gctccactgc aaaaaaaaaa aaa                      223
```

<210> SEQ ID NO 58
<211> LENGTH: 211
<212> TYPE: DNA
<213> ORGANISM: Homo sapien

<400> SEQUENCE: 58

```
gttcgaaggt gaacgtgtag gtagcggatc tcacaactgg ggaactgtca agacgaatt       60 aactgacttg gatcaatcaa atgtgactga ggaaacacct gaaggtgaag aacatcatcc     120
agtggcagac actgaaaata aggagaatga agttgaagag gtaaagagg agggtccaaa     180 agagatgact ttggatgggt ggtaaatggc t                                    211
```

<210> SEQ ID NO 59
<211> LENGTH: 208
<212> TYPE: DNA
<213> ORGANISM: Homo sapien

<400> SEQUENCE: 59

```
gctcctcttg ccttaccaac tttgcaccca tcatcaacca tgtggccagg tttgcagccc      60
aggctgcaca tcaggggact gcctcgcaat acttcatgct gttgctgctg actgatggtg     120
```

```
ctgtgacgga tgtggaagcc acacgtgagg ctgtggtgcg tgcctcgaac ctgcccatgt      180
cagtgatcat tatgggtggt aaatggct                                        208
```

<210> SEQ ID NO 60
<211> LENGTH: 171
<212> TYPE: DNA
<213> ORGANISM: Homo sapien

<400> SEQUENCE: 60

```
agccatttac cacccatact aaattctagt tcaaactcca acttcttcca taaaacatct      60
aaccactgac accagttggc aatagcttct tccttcttta acctcttaga gtatttatgg     120
tcaatgccac acatttctgc aactgaataa agttggtaag caagaggag c               171
```

<210> SEQ ID NO 61
<211> LENGTH: 134
<212> TYPE: DNA
<213> ORGANISM: Homo sapien
<220> FEATURE:
<221> NAME/KEY: misc_feature
<222> LOCATION: (1)...(134)
<223> OTHER INFORMATION: n = A,T,C or G

<400> SEQUENCE: 61

```
cgggtgatgc ctcctcaggc tttggtgtgt ccactcnact cactggcctc ttctccagca      60
actggtgaan atgtcctcan gaaaancncc acacgcngct cagggtgggg tgggaancat     120
canaatcatc nggc                                                      134
```

<210> SEQ ID NO 62
<211> LENGTH: 145
<212> TYPE: DNA
<213> ORGANISM: Homo sapien

<400> SEQUENCE: 62

```
agagggtaca tatgcaacag tatataaagg aagaagtgca ctgagaggaa cttcatcaag      60
gccatttaat caataagtga tagagtcaag gctcaaccca ggtgtgacgg attccaggtc     120
ccaagctcct tactggtacc ctctt                                          145
```

<210> SEQ ID NO 63
<211> LENGTH: 297
<212> TYPE: DNA
<213> ORGANISM: Homo sapien

<400> SEQUENCE: 63

```
tgcactgaga ggaattcaaa gggtttatgc caaagaacaa accagtcctc tgcagcctaa      60
ctcatttgtt tttgggctgc gaagccatgt agagggcgat caggcagtag atggtccctc     120
ccacagtcag cgccatggtg gtccggtaaa gcatttggtc aggcaggcct cgtttcaggt     180
agacgggcac acatcagctt tctggaaaaa cttttgtagc tctggagctt tgttttttccc    240 agcataatca tacactgtgg aatcggaggt cagtttagtt ggtaaggcaa gaggagc        297
```

<210> SEQ ID NO 64
<211> LENGTH: 300
<212> TYPE: DNA
<213> ORGANISM: Homo sapien

<400> SEQUENCE: 64

```
gcactgagag gaacttccaa tactatgttg aataggagtg gtgagagagg gcatccttgt      60
cttgtgccgg ttttcaaagg gaatgcttcc agcttttgcc cattcagtat aatattaaag     120
```

```
aatgttttac catttctgtg cttgcctgtt tttctgtgtt tttgttggtc tcttcattct      180 ccattttag gcctttacat gttaggaata tatttctttt aatgatactt cacctttggt       240
atcttttgtg agactctact catagtgtga taagcactgg gttggtaagg caagaggagc      300

<210> SEQ ID NO 65
<211> LENGTH: 203
<212> TYPE: DNA
<213> ORGANISM: Homo sapien

<400> SEQUENCE: 65
gctcctcttg ccttaccaac tcacccagta tgtcagcaat tttatcrgct ttacctacga      60
aacagcctgt atccaaacac ttaacacact cacctgaaaa gttcaggcaa caatcgcctt     120
ctcatgggtc tctctgctcc agttctgaac ctttctcttt cctagaaca tgcatttarg      180 tcgatagaag ttcctctcag tgc                                             203

<210> SEQ ID NO 66
<211> LENGTH: 344
<212> TYPE: DNA
<213> ORGANISM: Homo sapien

<400> SEQUENCE: 66
tacggggacc cctgcattga gaaagcgaga ctcactctga agctgaaatg ctgttgccct      60
tgcagtgctg gtagcaggag ttctgtgctt tgtgggctaa ggctcctgga tgaccctga     120 catggagaag gcagagttgt gtgccccttc tcatggcctc gtcaaggcat catggactgc    180
cacacacaaa atgccgtttt tattaacgac atgaaattga aggagagaac acaattcact    240
gatgtggctc gtaaccatgg atatggtcac atacagaggt gtgattatgt aaaggttaat    300
tccacccacc tcatgtggaa actagcctca atgcaggggt ccca                     344

<210> SEQ ID NO 67
<211> LENGTH: 157
<212> TYPE: DNA
<213> ORGANISM: Homo sapien

<400> SEQUENCE: 67
gcactgagag gaacttcgta gggaggttga actggctgct gaggaggggg aacaacaggg     60
taaccagact gatagccatt ggatggataa tatggtggtt gaggagggac actacttata   120
gcagagggtt gtgtatagcc tgaggaggca tcacccg                              157

<210> SEQ ID NO 68
<211> LENGTH: 137
<212> TYPE: DNA
<213> ORGANISM: Homo sapien

<400> SEQUENCE: 68
gcactgagag gaacttctag aaagtgaaag tctagacata aataaaata aaatttaaa       60 actcaggaga gacagcccag cacggtggct cacgcctgta atcccagaac tttgggagcc   120
tgaggaggca tcacccg                                                    137

<210> SEQ ID NO 69
<211> LENGTH: 137
<212> TYPE: DNA
<213> ORGANISM: Homo sapien

<400> SEQUENCE: 69
```
cgggtgatgc ctcctcaggc tgtatttga agactatcga ctggacttct tatcaactga    60
agaatccgtt aaaaatacca gttgtattat ttctacctgt caaaatccat ttcaaatgtt   120
gaagttcctc tcagtgc                                                  137

<210> SEQ ID NO 70
<211> LENGTH: 220
<212> TYPE: DNA
<213> ORGANISM: Homo sapien
<220> FEATURE:
<221> NAME/KEY: misc_feature
<222> LOCATION: (1)...(220)
<223> OTHER INFORMATION: n = A,T,C or G

<400> SEQUENCE: 70
agcatgttga gcccagacac gcaatctgaa tgagtgtgca cctcaagtaa atgtctacac    60
gctgcctggt ctgacatggc accatcnc gtggagggca casctctgct cngcctacwa    120
cgagggcant ctcatwgaca ggttccaccc accaaactgc aagaggctca nnaagtactr   180
ccagggtmya sggacmasgg tgggaytyca ycacwcatct                         220

<210> SEQ ID NO 71
<211> LENGTH: 353
<212> TYPE: DNA
<213> ORGANISM: Homo sapien
<220> FEATURE:
<221> NAME/KEY: misc_feature
<222> LOCATION: (1)...(353)
<223> OTHER INFORMATION: n = A,T,C or G

<400> SEQUENCE: 71
cgttagggtc tctatccact gctaaaccat acacctgggt aaacagggac catttaacat    60
tcccanctaa atatgccaag tgacttcaca tgtttatctt aaagatgtcc aaaacgcaac   120
tgattttctc ccctaaacct gtgatggtgg gatgattaan cctgagtggt ctacagcaag   180
ttaagtgcaa ggtgctaaat gaangtgacc tgagatacag catctacaag gcagtacctc   240
tcaacncagg gcaactttgc ttctcanagg gcatttagca gtgtctgaag taatttctgt   300
attacaactc acggggcggg gggtgaatat ctantggana gnagaccta acg           353

<210> SEQ ID NO 72
<211> LENGTH: 343
<212> TYPE: DNA
<213> ORGANISM: Homo sapien

<400> SEQUENCE: 72
gcactgagag gaacttccaa tacyatkatc agagtgaaca rgcarccyac agaacaggag    60
aaaatgttyg caatctctcc atctgacaaa aggctaatat ccagawtcta awggaacctt   120
aaacaaattt atgagaaaag aacaracaac ctcawcaaaa agtgggtgaa ggawatgcts   180
aaargaagac atytattcag ccagtaaaca yatgaaaaaa aggctcatsa tcactgawca   240
ttagagaaat gcaaatcaaa accacaatga gataccatct yayrccagtt agaayggtga   300
tcattaaaar stcaggaaac aacagatgct ggacaaggtg tca                    343

<210> SEQ ID NO 73
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 73

```
gcactgagag gaacttcaga gagagagaga gagttccacc ctgtacttgg ggagagaaac      60
agaaggtgag aaagtctttg gttctgaagc agcttctaag atcttttcat ttgcttcatt     120
tcaaagttcc catgctgcca aagtgccatc ctttgggta ctgttttctg agctccagtg     180
ataactcatt tatacaaggg agatacccag aaaaaaagtg agcaaatctt aaaaggtgg     240
cttgagttca gccttaaata ccatcttgaa atgacacaga gaagaanga tgttgggtgg     300
gagtggatag agaccctaac g                                              321
```

<210> SEQ ID NO 74
<211> LENGTH: 321
<212> TYPE: DNA
<213> ORGANISM: Homo sapien

<400> SEQUENCE: 74

```
gcactgagag gaacttcaga gagagagaga gagttccacc ctgtacttgg ggagagaaac      60
agaaggtgag aaagtctttg gttctgaagc agcttctaag atcttttcat ttgcttcatt     120
tcaaagttcc catgctgcca aagtgccatc ctttgggta ctgttttctg agctccagtg     180
ataactcatt tatacaaggg agatacccag aaaaaaagtg agcaaatctt aaaaggtgg     240
cttgagttca gycttaaata ccatcttgaa atgamacaga gaagaagga tgttgggtgg     300
gagtggatag agaccctaac g                                              321
```

<210> SEQ ID NO 75
<211> LENGTH: 317
<212> TYPE: DNA
<213> ORGANISM: Homo sapien

<400> SEQUENCE: 75

```
gcactgagag gaacttccac atgcactgag aaatgcatgt tcacaaggac tgaagtctgg      60
aactcagttt ctcagttcca atcctgattc aggtgtttac cagctacaca accttaagca     120
agtcagataa ccttagcttc ctcatatgca aaatgagaat gaaaagtact catcgctgaa     180
ttgttttgag gattagaaaa acatctggca tgcagtagaa attcaattag tattcatttt     240
cattcttcta aattaaacaa ataggatttt tagtggtgga acttcagaca ccagaaatgg     300
gagtggatag agaccct                                                   317
```

<210> SEQ ID NO 76
<211> LENGTH: 244
<212> TYPE: DNA
<213> ORGANISM: Homo sapien

<400> SEQUENCE: 76

```
cgttagggtc tctatccact cccactactg atcaaactct atttatttaa ttattttat       60
catactttaa gttctgggat acacgtgcag catgcgcagg tttgttgcat aggtatacac     120
ttgccatggt ggtttgctgc acccatcagt ccatcatcta cattaggtat ttctcctaat     180
gctatccctc ccctagcccc ttacaccccc aacaggctct agtgtgtgaa gttcctctca     240
gtgc                                                                 244
```

<210> SEQ ID NO 77
<211> LENGTH: 254
<212> TYPE: DNA
<213> ORGANISM: Homo sapien

<400> SEQUENCE: 77

```
cgttagggtc tctatccact gaaatctgaa gcacaggagg aagagaagca gtyctagtga      60
gatggcaagt tcwtttacca cactctttaa catttygttt agttttaacc tttatttatg     120
gataataaag gttaatatta ataatgattt attttaaggc attcccraat ttgcataatt     180
ctccttttgg agatacccctt ttatctccag tgcaagtctg gatcaaagtg atasamagaa    240
gttcctctca gtgc                                                       254
```

<210> SEQ ID NO 78
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 78

```
ttcgatacag gcaaacatga actgcaggag ggtggtgacg atcatgatgt tgccgatggt      60
ccggatggnc acgaagacgc actggancac gtgcttacgt cctttgtctc tgttgatggc    120
cctgagggga cgcaggaccc ttatgaccct cagaatcttc acaacgggag atggcactgg    180
attgantccc antgacacca gagacacccc aaccaccagn atatcantat attgatgtag    240
ttcctgtaga nggcccccctt gtggaggaaa gctccatnag ttggtcatct tcaacaggat    300
ctcaacagtt tccgatggct gtgatgggca tagtcatant taaccntgtn tcgaa          355
```

<210> SEQ ID NO 79
<211> LENGTH: 406
<212> TYPE: DNA
<213> ORGANISM: Homo sapien

<400> SEQUENCE: 79

```
taagagggta ccagcagaaa ggttagtatc atcagatagc atcttatacg agtaatatgc      60
ctgctatttg aagtgtaatt gagaaggaaa attttagcgt gctcactgac ctgcctgtag    120
ccccagtgac agctaggatg tgcattctcc agccatcaag agactgagtc aagttgttcc    180
ttaagtcaga acagcagact cagctctgac attctgattc gaatgacact gttcaggaat    240
cggaatcctg tcgattagac tggacagctt gtggcaagtg aatttgcctg taacaagcca    300
gatttttaa aatttatatt gtaaataatg tgtgtgtgtg tgtgtgtata tatatatata    360
tgtacagtta tctaagttaa tttaaaagtt gtttggtacc ctctta                     406
```

<210> SEQ ID NO 80
<211> LENGTH: 327
<212> TYPE: DNA
<213> ORGANISM: Homo sapien

<400> SEQUENCE: 80

```
tttttttttt tttactcggc tcagtctaat ccttttgta gtcactcata ggccagactt       60
agggctagga tgatgattaa taagagggat gacataacta ttagtggcag gttagttgtt    120
tgtagggctc atggtagggg taaaggagg gcaatttcta gatcaaataa taagaaggta    180
atagctacta agaagaattt tatggagaaa gggacgcggg cggggatat agggtcgaag    240
ccgcactcgt aagggtgga ttttctatg tagccgttga gttgtggtag tcaaaatgta    300
ataattatta gtagtaagcc taggaga                                        327
```

<210> SEQ ID NO 81
<211> LENGTH: 318
<212> TYPE: DNA
<213> ORGANISM: Homo sapien

<400> SEQUENCE: 81

| | |
|---|---|
| tagtctatgc ggttgattcg gcaatccatt atttgctgga ttttgtcatg tgttttgcca | 60 |
| attgcattca taatttatta tgcatttatg cttgtatctc ctaagtcatg gtatataatc | 120 |
| catgctttt atgttttgtc tgacataaac tcttatcaga gccctttgca cacagggatt | 180 |
| cataaatat taacacagtc tacatttatt tggtgaatat tgcatatctg ctgtactgaa | 240 |
| agcacattaa gtaacaaagg caagtgagaa gaatgaaaag cactactcac aacagttatc | 300 |
| atgattgcgc atagacta | 318 |

<210> SEQ ID NO 82
<211> LENGTH: 338
<212> TYPE: DNA
<213> ORGANISM: Homo sapien

<400> SEQUENCE: 82

| | |
|---|---|
| tcttcaacct ctactcccac taatagcttt ttgatgactt ctagcaagcc tcgctaacct | 60 |
| cgccttaccc cccactatta acctactggg agaactctct gtgctagtaa ccacgttctc | 120 |
| ctgatcaaat atcactctcc tacttacagg actcaacata ctagtcacag ccctatactc | 180 |
| cctctacata tttaccacaa cacaatgggg ctcactcacc caccacatta acaacataaa | 240 |
| accctcattc acacgagaaa acaccctcat gttcatacac ctatccccca ttctcctcct | 300 |
| atccctcaac ccgacatca ttaccgggtt ttcctctt | 338 |

<210> SEQ ID NO 83
<211> LENGTH: 111
<212> TYPE: DNA
<213> ORGANISM: Homo sapien

<400> SEQUENCE: 83

| | |
|---|---|
| agccatttac cacccatcca caaaaaaaaa aaaaaaaag aaaatatca aggaataaaa | 60 |
| atagactttg aacaaaaagg aacatttgct ggcctgagga ggcatcaccc g | 111 |

<210> SEQ ID NO 84
<211> LENGTH: 224
<212> TYPE: DNA
<213> ORGANISM: Homo sapien

<400> SEQUENCE: 84

| | |
|---|---|
| tcgggtgatg cctcctcagg ccaagaagat aaagcttcag accccctaaca catttccaaa | 60 |
| aaggaagaaa ggagaaaaaa gggcatcatc cccgttccga agggtcaggg aggaggaaat | 120 |
| tgaggtggat tcacgagttg cggacaactc ctttgatgcc aagcgaggtg cagccggaga | 180 |
| ctggggagag cgagccaatc aggttttgaa gttcctctca gtgc | 224 |

<210> SEQ ID NO 85
<211> LENGTH: 348
<212> TYPE: DNA
<213> ORGANISM: Homo sapien

<400> SEQUENCE: 85

| | |
|---|---|
| gcactgagag gaacttcgtt ggaaacgggt tttttcatg taaggctaga cagaagaatt | 60 |
| ctcagtaact tccttgtgtt gtgtgtattc aactcacasa gttgaacgat cctttacaca | 120 |

```
gagcagactt gtaacactct twttgtggaa tttgcaagtg gagatttcag scgctttgaa      180
gtsaaaggta gaaaaggaaa tatcttccta taaaaactag acagaatgat tctcagaaac     240
tcctttgtga tgtgtgcgtt caactcacag agtttaacct ttcwtttcat agaagcagtt     300
aggaaacact ctgtttgtaa agtctgcaag tggatagaga ccctaacg                  348
```

<210> SEQ ID NO 86
<211> LENGTH: 293
<212> TYPE: DNA
<213> ORGANISM: Homo sapien

<400> SEQUENCE: 86

```
gcactgagag gaacttcytt gtgwtgtktg yattcaactc acagagttga asswtsmttt      60
acabagwkca ggcttkcaaa cactctttt gtmgaatytg caagwggaka tttsrrccrc      120
tttgwggycw wysktmgaaw mggrwatatc ttcwyatmra amctagacag aaksattctc     180
akaawstyyy ytgtgawgws tgcrttcaac tcacagagkt kaacmwtyct kytsatrgag     240
cagttwkgaa actctmtttc tttggattct gcaagtggat agagacccta acg            293
```

<210> SEQ ID NO 87
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 87

```
ctcctaggct                                                             10
```

<210> SEQ ID NO 88
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 88

```
agtagttgcc                                                             10
```

<210> SEQ ID NO 89
<211> LENGTH: 11
<212> TYPE: DNA
<213> ORGANISM: Artificial Sequence
<220> FEATURE:
<223> OTHER INFORMATION: Primer for amplification from breast tumor cDNA

<400> SEQUENCE: 89

```
ttccgttatg c                                                           11
```

<210> SEQ ID NO 90
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 90

```
tggtaaaggg                                                             10
```

<210> SEQ ID NO 91
<211> LENGTH: 10
<212> TYPE: DNA
<213> ORGANISM: Artificial Sequence

```
<220> FEATURE:
<223> OTHER INFORMATION: Primer for amplification from breast tumor cDNA

<400> SEQUENCE: 91
tcggtcatag                                                          10

<210> SEQ ID NO 92
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 92
tacaacgagg                                                          10

<210> SEQ ID NO 93
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 93
tggattggtc                                                          10

<210> SEQ ID NO 94
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 94
ctttctaccc                                                          10

<210> SEQ ID NO 95
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 95
ttttggctcc                                                          10

<210> SEQ ID NO 96
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 96
ggaaccaatc                                                          10

<210> SEQ ID NO 97
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 97
tcgatacagg                                                          10
```

<210> SEQ ID NO 98
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 98
ggtactaagg                                                              10

<210> SEQ ID NO 99
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 99
agtctatgcg                                                              10

<210> SEQ ID NO 100
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 100
ctatccatgg                                                              10

<210> SEQ ID NO 101
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 101
tctgtccaca                                                              10

<210> SEQ ID NO 102
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 102
aagagggtac                                                              10

<210> SEQ ID NO 103
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 103
cttcaacctc                                                              10

<210> SEQ ID NO 104
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 104
gctcctcttg ccttaccaac                                              20

<210> SEQ ID NO 105
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 105
gtaagtcgag cagtgtgatg                                              20

<210> SEQ ID NO 106
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 106
gtaagtcgag cagtctgatg                                              20

<210> SEQ ID NO 107
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 107
gacttagtgg aaagaatgta                                              20

<210> SEQ ID NO 108
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 108
gtaattccgc caaccgtagt                                              20

<210> SEQ ID NO 109
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 109
atggttgatc gatagtggaa                                              20

<210> SEQ ID NO 110
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 110
acggggaccc ctgcattgag                                              20

<210> SEQ ID NO 111

<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 111
tattctagac cattcgctac                                               20

<210> SEQ ID NO 112
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 112
acataaccac tttagcgttc                                               20

<210> SEQ ID NO 113
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 113
cgggtgatgc ctcctcaggc                                               20

<210> SEQ ID NO 114
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 114
agcatgttga gcccagacac                                               20

<210> SEQ ID NO 115
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 115
gacaccttgt ccagcatctg                                               20

<210> SEQ ID NO 116
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 116
tacgctgcaa cactgtggag                                               20

<210> SEQ ID NO 117
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 117
cgttagggtc tctatccact                                           20

<210> SEQ ID NO 118
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 118
agactgactc atgtccccta                                           20

<210> SEQ ID NO 119
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 119
tcatcgctcg gtgactcaag                                           20

<210> SEQ ID NO 120
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 120
caagattcca taggctgacc                                           20

<210> SEQ ID NO 121
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 121
acgtactggt cttgaaggtc                                           20

<210> SEQ ID NO 122
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 122
gacgcttggc cacttgacac                                           20

<210> SEQ ID NO 123
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 123
gtatcgacgt agtggtctcc                                           20

<210> SEQ ID NO 124
<211> LENGTH: 20
<212> TYPE: DNA

```
<213> ORGANISM: Artificial Sequence
<220> FEATURE:
<223> OTHER INFORMATION: Primer for amplification from breast tumor cDNA

<400> SEQUENCE: 124
tagtgacatt acgacgctgg                                                    20

<210> SEQ ID NO 125
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 125
cgggtgatgc ctcctcaggc                                                    20

<210> SEQ ID NO 126
<211> LENGTH: 23
<212> TYPE: DNA
<213> ORGANISM: Artificial Sequence
<220> FEATURE:
<223> OTHER INFORMATION: Primer for amplification from breast tumor cDNA

<400> SEQUENCE: 126
atggctattt tcggggctg aca                                                 23

<210> SEQ ID NO 127
<211> LENGTH: 22
<212> TYPE: DNA
<213> ORGANISM: Artificial Sequence
<220> FEATURE:
<223> OTHER INFORMATION: Primer for amplification from breast tumor cDNA

<400> SEQUENCE: 127
ccggtatctc ctcgtgggta tt                                                 22

<210> SEQ ID NO 128
<211> LENGTH: 18
<212> TYPE: DNA
<213> ORGANISM: Artificial Sequence
<220> FEATURE:
<223> OTHER INFORMATION: Primer for amplification from breast tumor cDNA

<400> SEQUENCE: 128
ctgcctgagc cacaaatg                                                      18

<210> SEQ ID NO 129
<211> LENGTH: 24
<212> TYPE: DNA
<213> ORGANISM: Artificial Sequence
<220> FEATURE:
<223> OTHER INFORMATION: Primer for amplification from breast tumor cDNA

<400> SEQUENCE: 129
ccggaggagg aagctagagg aata                                               24

<210> SEQ ID NO 130
<211> LENGTH: 14
<212> TYPE: DNA
<213> ORGANISM: Artificial Sequence
<220> FEATURE:
<223> OTHER INFORMATION: Primer

<400> SEQUENCE: 130
tttttttttt ttag                                                          14
```

```
<210> SEQ ID NO 131
<211> LENGTH: 18
<212> TYPE: PRT
<213> ORGANISM: Artificial Sequence
<220> FEATURE:
<223> OTHER INFORMATION: Predicited Th Motifs (B-cell epitopes)

<400> SEQUENCE: 131

Ser Ser Gly Gly Arg Thr Phe Asp Asp Phe His Arg Tyr Leu Leu Val
 1               5                  10                  15

Gly Ile

<210> SEQ ID NO 132
<211> LENGTH: 22
<212> TYPE: PRT
<213> ORGANISM: Artificial Sequence
<220> FEATURE:
<223> OTHER INFORMATION: Predicted Th Motifs (B-cell epitopes)
<221> NAME/KEY: VARIANT
<222> LOCATION: (1)...(22)
<223> OTHER INFORMATION: Xaa = Any Amino Acid

<400> SEQUENCE: 132

Gln Gly Ala Ala Gln Lys Pro Ile Asn Leu Ser Lys Xaa Ile Glu Val
 1               5                  10                  15

Val Gln Gly His Asp Glu
            20

<210> SEQ ID NO 133
<211> LENGTH: 23
<212> TYPE: PRT
<213> ORGANISM: Artificial Sequence
<220> FEATURE:
<223> OTHER INFORMATION: Predicted Th Motifs (B-cell epitopes)

<400> SEQUENCE: 133

Ser Pro Gly Val Phe Leu Glu His Leu Gln Glu Ala Tyr Arg Ile Tyr
 1               5                  10                  15

Thr Pro Phe Asp Leu Ser Ala
            20

<210> SEQ ID NO 134
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 134

Tyr Leu Leu Val Gly Ile Gln Gly Ala
 1               5

<210> SEQ ID NO 135
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 135

Gly Ala Ala Gln Lys Pro Ile Asn Leu
 1               5

<210> SEQ ID NO 136
```

-continued

```
<211> LENGTH: 9
<212> TYPE: PRT
<213> ORGANISM: Artificial Sequence
<220> FEATURE:
<223> OTHER INFORMATION: Predicited HLA A2.1 Motifs (T-cell epitopes)
<221> NAME/KEY: VARIANT
<222> LOCATION: (1)...(9)
<223> OTHER INFORMATION: Xaa = Any Amino Acid

<400> SEQUENCE: 136

Asn Leu Ser Lys Xaa Ile Glu Val Val
 1               5

<210> SEQ ID NO 137
<211> LENGTH: 9
<212> TYPE: PRT
<213> ORGANISM: Artificial Sequence
<220> FEATURE:
<223> OTHER INFORMATION: Predicited HLA A2.1 Motifs (T-cell epitopes)

<400> SEQUENCE: 137

Glu Val Val Gln Gly His Asp Glu Ser
 1               5

<210> SEQ ID NO 138
<211> LENGTH: 9
<212> TYPE: PRT
<213> ORGANISM: Artificial Sequence
<220> FEATURE:
<223> OTHER INFORMATION: Predicited HLA A2.1 Motifs (T-cell epitopes)

<400> SEQUENCE: 138

His Leu Gln Glu Ala Tyr Arg Ile Tyr
 1               5

<210> SEQ ID NO 139
<211> LENGTH: 9
<212> TYPE: PRT
<213> ORGANISM: Artificial Sequence
<220> FEATURE:
<223> OTHER INFORMATION: Predicited HLA A2.1 Motifs (T-cell epitopes)

<400> SEQUENCE: 139

Asn Leu Ala Phe Val Ala Gln Ala Ala
 1               5

<210> SEQ ID NO 140
<211> LENGTH: 9
<212> TYPE: PRT
<213> ORGANISM: Artificial Sequence
<220> FEATURE:
<223> OTHER INFORMATION: Predicited HLA A2.1 Motifs (T-cell epitopes)

<400> SEQUENCE: 140

Phe Val Ala Gln Ala Ala Pro Asp Ser
 1               5

<210> SEQ ID NO 141
<211> LENGTH: 9388
<212> TYPE: DNA
<213> ORGANISM: Homo sapien

<400> SEQUENCE: 141
gctcgcggcc gcgagctcaa ttaaccctca ctaaagggag tcgactcgat cagactgtta      60
ctgtgtctat gtagaaagaa gtagacataa gagattccat tttgttctgt actaagaaaa     120
attcttctgc cttgagatgc tgttaatctg taacccctagc cccaaccctg tgctcacaga    180
```

-continued

```
gacatgtgct gtgttgactc aaggttcaat ggatttaggg ctatgctttg ttaaaaagt      240 gcttgaagat aatatgcttg ttaaaagtca tcaccattct ctaatctcaa gtacccaggg     300
acacaataca ctgcggaagg ccgcagggac ctctgtctag gaaagccagg tattgtccaa     360
gatttctccc catgtgatag cctgagatat ggcctcatgg gaagggtaag acctgactgt     420
cccccagccc gacatccccc agcccgacat cccccagccc gacacccgaa aagggtctgt     480
gctgaggagg attagtaaaa gaggaaggcc tctttgcagt tgaggtaaga ggaaggcatc     540
tgtctcctgc tcgtccctgg gcaatagaat gtcttggtgt aaaacccgat tgtatgttct     600
acttactgag ataggagaaa acatccttag ggctggaggt gagacacgct ggcggcaata     660
ctgctcttta atgcaccgag atgtttgtat aagtgcacat caaggcacag cacctttcct     720
taaacttatt tatgacacag agacctttgt tcacgttttc ctgctgaccc tctccccact     780
attaccctat tggcctgcca catcccctc tccgagatgg tagagataat gatcaataaa     840
tactgaggga actcagagac cagtgtccct gtaggtcctc cgtgtgctga gcgccggtcc     900
cttgggctca cttttctttc tctatacttt gtctctgtgt ctctttcttt tctcagtctc     960
tcgttccacc tgacgagaaa tacccacagg tgtggagggg caggccaccc cttcaataat    1020
ttactagcct gttcgctgac aacaagactg gtggtgcaga aggttgggtc ttggtgttca    1080
ccgggtggca ggcatgggcc aggtgggagg gtctccagcg cctggtgcaa atctccaaga    1140
aagtgcagga aacagcacca aggtgattg taaattttga tttggcgcgg caggtagcca    1200
ttccagcgca aaaatgcgca ggaaagcttt tgctgtgctt gtaggcaggt aggccccaag    1260
cacttcttat tggctaatgt ggagggaacc tgcacatcca ttggctgaaa tctccgtcta    1320
tttgaggctg actgagcgcg ttcctttctt ctgtgttgcc tggaaacgga ctgtctgcct    1380
agtaacatct gatcacgttt cccattggcc gccgtttccg gaagcccgcc ctcccatttc    1440
cggaagcctg gcgcaaggtt ggtctgcagg tggcctccag gtgcaaagtg ggaagtgtga    1500
gtcctcagtc ttgggctatt cggccacgtg cctgccggac atgggacgct ggagggtcag    1560
cagcgtggag tcctggcctt ttgcgtccac gggtgggaaa ttggccattg ccacggcggg    1620
aactgggact caggctgccc cccggccgtt tctcatccgt ccaccggact cgtgggcgct    1680
cgcactggcg ctgatgtagt ttcctgacct ctgacccgta ttgtctccag attaaaggta    1740 aaaacgggc ttttcagcc cactcgggta aaacgccttt tgatttctag gcaggtgttt     1800
tgttgcacgc ctgggaggga gtgacccgca ggttgaggtt tattaaaata cattcctggt    1860
ttatgttatg tttataataa agcaccccaa cctttacaaa atctcacttt ttgccagttg    1920
tattatttag tggactgtct ctgataagga cagccagtta aaatgaatt ttgttgttgc     1980 taattaaacc aatttttagt tttggtgttt gtcctaatag caacaacttc tcaggcttta    2040
taaaaccata tttcttgggg gaaatttctg tgtaaggcac agcgagttag tttggaattg    2100
ttttaaagga agtaagttcc tggttttgat atcttagtag tgtaatgccc aacctggttt    2160
ttactaaccc tgttttttaga ctctccctt ccttaaatca cctagccttg tttccacctg    2220
aattgactct cccttagcta agagcgccag atggactcca tcttggctct ttcactggca    2280 gcccctttcct caaggactta acttgtgcaa gctgactccc agcacatcca agaatgcaat    2340
taactgttaa gatactgtgg caagctatat ccgcagttcc gaggaattca tccgattgat    2400
tatgcccaaa agccccgcgt ctatcacctt gtaataatct taaagcccct gcacctgaaa    2460
ctattaactt tcctgtaacc atttatcctt ttaactttt tgcttacttt atttctgtaa     2520
```

```
aattgtttta actagacctc ccctcccctt tctaaaccaa agtataaaag aagatctagc    2580
cccttcttca gagcggagag aattttgagc attagccatc tcttggcggc cagctaaata    2640
aatggacttt taatttgtct caaagtgtgg cgttttctct aactcgctca ggtacgacat    2700
ttggaggccc cagcgagaaa cgtcaccggg agaaacgtca ccgggcgaga gccgggcccg    2760
ctgtgtgctc ccccggaagg acagccagct tgtaggggg agtgccacct gaaaaaaaaa    2820
tttccaggtc cccaaagggt gaccgtcttc cggaggacag cggatcgact accatgcggg    2880
tgcccaccaa aattccacct ctgagtcctc aactgctgac cccggggtca ggtaggtcag    2940
atttgacttt ggttctggca gagggaagcg accctgatga gggtgtccct cttttgactc    3000
tgcccatttc tctaggatgc tagagggtag agccctggtt ttctgttaga cgcctctgtg    3060
tctctgtctg ggagggaagt ggccctgaca ggggccatcc cttgagtcag tccacatccc    3120
aggatgctgg gggactgagt cctggtttct ggcagactgg tctctctctc tctcttttc     3180 tatctctaat cttccttgt tcaggtttct tggagaatct ctgggaaaga aaaagaaaa     3240 actgttataa actctgtgtg aatggtgaat gaatggggga ggacaagggc ttgcgcttgt    3300
cctccagttt gtagctccac ggcgaaagct acggagttca agtgggccct cacctgcggt    3360
tccgtggcga cctcataagg cttaaggcag catccggcat agctcgatcc gagccggggg    3420
tttataccgg cctgtcaatg ctaagaggag cccaagtccc ctaaggggga gcggccaggc    3480
gggcatctga ctgatcccat cacgggaccc cctccccttg tttgtctaaa aaaaaaaaa    3540 gaagaaactg tcataactgt ttacatgccc tagggtcaac tgtttgtttt atgtttattg    3600
ttctgttcgg tgtctattgt cttgtttagt ggttgtcaag gttttgcatg tcaggacgtc    3660
gatattgccc aagacgtctg ggtaagaact tctgcaaggt ccttagtgct gattttttgt    3720
cacaggaggt taaatttctc atcaatcatt taggctggcc accacagtcc tgtcttttct    3780
gccagaagca agtcaggtgt tgttacggga atgagtgtaa aaaaacattc gcctgattgg    3840
gatttctggc accatgatgg ttgtatttag attgtcatac cccacatcca ggttgattgg    3900
acctcctcta aactaaactg gtggtgggtt caaaacagcc accctgcaga tttccttgct    3960
cacctctttg gtcattctgt aacttttcct gtgcccttaa atagcacact gtgtagggaa    4020
acctaccctc gtactgcttt acttcgttta gattcttact ctgttcctct gtggctactc    4080
tcccatctta aaaacgatcc aagtggtcct tttcctcctc cctgccccct accccacaca    4140
tctcgttttc cagtgcgaca gcaagttcag cgtctccagg acttggctct gctctcactc    4200
cttgaaccct taaaagaaaa agctgggttt gagctatttg cctttgagtc atggagacac    4260
aaaaggtatt tagggtacag atctagaaga agagagagaa cacctagatc caactgaccc    4320
aggagatctc gggctggcct ctagtcctcc tccctcaatc ttaaagctac agtgatgtgg    4380
caagtggtat ttagctgttg tggttttttct gctctttctg gtcatgttga ttctgttctt    4440
tcgatactcc agcccccag ggagtgagtt tctctgtctg tgctgggttt gatatctatg    4500
ttcaaatctt attaaattgc ttcaaaaaa aaaaaaaaa gggaaacact tcctcccagc     4560
cttgtaaggg ttggagccct ctccagtata tgctgcagaa ttttctctc ggtttctcag     4620 aggattatgg agtccgcctt aaaaaaggca agctctggac actctgcaaa gtagaatggc    4680
caaagtttgg agttgagtgg ccccttgaag ggtcactgaa cctcacaatt gttcaagctg    4740
tgtggcgggt tgttactgaa actcccggcc tccctgatca gtttcccctac attgatcaat   4800 ggctgagttt ggtcaggagc accccttcca tggctccact catgcaccat tcataatttt    4860
acctccaagg tcctcctgag ccagaccgtg ttttcgcctc gaccctcagc cggttcagct    4920
```

```
cgccctgtac tgcctctctc tgaagaagag gagagtctcc ctcacccagt cccaccgcct    4980
taaaaccagc ctactccctt agggtcatcc catgtctcct cggctatgtc ccctgtaggc    5040
tcatcaccca ttgcctcttg gttgcaaccg tggtgggagg aagtagcccc tctactacca    5100
ctgagagagg cacaagtccc tctgggtgat gagtgctcca ccccttcct ggtttatgtc     5160 ccttctttct acttctgact tgtataattg gaaaacccat aatcctccct tctctgaaaa    5220
gccccaggct ttgacctcac tgatggagtc tgtactctgg acacattggc ccacctggga    5280
tgactgtcaa cagctccttt tgaccctttt cacctctgaa gagagggaaa gtatccaaag    5340
agaggccaaa aagtacaacc tcacatcaac caataggccg gaggaggaag ctagaggaat    5400
agtgattaga gacccaattg ggacctaatt gggacccaaa tttctcaagt ggagggagaa    5460
cttttgacga tttccaccgg tatctcctcg tgggtattca gggagctgct cagaaaccta    5520
taaacttgtc taaggcgact gaagtcgtcc aggggcatga tgagtcacca ggagtgtttt    5580
tagagcacct ccaggaggct tatcggattt acaccccttt tgacctggca gccccgaaa    5640 atagccatgc tcttaatttg gcatttgtgg ctcaggcagc cccagatagt aaaggaaac    5700 tccaaaaact agagggattt tgctggaatg aataccagtc agcttttaga gatagcctaa    5760
aaggtttttg acagtcaaga ggttgaaaaa caaaaacaag cagctcaggc agctgaaaaa    5820
agccactgat aaagcatcct ggagtatcag agtttactgt tagatcagcc tcatttgact    5880
tcccctccca catggtgttt aaatccagct acactacttc ctgactcaaa ctccactatt    5940
cctgttcatg actgtcagga actgttggaa actactgaaa ctggccgacc tgatcttcaa    6000
aatgtgcccc taggaaaggt ggatgccacc gtgttcacag acagtagcag cttcctcgag    6060
aagggactac gaaaggccgg tgcagctgtt accatggaga cagatgtgtt gtgggctcag    6120
gctttaccag caaacacctc agcacaaaag gctgaattga tcgccctcac tcaggctctc    6180
cgatggggta aggatattaa cgttaacact gacagcaggt acgcctttgc tactgtgcat    6240
gtacgtggag ccatctacca ggagcgtggg ctactcacct cagcaggtgg ctgtaatcca    6300
ctgtaaagga catcaaaagg aaaacacggc tgttgcccgt ggtaaccaga aagctgattc    6360
agcagctcaa gatgcagtgt gactttcagt cacgcctcta aacttgctgc ccacagtctc    6420 cttccacag ccagatctgc ctgacaatcc cgcatactca acagaagaag aaaactggcc    6480
tcagaactca gagccaataa aaatcaggaa ggttggtgga ttcttcctga ctctagaatc    6540 ttcataccccc gaactcttgg gaaaacttta atcagtcacc tacagtctac cacccattta    6600
ggaggagcaa agctacctca gctcctccgg agccgtttta agatccccca tcttcaaagc    6660
ctaacagatc aagcagctct ccggtgcaca acctgcgccc aggtaaatgc caaaaaaggt    6720
cctaaaccca gcccaggcca ccgtctccaa gaaaactcac caggagaaaa gtgggaaatt    6780
gactttacag aagtaaaacc acaccgggct gggtacaaat accttctagt actggtagac    6840
accttctctg gatggactga agcatttgct accaaaaacg aaactgtcaa tatggtagtt    6900
aagtttttac tcaatgaaat catccctcga cgtgggctgc ctgttgccat agggtctgat    6960
aatggaccgg ccttcgcctt gtctatagtt tagtcagtca gtaaggcgtt aaacattcaa    7020
tggaagctcc attgtgccta tcgacccag agctctgggc aagtagaacg catgaactgc    7080
acccctaaaa acactcttac aaaattaatc ttagaaaccg gtgtaaattg tgtaagtctc    7140
cttcctttag ccctacttag agtaaggtgc acccctact gggctgggtt cttacctttt    7200
gaaatcatgt atgggagggc gctgcctatc ttgcctaagc taagagatgc ccaattggca    7260
```

```
aaaatatcac aaactaattt attacagtac ctacagtctc cccaacaggt acaagatatc    7320
atcctgccac ttgttcgagg aacccatccc aatccaattc ctgaacagac agggccctgc    7380
cattcattcc cgccaggtga cctgttgttt gttaaaaagt tccagagaga aggactccct    7440
cctgcttgga agagacctca caccgtcatc acgatgccaa cggctctgaa ggtggatggc    7500
attcctgcgt ggattcatca ctcccgcatc aaaaaggcca acggagccca actagaaaca    7560
tgggtcccca gggctgggtc aggcccctta aaactgcacc taagttgggt gaagccatta    7620
gattaattct ttttcttaat tttgtaaaac aatgcatagc ttctgtcaaa cttatgtatc    7680
ttaagactca atataacccc cttgttataa ctgaggaatc aatgatttga ttccccaaaa    7740
acacaagtgg ggaatgtagt gtccaacctg gtttttacta accctgtttt tagactctcc    7800 ctttcctttta atcactcagc cttgtttcca cctgaattga ctctccctta gctaagagcg    7860
ccagatggac tccatcttgg ctctttcact ggcagccgct tcctcaagga cttaacttgt    7920
gcaagctgac tcccagcaca tccaagaatg caattaactg ataagatact gtggcaagct    7980
atatccgcag ttcccaggaa ttcgtccaat tgattcacc caaaagcccc gcgtctatca    8040
ccttgtaata atcttaaagc ccctgcacct ggaactatta acgttcctgt aaccatttat    8100 cctttttaact tttttgccta ctttatttct gtaaaattgt tttaactaga ccccccctct    8160
cctttctaaa ccaaagtata aaagcaaatc tagccccttc ttcaggccga gagaatttcg    8220
agcgttagcc gtctcttggc caccagctaa ataaacggat tcttcatgtg tctcaaagtg    8280
tggcgttttc tctaactcgc tcaggtacga ccgtggtagt attttcccca acgtcttatt    8340
tttagggcac gtatgtagag taacttttat gaaagaaacc agttaaggag gttttgggat    8400
ttcctttatc aactgtaata ctggttttga ttatttattt atttatttat tttttttgag    8460
aaggagtttc actcttgttg cccaggctgg agtgcaatgg tgcgatcttg gctcactgca    8520
acttccgcct cccaggttca gcgattctc ctgcctcagc ctcgagagta gctgggatta    8580
taggcatgcg ccaccacacc cagctaattt tgtattttta gtaaagatgg ggtttcttca    8640
tgttggtcaa gctggtctgg aactccccgc ctcgggtgat ctgcccgcct cggcctccga    8700
aagtgctggg attacaggtg tgatccacca cacccagccg atttatatgt atataaatca    8760
cattcctcta accaaaatgt agtgtttcct tccatcttga atataggctg tagacccccgt   8820 gggtatggga cattgttaac agtgagacca cagcagtttt tatgtcatct gacagcatct    8880
ccaaatagcc ttcatggttg tcactgcttc caagacaat tccaaataac acttcccagt     8940
gatgacttgc tacttgctat tgttacttaa tgtgttaagg tggctgttac agacactatt    9000
agtatgtcag gaattacacc aaaatttagt ggctcaaaca atcattttat tatgtatgtg    9060
gattctcatg gtcaggtcag gatttcagac agggcacaag ggtagcccac ttgtctctgt    9120
ctatgatgtc tggcctcagc acaggagact caacagctgg ggtctgggac catttggagg    9180
cttgttccct cacatctgat acctggcttg ggatgttgga agaggggtg agctgagact     9240 gagtgcctat atgtagtgtt tccatatggc cttgacttcc ttacagcctg gcagcctcag    9300
ggtagtcaga attcttagga ggcacagggc tccaggggcag atgctgaggg gtcttttatg   9360
aggtagcaca gcaaatccac ccaggatc                                      9388
```

<210> SEQ ID NO 142
<211> LENGTH: 419
<212> TYPE: DNA
<213> ORGANISM: Homo sapien

<400> SEQUENCE: 142

```
tgtaagtcga gcagtgtgat ggaaggaatg gtctttggag agagcatatc catctcctcc    60
tcactgcctc ctaatgtcat gaggtacact gagcagaatt aaacagggta gtcttaacca   120
cactattttt agctaccttg tcaagctaat ggttaaagaa cacttttggt ttacacttgt   180
tgggtcatag aagttgcttt ccgccatcac gcaataagtt tgtgtgtaat cagaaggagt   240
taccttatgg tttcagtgtc attctttagt taacttggga gctgtgtaat ttaggctttg   300
cgtattattt cacttctgtt ctccacttat gaagtgattg tgtgttcgcg tgtgtgtgcg   360
tgcgcatgtg cttccggcag ttaacataag caaatatccca acatcacact gctcgactt   419
```

<210> SEQ ID NO 143
<211> LENGTH: 402
<212> TYPE: DNA
<213> ORGANISM: Homo sapien

<400> SEQUENCE: 143

```
tgtaagtcga gcagtgtgat gtccactgca gtgtgttgct gggaacagtt aatgagcaaa    60
ttgtatacaa tggctagtac attgaccggg atttgttgaa gctggtgagt gttatgactt   120
agcctgttag actagtctat gcacatggct ctggtcaact accgctctct catttctcca   180
gataaatccc ccatgcttta tattctcttc caaacatact atcctcatca ccacatagtt   240
cctttgttaa tgctttgttc tagactttcc cttttctgtt ttcttattca aacctatatc   300
tctttgcata gattgtaaat tcaaatgccc tcagggtgca ggcagttcat gtaagggagg   360
gaggctagcc agtgagatct gcatcacact gctcgactta ca                      402
```

<210> SEQ ID NO 144
<211> LENGTH: 224
<212> TYPE: DNA
<213> ORGANISM: Homo sapien

<400> SEQUENCE: 144

```
tcgggtgatg cctcctcagg ccaagaagat aaagcttcag acccctaaca catttccaaa    60
aaggaagaaa ggagaaaaaa gggcatcatc cccgttccga aggtcaggg aggaggaaat   120 tgaggtggat tcacgagttg cggacaactc ctttgatgcc aagcgaggtg cagccggaga   180
ctggggagag cgagccaatc aggttttgaa gttcctctca gtgc                    224
```

<210> SEQ ID NO 145
<211> LENGTH: 111
<212> TYPE: DNA
<213> ORGANISM: Homo sapien

<400> SEQUENCE: 145

```
agccatttac cacccatcca caaaaaaaa aaaaaaaag aaaatatca aggaataaaa     60 atagactttg aacaaaaagg aacatttgct ggcctgagga ggcatcaccc g           111
```

<210> SEQ ID NO 146
<211> LENGTH: 585
<212> TYPE: DNA
<213> ORGANISM: Homo sapien

<400> SEQUENCE: 146

```
tagcatgttg agcccagaca cttgtagaga gaggaggaca gttagaagaa gagaaaagt     60 ttttaaatgc tgaaagttac tataagaaag ctttggcttt ggatgagact ttaaagatg   120 cagaggatgc tttgcagaaa cttcataaat atatgcaggt gattccttat ttcctcctag   180
```

```
aaatttagtg atatttgaaa taatgcccaa acttaatttt ctcctgagga aaactattct      240
acattactta agtaaggcat tatgaaaagt ttcttttag gtatagtttt tcctaattgg       300
gtttgacatt gcttcatagt gcctctgttt ttgtccataa tcgaaagtaa agatagctgt     360
gagaaaacta ttacctaaat ttggtatgtt gttttgagaa atgtccttat agggagctca     420
cctggtggtt tttaaattat tgttgctact ataattgagc taattataaa aaccttttg     480 agacatattt taaattgtct tttcctgtaa tactgatgat gatgttttct catgcatttt    540
cttctgaatt gggaccattg ctgctgtgtc tgggctcaca tgcta                    585
```

<210> SEQ ID NO 147
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 147

```
tagcatgttg agcccagaca ctgggcagcg ggggtggcca cggcagctcc tgccgagccc      60
aagcgtgttt gtctgtgaag gaccctgacg tcacctgcca ggctagggag gggtcaatgt     120
ggagtgaatg ttcaccgact ttcgcaggag tgtgcagaag ccaggtgcaa cttggtttgc     180
ttgtgttcat caccctcaa gatatgcaca ctgctttcca aataaagcat caactgtcat      240
ctccagatgg ggaagactt ttctccaacc agcaggcagg tccccatcca ctcagacacc      300
agcacgtcca ccttctcggg cagcaccacg tcctccacct tctgctggta cacggtgatg     360
atgtcagcaa agccgttctg cangaccagc tgccccgtgt gctgtgccat ctcactggcc     420
tccaccgcgt acaccgctct aggccgcgca tantgtgcac agaanaaatg atgatccagt     480
cccacagccc acgtccaaga ngactttatc cgtcagggat tctttattct gcaggatgac    540
ctgtggtatt aattgttcgt gtctgggctc aacatgcta                            579
```

<210> SEQ ID NO 148
<211> LENGTH: 249
<212> TYPE: DNA
<213> ORGANISM: Homo sapien

<400> SEQUENCE: 148

```
tgacaccttg tccagcatct gcaagccagg aagagagtcc tcaccaagat ccccaccccg      60
ttggcaccag gatcttggac ttccaatctc cagaactgtg agaaataagt atttgtcgct     120
aaataaatct ttgtggtttc agatatttag ctatagcaga tcaggctgac taagagaaac    180
cccataagag ttacatactc attaatctcc gtctctatcc ccaggtctca gatgctggac    240
aaggtgtca                                                             249
```

<210> SEQ ID NO 149
<211> LENGTH: 255
<212> TYPE: DNA
<213> ORGANISM: Homo sapien

<400> SEQUENCE: 149

```
tgacaccttg tccagcatct gctattttgt gacttttaa taatagccat tctgactggt       60
gtgagatggt aactcattgt gggtttggtc tgcatttctc taatgatcag tgatattaag    120 cttttttaa atatgcttgt tgaccacatg tatatcatct tttgagaagt gtctgttcat     180
atcctttgcc cacttttaa ttttttatc ttgtaaattt gtttaatttc cttacagatg      240
```
ctggacaagg tgtca                                                          255

<210> SEQ ID NO 150
<211> LENGTH: 318
<212> TYPE: DNA
<213> ORGANISM: Homo sapien

<400> SEQUENCE: 150
ttacgctgca acactgtgga ggccaagctg ggatcacttc ttcattctaa ctggagagga          60
gggaagttca agtccagcag agggtgggtg ggtagacagt ggcactcaga aatgtcagct         120
ggacccctgt ccccgcatag gcaggacagc aaggctgtgg ctctccaggg ccagctgaag         180
aacaggacac tgtctccgct gccacaaagc gtcagagact cccatctttg aagcacggcc         240
ttcttggtct tcctgcactt ccctgttctg ttagagacct ggttatagac aaggcttctc         300
cacagtgttg cagcgtaa                                                       318

<210> SEQ ID NO 151
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 151
tnacgcngcn acnntgtaga ganggnaagg cnttccccac attnccccctt catnanagaa         60
ttattcnacc aagnntgacc natgccnttt atgacttaca tgcnnactnc ntaatctgtn        120
tcnngcctta aaagcnnntc cactacatgc ntcancactg tntgtgtnac ntcatnaact        180
gtcngnaata ggggcncata actacagaaa tgcanttcat actgcttcca ntgccatcng        240
cgtgtggcct tncctactct tcttntattc caagtagcat ctctggantg cttccccact        300
ctccacattg ttgcagcnat aat                                                323

<210> SEQ ID NO 152
<211> LENGTH: 311
<212> TYPE: DNA
<213> ORGANISM: Homo sapien

<400> SEQUENCE: 152
tcaagattcc ataggctgac cagtccaagg agagttgaaa tcatgaagga gagtctatct         60
ggagagagct gtagttttga gggttgcaaa gacttaggat ggagttggtg ggtgtggtta        120
gtctctaagg ttgattttgt tcataaattt catgccctga atgccttgct tgcctcaccc        180
tggtccaagc cttagtgaac acctaaaagt ctctgtcttc ttgctctcca aacttctcct        240
gaggatttcc tcagattgtc tacattcaga tcgaagccag ttggcaaaca agatgcagtc        300
cagagggtca g                                                              311

<210> SEQ ID NO 153
<211> LENGTH: 332
<212> TYPE: DNA
<213> ORGANISM: Homo sapien

<400> SEQUENCE: 153
caagattcca taggctgacc aggaggctat tcaagatctc tggcagttga ggaagtctct         60
ttaagaaaat agtttaaaca atttgttaaa atttttctgt cttacttcat ttctgtagca        120

-continued

| gttgatatct ggctgtcctt tttataatgc agagtgggaa ctttccctac catgtttgat | 180 |
| aaatgttgtc caggctccat tgccaataat gtgttgtcca aaatgcctgt ttagtttta | 240 |
| aagacggaac tccacccttt gcttggtctt aagtatgtat ggaatgttat gataggacat | 300 |
| agtagtagcg gtggtcagcc tatggaatct tg | 332 |

<210> SEQ ID NO 154
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 154

| tcaagattcc ataggctgac ctggacagag atctcctggg tctggcccag gacagcaggc | 60 |
| tcaagctcag tggagaaggt ttccatgacc ctcagattcc cccaaacctt ggattgggtg | 120 |
| acattgcatc tcctcagaga gggaggagat gtangtctgg gcttccacag ggacctggta | 180 |
| ttttaggatc agggtaccgc tggcctgagg cttggatcat tcanagcctg ggggtggaat | 240 |
| ggctggcagc ctgtggcccc attgaaatag gctctggggc actccctctg ttcctanttg | 300 |
| aacttgggta aggaacagga atgtggtcan cctatggaat cttga | 345 |

<210> SEQ ID NO 155
<211> LENGTH: 295
<212> TYPE: DNA
<213> ORGANISM: Homo sapien
<220> FEATURE:
<221> NAME/KEY: misc_feature
<222> LOCATION: (1)...(295)
<223> OTHER INFORMATION: n = A,T,C or G

<400> SEQUENCE: 155

| gacgcttggc cacttgacac attaaacagt tttgcataat cactancatg tatttctagt | 60 |
| ttgctgtctg ctgtgatgcc ctgccctgat tctctggcgt taatgatggc aagcataatc | 120 |
| aaacgctgtt ctgttaattc caagttataa ctggcattga ttaaagcatt atctttcaca | 180 |
| actaaactgt tcttcatana acagcccata ttattatcaa attaagagac aatgtattcc | 240 |
| aatatccttt anggccaata tatttnatgt cccttaatta agagctactg tccgt | 295 |

<210> SEQ ID NO 156
<211> LENGTH: 406
<212> TYPE: DNA
<213> ORGANISM: Homo sapien
<220> FEATURE:
<221> NAME/KEY: misc_feature
<222> LOCATION: (1)...(406)
<223> OTHER INFORMATION: n = A,T,C or G

<400> SEQUENCE: 156

| gacgcttggc cacttgacac tgcagtggga aaaccagcat gagccgctgc ccccaaggaa | 60 |
| cctcgaagcc caggcagagg accagccatc ccagcctgca ggtaaagtgt gtcacctgtc | 120 |
| aggtgggctt ggggtgagtg ggtgggggaa gtgtgtgtgc aaaggggggtg tnaatgtnta | 180 |
| tgcgtgtgag catgagtgat ggctagtgtg actgcatgtc agggagtgtg aacaagcgtg | 240 |
| cgggggtgtg tgtgcaagtg cgtatgcata tgagaatatg tgtctgtgga tgagtgcatt | 300 |
| tgaaagtctg tgtgtgtgcg tgtggtcatg anggtaantt antgactgcg caggatgtgt | 360 |
| gagtgtgcat ggaacactca ntgtgtgtgt caagtggccn ancgtc | 406 |

<210> SEQ ID NO 157
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 157

| | | | | | |
|---|---|---|---|---|---|
| tgacgcttgg | ccacttgaca | cactaaaggg | tgttactcat | cactttcttc | tctcctcggt | 60 |
| ggcatgtgag | tgcatctatt | cacttggcac | tcatttgttt | ggcagtgact | gtaanccana | 120 |
| tctgatgcat | acaccagctt | gtaaattgaa | taaatgtctc | taatactatg | tgctcacaat | 180 |
| anggtanggg | tgaggagaag | gggagaga | | | | 208 |

<210> SEQ ID NO 158
<211> LENGTH: 547
<212> TYPE: DNA
<213> ORGANISM: Homo sapien
<220> FEATURE:
<221> NAME/KEY: misc_feature
<222> LOCATION: (1)...(547)
<223> OTHER INFORMATION: n = A,T,C or G

<400> SEQUENCE: 158

| | | | | | |
|---|---|---|---|---|---|
| cttcaacctc | cttcaacctc | cttcaacctc | ctggattcaa | acaatcatcc | cacctcagac | 60 |
| tccttagtag | ctgagactac | agactcacgc | cactacatct | ggctaaattt | ttgtagagat | 120 |
| agggttttcat | catgttgccc | tggctggtct | caaactcctg | acctcaagca | atgtgcccac | 180 |
| ctcagcctcc | caaagtgctg | ggattacagg | cataagccac | catgcccagt | ccatntttaa | 240 |
| tctttcctac | cacattctta | ccacactttc | ttttatgttt | agatacataa | atgcttacca | 300 |
| ttatgataca | attgcccaca | gtattaagac | agtaacatgc | tgcacaggtt | tgtagcctag | 360 |
| gaacagtagg | caataccaca | tagcttaggt | gtgtggtaga | ctataccatc | taggtttgtg | 420 |
| taagttacac | tttatgctgt | ttacacaatg | acaaaaccat | ctaatgatgc | atttctcaga | 480 |
| atgtatcctt | gtcagtaagc | tatgatgtac | agggaacact | gcccaaggac | acagatattg | 540 |
| tacctgt | | | | | | 547 |

<210> SEQ ID NO 159
<211> LENGTH: 203
<212> TYPE: DNA
<213> ORGANISM: Homo sapien

<400> SEQUENCE: 159

| | | | | | |
|---|---|---|---|---|---|
| gctcctcttg | ccttaccaac | tcacccagta | tgtcagcaat | tttatcrgct | ttacctacga | 60 |
| aacagcctgt | atccaaacac | ttaacacact | cacctgaaaa | gttcaggcaa | caatcgcctt | 120 |
| ctcatgggtc | tctctgctcc | agttctgaac | ctttctcttt | tcctagaaca | tgcatttarg | 180 |
| tcgatagaag | ttcctctcag | tgc | | | | 203 |

<210> SEQ ID NO 160
<211> LENGTH: 402
<212> TYPE: DNA
<213> ORGANISM: Homo sapien

<400> SEQUENCE: 160

| | | | | | |
|---|---|---|---|---|---|
| tgtaagtcga | gcagtgtgat | gggtggaaca | gggttgtaag | cagtaattgc | aaactgtatt | 60 |

```
taaacaataa taataatatt tagcatttat agagcactt  atatcttcaa agtacttgca      120
aacattayct aattaaatac cctctctgat tataatctgg atacaaatgc acttaaactc      180
aggacagggt catgagaraa gtatgcattt gaaagttggt gctagctatg ctttaaaaac      240
ctatacaatg atgggraagt tagagttcag attctgttgg actgttttg  tgcatttcag     300 ttcagcctga tggcagaatt agatcatatc tgcactcgat gactytgctt gataacttat      360
cactgaaatc tgagtgttga tcatcacact gctcgactta ca                         402
```

<210> SEQ ID NO 161
<211> LENGTH: 193
<212> TYPE: DNA
<213> ORGANISM: Homo sapien

<400> SEQUENCE: 161

```
agcatgttga gcccagacac tgaccaggag aaaaaccaac caatagaaac acgcccagac      60
actgaccagg agaaaaacca accaataaaa acaggcccgg acataagaca aataataaaa      120
ttagcggaca aggacatgaa acagctatt  gtaagagcgg atatagtggt gtgtgtctgg      180
gctcaacatg cta                                                          193
```

<210> SEQ ID NO 162
<211> LENGTH: 147
<212> TYPE: DNA
<213> ORGANISM: Homo sapien

<400> SEQUENCE: 162

```
tgttgagccc agacactgac caggagaaaa accaaccaat aaaaacaggc cggacataa       60 gacaaataat aaaaattagcg gacaaggaca tgaaaacagc tattgtaaga gcggatatag     120
tggtgtgtgt ctgggctcaa catgcta                                          147
```

<210> SEQ ID NO 163
<211> LENGTH: 294
<212> TYPE: DNA
<213> ORGANISM: Homo sapien

<400> SEQUENCE: 163

```
tagcatgttg agcccagaca caaatctttc cttaagcaat aaatcatttc tgcatatgtt      60
tttaaaacca cagctaagcc atgattattc aaaaggacta ttgtattggg tattttgatt      120
tgggttctta tctccctcac attatcttca tttctatcat tgacctctta tcccagagac      180
tctcaaactt ttatgttata caaatcacat tctgtctcaa aaaatatctc acccacttct      240
cttctgtttc tgcgtgtgta tgtgtgtgtg tgtgtgtctg ggctcaacat gcta            294
```

<210> SEQ ID NO 164
<211> LENGTH: 412
<212> TYPE: DNA
<213> ORGANISM: Homo sapien
<220> FEATURE:
<221> NAME/KEY: misc_feature
<222> LOCATION: (1)...(412)
<223> OTHER INFORMATION: n = A,T,C or G

<400> SEQUENCE: 164

```
cgggattggc tttgagctgc agatgctgcc tgtgaccgca cccggcgtgg aacagaaagc      60
cacctggctg caagtgcgcc agagccgccc tgactacgtg ctgctgtggg gctgggcgt       120 gatgaactcc accgccctga aggaagccca ggccaccgga taccccgcg  acaagatgta     180 cggcgtgtgg tgggccggtg cggagcccga tgtgcgtgac gtgggcgaag gcgccaaggg     240
```

```
ctacaacgcg ctggctctga acggctacgg cacgcagtcc aaggtgatcc angacatcct    300
gaaacacgtg cacgacaagg gccagggcac ggggcccaaa gacgaagtgg gctcggtgct    360
gtacacccgc ggcgtgatca tccagatgct ggacaaggtg tcaatcacta at            412
```

<210> SEQ ID NO 165
<211> LENGTH: 361
<212> TYPE: DNA
<213> ORGANISM: Homo sapien

<400> SEQUENCE: 165

```
ttgacacctt gtccagcatc tgcatctgat gagagcctca gatggctacc actaatggca    60
gaaggcaaag gagaacaggc attgtatggc aagaaaggaa gaaagagaga ggggagaaag    120
gtgctaggtt cttttcaaca accagttctt gatggaactg agagtaagag ctcaaggcca    180
ggtgtggtga ctccaaccag taatcccaac attttaggag gctgaggcag gcagatgtct    240 tgacccatg agtttgtgac cagcctgaac aacatcatga gactccatct ctacaataat    300
tacaaaaatt aatcaggcat tgtggtatgc cctgtagtcc cagatgctgg acaaggtgtc    360
a                                                                    361
```

<210> SEQ ID NO 166
<211> LENGTH: 427
<212> TYPE: DNA
<213> ORGANISM: Homo sapien

<400> SEQUENCE: 166

```
twgactgact catgtcccct acacccaact atcttctcca ggtggccagg catgatagaa    60
tctgatcctg acttagggga atattttctt tttacttccc atcttgattc cctgccggtg    120
agtttcctgg ttcagggtaa gaaggagct caggccaaag taatgaacaa atccatcctc    180
acagacgtac agaataagag aacwtggacw tagccagcag aacmcaaktg aaamcagaac    240
mcttamctag gatracaamc mcrraratar ktgcycmcmc wtataataga aaccaaactt    300
gtatctaatt aaatatttat ccacygtcag ggcattagtg gttttgataa atacgctttg    360
gctaggattc ctgaggttag aatggaaraa caattgcamc gagggtaggg gacatgagtc    420 aktctaa                                                              427
```

<210> SEQ ID NO 167
<211> LENGTH: 500
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 167

```
aacgtcgcat gctcccggcc gccatggccg cgggatagac tgactcatgt cccctaagat    60
agaggagaca cctgctaggt gtaaggagaa gatggttagg tctacggagg ctccaggtg     120 ggagtagttc cctgctaagg gagggtagac tgttcaacct gttcctgctc cggcctccac    180
tatagcagat gcgagcagga gtaggagaga gggaggtaag agtcagaagc ttatgttgtt    240
tatgcgggga aacgccrtat cggggggcagc cragttatta ggggacantr tagwyartcw   300
agntagcatc caaagcgngg gagttntccc atatggttgg acctgcaggc ggccgcatta   360
gtgattagca tgtgagcccc agacacgcat agcaacaagg acctaaactc agatcctgtg    420
```

```
ctgattactt aacatgaatt attgtattta tttaacaact ttgagttatg aggcatatta      480
ttaggtccat attacctgga                                                  500

<210> SEQ ID NO 168
<211> LENGTH: 358
<212> TYPE: DNA
<213> ORGANISM: Homo sapien

<400> SEQUENCE: 168
ttcatcgctc ggtgactcaa gcctgtaatc ccagaacttt gggaggccga ggggagcaga       60
tcacctgagg ttgggagttt gagaccagcc tggccaacat ggtgacaacc cgtctctgct      120
aaaaatacaa aaattagcca agcatggtgg catgcacttg taatcccagc tactcgggag      180
gctgaggcag gagaatcact tgaggccagg aggcagaggt tgcagtgagg cagaggttga      240
gatcatgcca ctgcactcca gcctgggcaa cagagtaaga ctccatctca aaaaaaaaa       300 aaaaaagaa tgatcagagc cacaaataca gaaaaccttg agtcaccgag cgatgaaa        358

<210> SEQ ID NO 169
<211> LENGTH: 1265
<212> TYPE: DNA
<213> ORGANISM: Homo sapien

<400> SEQUENCE: 169
ttctgtccac accaatctta gagctctgaa agaatttgtc tttaaatatc ttttaatagt       60
aacatgtatt ttatggacca aattgacatt ttcgactatt ttttcccaaa aaagtcagg      120 tgaatttcag cacactgagt tgggaatttc ttatcccaga agwcggcacg agcaatttca      180
tatttattta agattgattc catactccgt tttcaaggag aatccctgca gtctccttaa      240
aggtagaaca aatactttct attttttttt caccattgtg ggattggact ttaagaggtg      300
actctaaaaa aacagagaac aaatatgtct cagttgtatt aagcacggac ccatattatc      360
atattcactt aaaaaaatga tttcctgtgc acctttggc aacttctctt ttcaatgtag       420
ggaaaaactt agtcaccctg aaacccaca aataaataa aacttgtaga tgtgggcaga        480
argtttgggg gtggacattg tatgtgttta aattaaaccc tgtatcactg agaagctgtt      540
gtatgggtca gagaaaatga atgcttagaa gctgttcaca tcttcaagag cagaagcaaa      600
ccacatgtct cagctatatt attatttatt ttttatgcat aaagtgaatc atttcttctg      660
tattaatttc caagggtttt taccctctat ttaaatgctt tgaaaaacag tgcattgaca      720
atgggttgat atttttcttt aaaagaaaaa tataattatg aaagccaaga taatctgaag      780
cctgttttat tttaaaactt tttatgttct gtggttgatg ttgtttgttt gtttgtttct      840
attttgttgg ttttttactt tgttttttgt tttgttttgt tttggttttdg catactacat      900 gcagtttctt taaccaatgt ctgtttggct aatgtaatta aagttgttaa tttatatgag      960
tgcatttcaa ctatgtcaat ggtttcttaa tatttattgt gtagaagtac tggtaatttt     1020
tttatttaca atatgtttaa agagataaca gtttgatatg ttttcatgtg tttatagcag     1080
aagttattta tttctatggc attccagcgg atattttggt gtttgcgagg catgcagtca     1140
atattttgta cagttagtgg acagtattca gcaacgcctg atagcttctt tggccttatg     1200
ttaaataaaa agacctgttt gggatgtaaa aaaaaaaaa aaaaaaaaa aaaaaaaaa        1260 aaaaa                                                                1265

<210> SEQ ID NO 170
<211> LENGTH: 383
```

```
<212> TYPE: DNA
<213> ORGANISM: Homo sapien

<400> SEQUENCE: 170
tgtaagtcga gcagtgtgat gacgatattc ttcttattaa tgtggtaatt gaacaaatga      60
tctgtgatac tgatcctgag ctaggaggcg ctgttcagtt aatgggactt cttcgtactc     120
taattgatcc agagaacatg ctggctacaa ctaataaaac cgaaaaaagt gaatttctaa     180
attttttcta caaccattgt atgcatgttc tcacagcacc acttttgacc aatacttcag     240
aagacaaatg tgaaaaggat aatatagttg atcaaaacaa aaacaacaca atttgtcccg     300
ataattatca aacagcacag ctacttgcct taatttttaga gttactcaca ttttgtgtgg     360
aacatcacac tgctcgactt aca                                             383

<210> SEQ ID NO 171
<211> LENGTH: 383
<212> TYPE: DNA
<213> ORGANISM: Homo sapien

<400> SEQUENCE: 171
tgggcacctt caatatcgca agttaaaaat aatgttgagt ttattatact tttgacctgt      60
ttagctcaac agggtgaagg catgtaaaga atgtggactt ctgaggaatt ttctttttaaa    120 aagaacataa tgaagtaaca ttttaattac tcaaggacta cttttggttg aagtttataa     180
tctagatacc tctactttt gttttgctg ttcgacagtt cacaaagacc ttcagcaatt     240
tacagggtaa aatcgttgaa gtagtggagg tgaaactgaa atttaaaatt attctgtaaa    300
tactataggg aaagaggctg agcttagaat cttttggttg ttcatgtgtt ctgtgctctt     360
atcatcacac tgctcgactt aca                                             383

<210> SEQ ID NO 172
<211> LENGTH: 699
<212> TYPE: DNA
<213> ORGANISM: Homo sapien
<220> FEATURE:
<221> NAME/KEY: misc_feature
<222> LOCATION: (1)...(699)
<223> OTHER INFORMATION: n = A,T,C or G

<400> SEQUENCE: 172
tcgggtgatg cctcctcagg cttgtcgtta gtgtacacag agctgctcat gaagcgacag      60
cggctgcccc tggcacttca gaacctcttc ctctacactt ttggtgcgct tctgaatcta    120
ggtctgcatg ctggcggcgg ctctggccca ggcctcctgg aaagtttctc aggatgggca    180
gcactcgtgg tgctgagcca ggcactaaat ggactgctca tgtctgctgt catggagcat    240
ggcagcagca tcacacgcct ctttgtggtg tcctgctcgc tggtggtcaa cgccgtgctc    300
tcagcagtcc tgctacggct gcagctcaca gccgccttct tcctggccac attgctcatt    360
ggcctggcca tgcgcctgta ctatggcagc cgctagtccc tgacaacttc caccctgatt    420
ccggaccctg tagattgggc gccaccacca gatccccctc ccaggccttc ctccctctcc    480
catcagcggc cctgtaacaa gtgccttgtg agaaaagctg gagaagtgag ggcagccagg    540
ttattctctg gaggttggtg gatgaagggg taccctagg agatgtgaag tgtgggtttg     600
gttaaggaaa tgcttaccat cccccacccc caaccaagtt nttccagact aaagaattaa    660
ggtaacatca ataccctaggc ctgaggaggc atcacccga                           699

<210> SEQ ID NO 173
```

<210> SEQ ID NO 173
<211> LENGTH: 701
<212> TYPE: DNA
<213> ORGANISM: Homo sapien

<400> SEQUENCE: 173

| | | | | | | |
|---|---|---|---|---|---|---|
| tcgggtgatg | cctcctcagg | ccagatcaaa | cttggggttg | aaaactgtgc | aaagaaatca | 60 |
| atgtcggaga | aagaattttg | caaaagaaaa | atgcctaatc | agtactaatt | taataggtca | 120 |
| cattagcagt | ggaagaagaa | atgttgatat | tttatgtcag | ctattttata | atcaccagag | 180 |
| tgcttagctt | catgtaagcc | atctcgtatt | cattagaaat | aagaacaatt | ttattcgtcg | 240 |
| gaaagaactt | ttcaatttat | agcatcttaa | ttgctcagga | ttttaaattt | tgataaagaa | 300 |
| agctccactt | ttggcaggag | taggggggcag | ggagagagga | ggctccatcc | acaaggacag | 360 |
| agacaccagg | gccagtaggg | tagctggtgg | ctggatcagt | cacaacggac | tgacttatgc | 420 |
| catgagaaga | aacaacctcc | aaatctcagt | tgcttaatac | aacacaagct | catttcttgc | 480 |
| tcacgttaca | tgtcctatgt | agatcaacag | caggtgactc | agggacccag | gctccatctc | 540 |
| catatgagct | tccatagtca | ccaggacacg | ggctctgaaa | gtgtcctcca | tgcagggaca | 600 |
| catgcctctt | cctttcattg | ggcagagcaa | gtcacttatg | gccagaagtc | acactgcagg | 660 |
| gcagtgccat | cctgctgtat | gcctgaggag | gcatcacccg | a | | 701 |

<210> SEQ ID NO 174
<211> LENGTH: 700
<212> TYPE: DNA
<213> ORGANISM: Homo sapien
<220> FEATURE:
<221> NAME/KEY: misc_feature
<222> LOCATION: (1)...(700)
<223> OTHER INFORMATION: n = A,T,C or G

<400> SEQUENCE: 174

| | | | | | | |
|---|---|---|---|---|---|---|
| tcgggtgatg | cctcctcang | cccctaaatc | agagtccagg | gtcagagcca | caggagacag | 60 |
| ggaaagacat | agattttaac | cggccccctt | caggagattc | tgaggctcag | ttcactttgt | 120 |
| tgcagtttga | acagaggcag | caaggctagt | ggttaggggc | acggtctcta | aagctgcact | 180 |
| gcctggatct | gcctcccagc | tctgccagga | accagctgcg | tggccttgag | ctgctgacac | 240 |
| gcagaaagcc | ccctgtggac | ccagtctcct | cgtctgtaag | atgaggacag | gactctagga | 300 |
| acccttccc | ttggtttggc | ctcactttca | caggctccca | tcttgaactc | tatctactct | 360 |
| tttcctgaaa | ccttgtaaaa | gaaaaagtg | ctagcctggg | caacatggca | aaaccctgtc | 420 |
| tctacaaaaa | atacaaaaat | tagttgggtg | tggtggcatg | tgcctgtagt | cccagccact | 480 |
| tgggaggtgc | tgaggtggga | ggatcacttg | agcccgggag | gtggaggttg | cagtgagcca | 540 |
| agatcatgcc | actgcactcc | agcctgagta | atagagtaag | actctgtctc | aaaaacaaca | 600 |
| acaacaacag | tgagtgtgcc | tctgtttccg | ggttggatgg | ggcaccacat | ttatgcatct | 660 |
| ctcagatttg | gacgctgcag | cctgaggagg | catcacccga | | | 700 |

<210> SEQ ID NO 175
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 175

| | | | | | | |
|---|---|---|---|---|---|---|
| tatagggcga | attgggcccg | agttgcatgn | tcccggccgc | catggccgcg | ggattcgggt | 60 |

```
gatgcctcct caggcttgtc tgccacaagc tacttctctg agctcagaaa gtgcccttg      120 atgagggaaa atgtcctact gcactgcgaa tttctcagtt ccattttacc tcccagtcct    180
ccttctaaac cagttaataa attcattcca caagtattta ctgattacct gcttgtgcca    240
gggactattc tcaggctgaa gaaggtggga ggggagggcg gaacctgagg agccacctga    300
gccagcttta tatttcaacc atggctggcc atctgagag catctcccca ctctcgccaa     360
cctatcgggg catagcccag ggatgccccc aggcggccca ggttagatgc gtccctttgg    420
cttgtcagtg atgacataca ccttagctgc ttagctggtg ctggcctgag gaggcatcac    480
ccga                                                                 484

<210> SEQ ID NO 176
<211> LENGTH: 432
<212> TYPE: DNA
<213> ORGANISM: Homo sapien

<400> SEQUENCE: 176
tcgggtgatg cctcctcagg gctcaaggga tgagaagtga cttctttctg gagggaccgt     60
tcatgccacc caggatgaaa atggataggg acccacttgg aggacttgct gatatgtttg    120
gacaaatgcc aggtagcgga attggtactg gtccaggagt tatccaggat agattttcac    180
ccaccatggg acgtcatcgt tcaaatcaac tcttcaatgg ccatggggga cacatcatgc    240
ctcccacaca atcgcagttt ggagagatgg gaggcaagtt tatgaaaagc caggggctaa    300
gccagctcta ccataaccag agtcagggac tcttatccca gctgcaagga cagtcgaagg    360
atatgccacc tcggttttct aagaaaggac agcttaatgc agatgagatt agcctgagga    420
ggcatcaccc ga                                                        432

<210> SEQ ID NO 177
<211> LENGTH: 788
<212> TYPE: DNA
<213> ORGANISM: Homo sapien

<400> SEQUENCE: 177
tagcatgttg agcccagaca cagtagcatt tgtgccaatt tctggttgga atggtgacaa      60
catgctggag ccaagtgcta acatgccttg gttcaaggga tggaaagtca cccgtaagga    120
tggcaatgcc agtggaacca cgctgcttga ggctctggac tgcatcctac caccaactcg    180
cccaactgac aagcccttgc gcctgcctct ccaggatgtc tacaaaattg gtggtattgg    240
tactgttcct gttggccgag tggagactgg tgttctcaaa cccggtatgg tggtcacctt    300
tgctccagtc aacgttacaa cggaagtaaa atctgtcgaa atgcaccatg aagctttgag    360
tgaagctctt cctggggaca atgtgggctt caatgtcaag aatgtgtctg tcaaggatgt    420
tcgtcgtggc aacgttgctg gtgacagcaa aaatgaccca ccaatggaag cagctggctt    480
cactgctcag gtgattatcc tgaaccatcc aggccaaata agtgccggct atgcccctgt    540
attggattgc cacacggctc acattgcatg caagtttgct gagctgaagg aaaagattga    600
tcgccgttct ggtaaaaagc tggaagatgg ccctaaattc ttgaagtctg gtgatgctgc    660
cattgttgat atggttcctg gcaagcccat gtgtgttgag agcttctcag actatccacc    720
tttgggtcgc tttgctgttc gtgatatgag acagacagtt gcggtgggtg tctgggctca    780
acatgcta                                                             788

<210> SEQ ID NO 178
```

<211> LENGTH: 786
<212> TYPE: DNA
<213> ORGANISM: Homo sapien

<400> SEQUENCE: 178

| tagcatgttg | agcccagaca | cctgtgtttc | tgggagctct | ggcagtggcg | gattcatagg | 60 |
| cacttgggct | gcactttgaa | tgacacactt | ggctttatta | gattcactag | tttttaaaaa | 120 |
| attgttgttc | gtttcttttc | attaaaggtt | taatcagaca | gatcagacag | cataattttg | 180 |
| tatttaatga | cagaaacgtt | ggtacatttc | ttcatgaatg | agcttgcatt | ctgaagcaag | 240 |
| agcctacaaa | aggcacttgt | tataaatgaa | agttctggct | ctagaggcca | gtactctgga | 300 |
| gtttcagagc | agccagtgat | tgttccagtc | agtgatgcct | agttatatag | aggaggagta | 360 |
| cactgtgcac | tcttctaggt | gtaagggtat | gcaactttgg | atcttaaaat | tctgtacaca | 420 |
| tacacacttt | atatatatgt | atgtatgtat | gaaaacatga | aattagtttg | tcaaatatgt | 480 |
| gtgtgtttag | tattttagct | tagtgcaact | atttccacat | tatttattaa | attgatctaa | 540 |
| gacactttct | tgttgacacc | ttgaatatta | atgttcaagg | gtgcaatgtg | tattccttta | 600 |
| gattgttaaa | gcttaattac | tatgatttgt | agtaaattaa | cttttaaaat | gtatttgagc | 660 |
| ccttctgtag | tgtcgtaggg | ctcttacagg | gtgggaaaga | ttttaattt  | ccagttgcta | 720 |
| attgaacagt | atggcctcat | tatatatttt | gatttatagg | agtttgtgtc | tgggctcaac | 780 |
| atgcta     |            |            |            |            |            | 786 |

<210> SEQ ID NO 179
<211> LENGTH: 796
<212> TYPE: DNA
<213> ORGANISM: Homo sapien

<400> SEQUENCE: 179

| tagcatgttg | agcccagaca | ctggttacaa | gaccagacct | gcttcctcca | tatgtaaaca | 60 |
| gcttttaaaa | agccagtgaa | cctttttaat | actttggcaa | ccttctttca | caggcaaaga | 120 |
| acaccccat  | ccgccccttg | tttggagtgc | agagtttggc | tttggttctt | tgccttgcct | 180 |
| ggagtatact | tctaattcct | gttgtcctgc | acaagctgaa | taccgagcta | cccaccgcca | 240 |
| cccaggccag | gttccactc  | atttattact | ttatgtttct | gttccattgc | tggtccacag | 300 |
| aaataagttt | tcctttggag | gaatgtgatt | atacccttt  | aatttcctcc | ttttgctttt | 360 |
| ttttaatatc | attggtatgt | gtttggccca | gaggaaactg | aaattcacca | tcatcttgac | 420 |
| tggcaatccc | attaccatgc | ttttttaaa  | aaacgtaatt | tttcttgcct | tacattggca | 480 |
| gagtagccct | tcctggctac | tggcttaatg | tagtcactca | gtttctaggt | ggcattaggc | 540 |
| atgagacctg | aagcacagac | tgtcttacca | caaaaggtga | caagatctca | aaccttagcc | 600 |
| aaagggctat | gtcaggtttc | aatgctatct | gcttctgttc | ctgctcactg | ttctggattt | 660 |
| tgtccttctt | catccctagc | accagaattt | cccagtctcc | ctccctacct | tcccttgttt | 720 |
| taattctaat | ctatcagcaa | aataacttt  | caaatgtttt | aaccggtatc | tccatgtgtc | 780 |
| tgggctcaac | atgcta     |            |            |            |            | 796 |

<210> SEQ ID NO 180
<211> LENGTH: 488
<212> TYPE: DNA
<213> ORGANISM: Homo sapien

<400> SEQUENCE: 180

| ggatgtgctg | caaggcgatt | aagttgggta | acgccagggt | tttcccagtc | acgacgttgt | 60 |

```
aaaacgacgg ccagtgaatt gtaatacgac tcactatagg gcgaattggg cccgacgtcg    120
catgctcccg ccgccatgg ccgcgggata gcatgttgag cccagacacc tgcaggtcat     180
ttggagagat ttttcacgtt accagcttga tggtctttt caggaggaga gacactgagc    240
actcccaagg tgaggttgaa gatttcctct agatagccgg ataagaagac taggagggat    300
gcctagaaaa tgattagcat gcaaatttct acctgccatt tcagaactgt gtgtcagccc    360
acattcagct gcttcttgtg aactgaaaag agagaggtat tgagactttt ctgatggccg    420
ctctaacatt gtaacacagt aatctgtgtg tgtgtgggtg tgtgtgtgtg tctgggctca    480
acatgcta                                                            488

<210> SEQ ID NO 181
<211> LENGTH: 317
<212> TYPE: DNA
<213> ORGANISM: Homo sapien

<400> SEQUENCE: 181
tagcatgttg agcccagaca cggcgacggt acctgatgag tggggtgatg gcacctgtga    60
aaaggaggaa cgtcatcccc catgatattg gggacccaga tgatgaacca tggctccgcg    120
tcaatgcata tttaatccat gatactgctg attggaagga cctgaacctg aagtttgtgc    180
tgcaggttta tcgggactat tacctcacgg gtgatcaaaa cttcctgaag gacatgtggc    240
ctgtgtgtct agtaagggat gcacatgcag tggccagtgt gccagggta tggttggtgt    300 ctgggctcaa catgcta                                                  317

<210> SEQ ID NO 182
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 182
tagcatgttg agcccagaca ctggctgtta gccaaatcct ctctcagctg ctccctgtgg    60
tttggtgact caggattaca gaggcatcct gtttcaggga acaaaaagat tttagctgcc    120
agcagagagc accacataca ttagaatggt aaggactgcc acctccttca agaacaggag    180
tgagggtggt ggtgaatggg aatggaagcc tgcattccct gatgcatttg tgctctctca    240
aatcctgtct tagtcttagg aaaggaagta agtttcaag gacggttccg aactgctttt    300
tgtgtctggg ctcaacatgc tatcccgcgg ccatggcggc cggagcatg cgacgtcggg    360 cccaattcgc cctatagtga gtcgtattac aattcactgg ccgtcgtttt acaacgtcgt    420
gactgggaaa accctggcgt tacccaactt aatcgccttg cagcacatcc cctttcccca    480
gctggcgtaa tancgaaaag gcccgca                                       507

<210> SEQ ID NO 183
<211> LENGTH: 227
<212> TYPE: DNA
<213> ORGANISM: Homo sapien

<400> SEQUENCE: 183
gatttacgct gcaacactgt ggaggtagcc ctggagcaag gcaggcatgg atgcttctgc    60
aatccccaaa tggagcctgg tatttcagcc aggaatctga gcagagcccc ctctaattgt   120
```

| | |
|---|---|
| agcaatgata agttattctc tttgttcttc aaccttccaa tagccttgag cttccagggg | 180 |
| agtgtcgtta atcattacag cctggtctcc acagtgttgc agcgtaa | 227 |

<210> SEQ ID NO 184
<211> LENGTH: 225
<212> TYPE: DNA
<213> ORGANISM: Homo sapien

<400> SEQUENCE: 184

| | |
|---|---|
| ttacgctgca acactgtgga gcagattaac atcagacttt tctatcaaca tgactggggt | 60 |
| tactaaaaag acaacaaatc aatggcttca aaagtctaag gaataatttc gatacttcaa | 120 |
| ctttataaaa cctgacaaaa ctatcaatca agcataaaga cagatgaaga acatttccag | 180 |
| attttggcca atcagatatt ttacctccac agtgttgcag cgtaa | 225 |

<210> SEQ ID NO 185
<211> LENGTH: 597
<212> TYPE: DNA
<213> ORGANISM: Homo sapien

<400> SEQUENCE: 185

| | |
|---|---|
| ggcccgacgt cgcatgctcc cggccgccat ggccgcggga ttcgttaggg tctctatcca | 60 |
| ctgggaccca taggctagtc agagtattta gagttgagtt cctttctgct tcccagaatt | 120 |
| tgaaagaaaa ggagtgaggt gatagagctg agagatcaga tttgcctctg aagcctgttc | 180 |
| aagatgtatg tgctcagacc ccaccactgg ggcctgtggg tgaggtcctg ggcatctatt | 240 |
| tgaatgaatt gctgaagggg agcactatgc caaggaaggg gaacccatcc tggcactggc | 300 |
| acagggtca cctatccag tgctcagtgc ttcttgctg ctacctggtt ttctctcata | 360 |
| tgtgagggc aggtaagaag aagtgcccrg tgttgtgcga gttttagaac atctaccagt | 420 |
| aagtggggaa gtttcacaaa gcagcagctt tgttttgtgt attttcacct tcagttagaa | 480 |
| gaggaaggct gtgagatgaa tgttagttga gtggaaaaga cgggtaagct tagtggatag | 540 |
| agaccctaac gaatcactag tgcggccgcc ttgcaggtcg accatatggg agagctc | 597 |

<210> SEQ ID NO 186
<211> LENGTH: 597
<212> TYPE: DNA
<213> ORGANISM: Homo sapien

<400> SEQUENCE: 186

| | |
|---|---|
| ggcccgaagt tgcatgttcc cggccgccat ggccgcggga ttcgttaggg tctctatcca | 60 |
| ctacctaaaa aatcccaaac atataactga actcctcaca cccaattgga ccaatccatc | 120 |
| accccagagg cctacagatc ctcctttgat acataagaaa atttccccaa actacctaac | 180 |
| tatatcattt tgcaagattt gttttaccaa attttgatgg cctttctgag cttgtcagtg | 240 |
| tgaaccacta ttacgaacga tcggatatta actgcccctc accgtccagg tgtagctggc | 300 |
| aacatcaagt gcagtaaata ttcattaagt tttcacctac taaggtgctt aaacaccta | 360 |
| gggtgccatg tcggtagcag atcttttgat ttgttttat ttcccataag ggtcctgttc | 420 |
| aaggtcaatc atacatgtag tgtgagcagc tagtcactat cgcatgactt ggagggtgat | 480 |
| aatagaggcc tcctttgctg ttaaagaact cttgtcccag cctgtcaaag tggatagaga | 540 |
| ccctaacgaa tcactagtgc ggccgcctgc aggtcgacca tatgggagag ctcccaa | 597 |

<210> SEQ ID NO 187
<211> LENGTH: 324

```
<212> TYPE: DNA
<213> ORGANISM: Homo sapien

<400> SEQUENCE: 187
tcgttagggt ctctatccac ttgcaggtaa aatccaatcc tgtgtatatc ttatagtctt      60
ccatatgtag tggttcaaga gactgcagtt ccagaaagac tagccgagcc catccatgtc     120
ttccacttaa ccctgctttg ggttacacat cttaactttt ctgttcaagt ttctctgtgt     180
agtttatagc atgagtattg ggawaatgcc ctgaaacctg acatgagatc tgggaaacac     240
aaacttactc aataagaatt tctcccatat ttttatgatg gaaaaatttc acatgcacag     300
aggagtggat agagaccta acga                                              324

<210> SEQ ID NO 188
<211> LENGTH: 178
<212> TYPE: DNA
<213> ORGANISM: Homo sapien
<220> FEATURE:
<221> NAME/KEY: misc_feature
<222> LOCATION: (1)...(178)
<223> OTHER INFORMATION: n = A,T,C or G

<400> SEQUENCE: 188 gcgcgggat tcggggtgat acctcctcat gccaaaatac aacgtntaat ttcacaactt       60
gccttccaat ttacgcattt tcaatttgct ctccccattt gttgagtcac aacaaacacc     120
attgcccaga aacatgtatt acctaacatg cacatactct taaaactact catcccctt      178

<210> SEQ ID NO 189
<211> LENGTH: 367
<212> TYPE: DNA
<213> ORGANISM: Homo sapien

<400> SEQUENCE: 189
tgacaccttg tccagcatct gacacagtct tggctcttgg aaaatattgg ataaatgaaa      60
atgaatttct ttagcaagtg gtataagctg agaatatacg tatcacatat cctcattcta     120
agacacattc agtgtccctg aaattagaat aggacttaca ataagtgtgt tcactttctc     180
aatagctgtt attcaattga tggtaggcct taaaagtcaa agaaatgaga gggcatgtga     240
aaaaaagctc aacatcactg atcattagaa aacttccatt caaaccccca atgagatacc     300
atctcatacc agtcagaatg gctattatta aaaagtcaaa aataacaga tgctggacaa      360 ggtgtca                                                                367

<210> SEQ ID NO 190
<211> LENGTH: 369
<212> TYPE: DNA
<213> ORGANISM: Homo sapien
<220> FEATURE:
<221> NAME/KEY: misc_feature
<222> LOCATION: (1)...(369)
<223> OTHER INFORMATION: n = A,T,C or G

<400> SEQUENCE: 190
gacaccttgt ccagcatctg acaacgctaa cagcctgagg agatctttat ttatttattt      60
agtttttact ctggctaggc agatggtggc taaaacattc atttacccat ttattcattt     120
aattgttcct gcaaggccta tggatagagt attgtccagc actgctctgg aagctaggag     180
catggggatg aacaagatag gctacatcct gttcccacag aacttccact ttagtctggg     240
aaacagatga tatatacaaa tatataaatg aattcaggta gttttaagta cgaaaagaat     300
```

-continued

| | |
|---|---|
| aagaaagcag agtcatgatt tanaatgctg gaaacagggg ctattgcttg agatattgaa | 360 |
| ggtgcccaa | 369 |

<210> SEQ ID NO 191
<211> LENGTH: 369
<212> TYPE: DNA
<213> ORGANISM: Homo sapien

<400> SEQUENCE: 191

| | |
|---|---|
| tgacaccttg tccagcatct gcacagggaa aagaaactat tatcagagtg aacaggcaac | 60 |
| ctacagaatg ggagaaaatt tttgcaatct atccatctga caagggcta atatccagaa | 120 |
| tctacaaaga acttatacaa atttacaaga aacaaacaaa caacaactc ctcaaaaagt | 180 |
| gggtgaagga tgtgaacaga cacttctcaa aagaagacat ttatggggcc aacaaacata | 240 |
| tgaaaaaaag ctcatcatca ctggtcacta gataaatgca aatcaaaacc acaatgagat | 300 |
| accatctcat tccagttaga atggcaatca ttaaaaagtc aggaaacaac agatgctgga | 360 |
| caaggtgtc | 369 |

<210> SEQ ID NO 192
<211> LENGTH: 449
<212> TYPE: DNA
<213> ORGANISM: Homo sapien

<400> SEQUENCE: 192

| | |
|---|---|
| tgacgcttgg ccacttgaca cttcatcttt gcacagaaaa acttctttac agatttaatt | 60 |
| caagactggt ctagtgacag tcctccagac attttttcat ttgttccata tacgtggaat | 120 |
| tttaaaatca tgtttcatca gtttgaaatg atttgggctg ctaatcaaca caattggatc | 180 |
| gactgttcta ctaaacaaca ggaaaatgtg tatctggcag cctgtggaga aacactaaac | 240 |
| attgattttt ctttgccttt tacggacttt gttccagcta catgtaatac caagttctct | 300 |
| ttaagaggag aagatgttga tcttcatttg tttctaccag actgccaccc tagtaaatat | 360 |
| tctttattta tgctggtaaa aaattgccat ccaaataaga tgattcatga tactggtatt | 420 |
| cctgctgagt gtcaagtggc caagcgtca | 449 |

<210> SEQ ID NO 193
<211> LENGTH: 372
<212> TYPE: DNA
<213> ORGANISM: Homo sapien

<400> SEQUENCE: 193

| | |
|---|---|
| tgacgcttgg ccacttgaca ccagggatgt akcagttgaa tataatcctg caattgtaca | 60 |
| tattggcaat ttcccatcaa acattctaga aagagacaac caggattgct aggccataaa | 120 |
| agctgcaata ataactggt aattgcagta atcatttcag gccaattcaa tccagtttgg | 180 |
| ctcagaggtg cctttggctg agagaagagg tgagatataa tgtgttttct tgcaacttct | 240 |
| tggaagaata actccacaat agtctgagga ctagatacaa acctatttgc cattaaagca | 300 |
| ccagagtctg ttaattccag tactgataag tgttggagat tagactccag tgtgtcaagt | 360 |
| ggccaagcgt ca | 372 |

<210> SEQ ID NO 194
<211> LENGTH: 309
<212> TYPE: DNA
<213> ORGANISM: Homo sapien
<220> FEATURE:
<221> NAME/KEY: misc_feature

```
<222> LOCATION: (1)...(309)
<223> OTHER INFORMATION: n = A,T,C or G

<400> SEQUENCE: 194
tgacgcttgg ccacttgaca cttatgtaga atccatcgtg ggctgatgca agcccttat     60 ttaggcttag tgttgtgggc accttcaata tcacactaga gacaaacgcc acaagatctg   120
cagaaacatt cagttctgan cactcgaatg gcaggataac tttttgtgtt gtaatccttc   180
acatatacaa aaacaaactc tgcantctca cgttacaaaa aaacgtactg ctgtaaaata   240
ttaagaaggg gtaaaggata ccatctataa caaagtaact acaactagt gtcaagtggc    300 caagcgtca                                                           309

<210> SEQ ID NO 195
<211> LENGTH: 312
<212> TYPE: DNA
<213> ORGANISM: Homo sapien
<220> FEATURE:
<221> NAME/KEY: misc_feature
<222> LOCATION: (1)...(312)
<223> OTHER INFORMATION: n = A,T,C or G

<400> SEQUENCE: 195
tgacgcttgg ccacttgaca cccaatctcg cacttcatcc tcccagcacc tgatgaagta   60
ggactgcaac tatccccact tcccagatga ggggaccaan gtacacatta ggacccggat  120
gggagcacag atttgtccga tcccagactc caagcactca gcgtcactcc aggacagcgg  180
ctttcagata aggtcacaaa catgaatggc tccgacaacc ggagtcagtc cgtgctgagt  240
taaggcaatg tgacacggat gcacgtgtn acctgtaatg gttcatcgta agtgtcaagt    300
ggccaagcgt ca                                                      312

<210> SEQ ID NO 196
<211> LENGTH: 288
<212> TYPE: DNA
<213> ORGANISM: Homo sapien

<400> SEQUENCE: 196
tgtatcgacg tagtggtctc ctcagccatg cagaactgtg actcaattaa acctcttcc    60 tttatgaatt acccaatctc gggtagtgtc tttatagtag tgtgagaatg gactaataca  120 agtacattt acttagtaat aataataaac aaatatatta catttttgtg tatttactac   180
accatatttt ttattgttat tgtagtgtac accttctact tattaaaaga aataggcccg  240
aggcgggcag atcacgaggt caggagatgg agaccactac gtcgatac                288

<210> SEQ ID NO 197
<211> LENGTH: 289
<212> TYPE: DNA
<213> ORGANISM: Homo sapien

<400> SEQUENCE: 197
ttgggcacct tcaatatcat gacaggtgat gtgataacca agaaggctac taagtgatta   60
atgggtgggt aatgtataca gagtaggtac actggacaga ggggtaattc atagccaagg  120
caggagaagc agaatggcaa acatttcat cacactactc aggatagcat gcagtttaaa   180
acctataagt agtttatttt tggaattttc cacttaatat tttcagactg caggtaacta  240
aactgtggaa cacaagaaca tagataaggg gagaccacta cgtcgatac               289

<210> SEQ ID NO 198
```

<211> LENGTH: 288
<212> TYPE: DNA
<213> ORGANISM: Homo sapien

<400> SEQUENCE: 198

```
gtatcgacgt agtggtctcc caagcagtgg gaagaaaacg tgaaccaatt aaaatgtatc      60
agataccccca aagaaaggcg cttgagtaaa gattccaagt gggtcacaat ctcagatctt    120
aaaattcagg ctgtcaaaga gatttgctat gaggttgctc tcaatgactt caggcacagt    180
cggcaggaga ttgaagccct ggccattgtc aagatgaagg agctttgtgc catgtatggc    240
aagaaagacc ccaatgagcg ggactcctgg agaccactac gtcgatac                 288
```

<210> SEQ ID NO 199
<211> LENGTH: 1027
<212> TYPE: DNA
<213> ORGANISM: Homo sapien
<220> FEATURE:
<221> NAME/KEY: misc_feature
<222> LOCATION: (1)...(1027)
<223> OTHER INFORMATION: n = A,T,C or G

<400> SEQUENCE: 199

```
gcttttttggg aaaaacncaa ntgggggaaa ggggngnttnn tngcaagggg ataaaggggg     60
aancccaggg tttccccatt cagggaggtg taaaaagncg gccaggggat tgtaanagga    120
ttcaataata gggggaatgg gcccngaagt tgcaaggttc cngcccgcca tgnccgcggg    180
atttagtgac attacgacgs tggtaataaa gtgggsccaa waaatatttg tgatgtgatt    240
tttsgaccag tgaacccatt gwacaggacc tcatttccty tgagatgrta gccataatca    300
gataaaagrt tagaagtytt tctgcacgtt aacagcatca ttaaatggag tggcatcacc    360
aatttcaccc tttgttagcc gataccttcc ccttgaaggc attcaattaa gtgaccaatc    420
gtcatacgag aggggatggc atggggattg atgatgtat  cagggtgat  accttcacag    480
gtgaaaggca tatcctcttg tctatactga ataccacaag tacccttttg accatgtcga    540
ctagcaaatt tgtctccaat ctgtgtwatc cctaacagag cgtacccta ttttacaaaa    600
tttatatcct tcctgattga gagttaccat aacctgatcc acaatgcccg tctcgctwgt    660
tctgagaaaa gtgctacagt ctctcttggt atagcgtcta ttggtgctct ccaattcatc    720
ttcattttc aggcaaggtg aactgttttg cctataataa cmtcatctcc tgatacmcga    780
aacccckgga rctatcaaac catcatcatc cagcgttckt watgtymcta aatccctatt    840
gcggccgcct gcaggtcaac atatnggaaa accccccacc ccttnggagc ntaccttgaa    900
ttttccatat gtcccntaaa ttanctngnc ttancctggc ntaacctnt tccggtttaa    960
attgtttccg cccccnttcc ccnccttnna accggaaacc ttaattttna accngggggtt   1020
cctatcc                                                            1027
```

<210> SEQ ID NO 200
<211> LENGTH: 207
<212> TYPE: DNA
<213> ORGANISM: Homo sapien

<400> SEQUENCE: 200

```
agtgacatta cgacgctggc catcttgaat cctagggcat gaagttgccc caaagttcag     60
cacttggtta agcctgatcc ctctggttta tcacaaagaa taggatggga taaagaaagt    120
ggacacttaa ataagctata aattatatgg tccttgtcta gcaggagaca actgcacagg    180
tatactacca gcgtcgtaat gtcacta                                       207
```

<210> SEQ ID NO 201
<211> LENGTH: 209
<212> TYPE: DNA
<213> ORGANISM: Homo sapien

<400> SEQUENCE: 201

```
tgggcacctt caatatctat taaaagcaca aatactgaag aacacaccaa gactatcaat      60
gaggttacat ctggagtcct cgatatatca ggaaaaaatg aagtgaacat tcacagagtt     120
ttacttcttt gggaactcaa atgctagaaa agaaaagggg gccctctttc tctggcttcc     180
tggtcctatc cagcgtcgta atgtcacta                                       209
```

<210> SEQ ID NO 202
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 202

```
ntacgctgca acactgtgga gccactggtt tttattcccg gcaggttatc cagcaaacag      60
tcactgaaca caccgaagac cgtggtatgg taaccgttca cagtaatcgt tccagtcgtc     120
tgcgggaccc cgacgagcgt cactgggtac agaccagatt cagccggaag agaaagcgcc     180
gcagggagag actcgaactc cactccgctg gtgagcagcc ccatgttttc aactcgaagt     240
tcaaacggca ttgggttata taccatcagc tgaacttcac acacatctcc ttgaacccac     300
tggaaatcta ttttcttgtt ccgctcttct ccacagtgtt gcagcgtaa                 349
```

<210> SEQ ID NO 203
<211> LENGTH: 241
<212> TYPE: DNA
<213> ORGANISM: Homo sapien

<400> SEQUENCE: 203

```
tgctcctctt gccttaccaa cccaaagccc actgtgaaat atgaagtgaa tgacaaaatt      60
cagttttcaa cgcaatatag tatagtttat ctgattcttt tgatctccag gacactttaa     120
acaactgcta ccaccaccac caacctaggg atttaggatt ctccacagac cagaaattat     180
ttctcctttg agtttcaggc tcctctggga ctcctgttca tcaatgggtg gtaaatggct     240
a                                                                     241
```

<210> SEQ ID NO 204
<211> LENGTH: 248
<212> TYPE: DNA
<213> ORGANISM: Homo sapien

<400> SEQUENCE: 204

```
tagccattta ccaccatct gcaaaccswg acmwwcargr cywgwackya ggcgatttga      60
agtactggta atgctctgat catgttagtt acataagtgt ggtcagttta caaaaattca     120
cagaactaaa tactcaatgc tatgtgttca tgtctgtgtt tatgtgtgtg taatgtttca     180
attaagtttt tttaaaaaaa agagatgatt tccaaataag aaagccgtgt tggtaaggca     240
agaggagc                                                              248
```

<210> SEQ ID NO 205

```
<211> LENGTH: 505
<212> TYPE: DNA
<213> ORGANISM: Homo sapien
<220> FEATURE:
<221> NAME/KEY: misc_feature
<222> LOCATION: (1)...(505)
<223> OTHER INFORMATION: n = A,T,C or G

<400> SEQUENCE: 205
tacgctgcaa cactgtggag ccattcatac aggtccctaa ttaaggaaca agtgattatg      60
ctacctttgc acggttaggg taccgcggcc gttaaacatg tgtcactggg caggcggtgc     120
ctctaatact ggtgatgcta gaggtgatgt ttttggtaaa caggcggggt aagatttgcc     180
gagttccttt tactttttt aacctttcct tatgagcatg cctgtgttgg gttgacagtg     240
ggggtaataa tgacttgttg gttgattgta gatattgggc tgttaattgt cagttcagtg     300
ttttaatctg acgcaggctt atgcggagga gaatgttttc atgttactta tactaacatt    360
agttcttcta tagggtgata gattggtcca attgggtgtg aggagttcag ttatatgttt    420 gggattttt aggtagtggg tgttganctt gaacgctttc ttaattggtg ctgcttta       480 rgcctactat gggtggtaaa tggct                                          505

<210> SEQ ID NO 206
<211> LENGTH: 179
<212> TYPE: DNA
<213> ORGANISM: Homo sapien

<400> SEQUENCE: 206
tagactgact catgtcccct accaaagccc atgtaaggag ctgagttctt aaagactgaa     60
gacagactat tctctggaga aaataaaat ggaaattgta ctttaaaaaa aaaaaaaatc     120
ggccgggcat ggtagcacac acctgtaatc ccagctacta ggggacatga gtcagtcta    179

<210> SEQ ID NO 207
<211> LENGTH: 176
<212> TYPE: DNA
<213> ORGANISM: Homo sapien

<400> SEQUENCE: 207
agactgactc atgtccccta ccccaccttc tgctgtgctg ccgtgttcct aacaggtcac      60
agactggtac tggtcagtgg cctgggggtt ggggacctct attatatggg atacaaattt    120
aggagttgga attgacacga tttagtgact gatgggatat gggtggtaaa tggcta        176

<210> SEQ ID NO 208
<211> LENGTH: 196
<212> TYPE: DNA
<213> ORGANISM: Homo sapien

<400> SEQUENCE: 208
agactgactc atgtcccta tttaacaggg tctctagtgc tgtgaaaaaa aaaatgctg       60 aacattgcat ataacttata ttgtaagaaa tactgtacaa tgactttatt gcatctgggt    120
agctgtaagg catgaaggat gccaagaagt ttaaggaata tgggtggtaa atggctaggg    180
gacatgagtc agtcta                                                    196

<210> SEQ ID NO 209
<211> LENGTH: 345
<212> TYPE: DNA
<213> ORGANISM: Homo sapien
<220> FEATURE:
<221> NAME/KEY: misc_feature
```

```
<222> LOCATION: (1)...(345)
<223> OTHER INFORMATION: n = A,T,C or G

<400> SEQUENCE: 209
gacgcttggc cacttgacac cttttatttt ttaaggattc ttaagtcatt tangtnactt      60
tgtaagtttt tcctgtgccc ccataagaat gatagcttta aaattatgc tggggtagca      120 aagaagatac ttctagcttt agaatgtgta ggtatagcca ggattcttgt gaggaggggt      180
gatttagagc aaatttctta ttctccttgc ctcatctgta acatgggat aataatagaa      240 ctggcttgac aaggttggaa ttagtattac atggtaaata catgtaaaat gtttagaatg      300
gtgccaagta tctaggaagt acttgggcat gggtggtaaa tggct                      345

<210> SEQ ID NO 210
<211> LENGTH: 178
<212> TYPE: DNA
<213> ORGANISM: Homo sapien

<400> SEQUENCE: 210
gacgcttggc cacttgacac tagagtaggg tttggccaac ttttttctata aaggaccaga    60 gagtaaatat ttcaggcttt gtgggttgtg cagtctctct tgcaactact cagctctgcc    120
attgtagcat agaaatcagc catagacagg acagaaatga atgggtggta aatggcta      178

<210> SEQ ID NO 211
<211> LENGTH: 454
<212> TYPE: DNA
<213> ORGANISM: Homo sapien

<400> SEQUENCE: 211
tgggcacctt caatatctat ccagcgcatc taaattcgct ttttcttga ttaaaattt        60 caccacttgc tgttttttgct catgtatacc aagtagcagt ggtgtgaggc catgcttgtt   120
ttttgattcg atatcagcac cgtataagag cagtgctttg gccattaatt tatcttcatt    180
gtagacagca tagtgtagag tggtatctcc atactcatct ggaatatttg gatcagtgcc    240
atgttccagc aacattaacg cacattcatc ttcctggcat tgtacggcct ttgtcagagc    300
tgtcctcttt tgttgtcaa ggacattaag ttgacatcgt ctgtccagca cgagttttac     360
tacttctgaa ttcccattgg cagaggccag atgtagagca gtcctctttt gcttgtccct    420
cttgttcaca tcagtgtccc tgagcataac ggaa                                454

<210> SEQ ID NO 212
<211> LENGTH: 337
<212> TYPE: DNA
<213> ORGANISM: Homo sapien

<400> SEQUENCE: 212
tccgttatgc cacccagaaa acctactgga gttacttatt aacatcaagg ctggaaccta     60
tttgcctcag tcctatctga ttcatgagca catggttatt actgatcgca ttgaaaacat    120
tgatcacctg ggtttcttta tttatcgact gtgtcatgac aaggaaactt acaaactgca    180
acgcagagaa actattaaag gtattcagaa acgtgaagcc agcaattgtt tcgcaattcg    240
gcattttgaa aacaaatttg ccgtggaaac tttaatttgt tcttgaacag tcaagaaaaa    300
cattattgag gaaaattaat atcacagcat aacggaa                              337

<210> SEQ ID NO 213
<211> LENGTH: 715
<212> TYPE: DNA
```

```
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 213
tcgggtgatg cctcctcagg catcttccat ccatctcttc aagattagct gtcccaaatg      60
tttttccttc tcttctttac tgataaattt ggactccttc ttgacactga tgacagcttt     120
agtatccttc ttgtcacctt gcagacttta aacataaaaa tactcattgg ttttaaaagg     180
aaaaagtat  acattagcac tattaagctt ggccttgaaa cattttctat cttttattaa     240
atgtcggtta gctgaacaga attcatttta caatgcagag tgagaaaaga agggagctat     300
atgcatttga gaatgcaagc attgtcaaat aaacatttta aatgctttct taaagtgagc     360
acatacagaa atacattaag atattagaaa gtgtttttgc ttgtgtacta ctaattaggg     420
aagcaccttg tatagttcct cttctaaaat tgaagtagat tttaaaaacc catgtaattt     480
aattgagctc tcagttcaga ttttaggaga attttaacag ggatttggtt ttgtctaaat     540
tttgtcaatt tntttagtta atctgtataa ttttataaat gtcaaactgt atttagtccg     600
ttttcatgct gctatgaaag aaatacccan gacagggtta tttataaang gaaagangtt     660
aatttgactc ccagttcaca ggcctgagga ngnatcnccc gaaatcctta ttgcg         715

<210> SEQ ID NO 214
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 214
ggtaangngc atacntcggt gctccggccg ccggagtcgg gggattcggg tgatgcctcc      60
tcaggcccac ttgggcctgc ttttcccaaa tggcagctcc tctggacatg ccattccttc     120
tcccacctgc ctgattcttc atatgttggg tgtccctgtt tttctggtgc tatttcctga     180
ctgctgttca gctgccactg tcctgcaaag cctgcctttt taaatgcctc accattcctt     240
catttgtttc ttaaatatgg gaagtgaaag tgccacctga ggccgggcac agtggctcac     300
gcctgtaatc ccagcacttt gggagcctga ggaggcatca cccga                    345

<210> SEQ ID NO 215
<211> LENGTH: 429
<212> TYPE: DNA
<213> ORGANISM: Homo sapien

<400> SEQUENCE: 215
ggtgatgcct cctcaggcga agctcaggga ggacagaaac ctcccgtgga gcagaagggc      60
aaaagctcgc ttgatcttga ttttcagtac gaatacagac cgtgaaagcg gggcctcacg     120
atccttctga cctttggggt tttaagcagg aggtgtcaga aaagttacca cagggataac     180
tgcttgtgg  cggccaagcg ttcatagcga cgtcgctttt tgatccttcg atgtcggctc     240
ttcctatcat tgtgaagcag aattccaccaa gcgttggatt gttcacccac taatagggaa     300
cgtgagctgg gttagaccg tcgtgagaca ggttagtttt accctactga tgatgtgtkg     360
ttgccatggt aatcctgctc agtacgagag gaaccgcagg ttcasacatt tggtgtatgt     420
gcttgcctt                                                             429
```

<210> SEQ ID NO 216
<211> LENGTH: 593
<212> TYPE: DNA
<213> ORGANISM: Homo sapien
<220> FEATURE:
<221> NAME/KEY: misc_feature
<222> LOCATION: (1)...(593)
<223> OTHER INFORMATION: n = A,T,C or G

<400> SEQUENCE: 216

```
tgacacctat gtccngcatc tgttcacagt ttccacaaat agccagcctt tggccacctc      60
tctgtcctga ggtatacaag tatatcagga ggtgtatacc ttctcttctc ttccccacca     120
aagagaacat gcaggctctg gaagctgtct taggagcctt tgggctcaga atttcagagt     180
cttgggtacc ttggatgtgg tctggaagga gaaacattgg ctctggataa ggagtacagc     240
cggaggaggg tcacagagcc ctcagctcaa gcccctgtgc cttagtctaa aagcagcttt     300
ggatgaggaa gcaggttaag taacatacgt aagcgtacac aggtagaaag tgctgggagt     360
cagaattgca cagtgtgtag gagtagtacc tcaatcaatg agggcaaatc aactgaaaga     420
agaagaccna ttaatgaatt gcttangggg aaggatcaag gctatcatgg agatcttttct    480
aggaagatta ttgttttanaa ttatgaaagg antagggcag ggacagggcc agaagtanaa    540
ganaacattg cctatanccc ttgtcttgca cccagatgct ggacaaggtg tca            593
```

<210> SEQ ID NO 217
<211> LENGTH: 335
<212> TYPE: DNA
<213> ORGANISM: Homo sapien

<400> SEQUENCE: 217

```
tgacaccttg tccagcatct gacgtgaaga tgagcagctc agaggaggtg tcctggattt      60
cctggttctg tgggctccgt ggcaatgaat tcttctgtga agtggatgaa gactacatcc     120
aggacaaatt taatcttact ggactcaatg agcaggtccc tcactatcga caagctctag     180
acatgatctt ggacctggag cctgatgaag aactggaaga caaccccaac cagagtgacc     240
tgattgagca ggcagccgag atgctttatg gattgatcca cgcccgctac atccttacca     300
accgtggcat cgcccagatg ctggacaagg tgtca                                 335
```

<210> SEQ ID NO 218
<211> LENGTH: 248
<212> TYPE: DNA
<213> ORGANISM: Homo sapien

<400> SEQUENCE: 218

```
tacgtactgg tcttgaaggt cttaggtaga gaaaaaatgt gaatatttaa tcaaagacta      60
tgtatgaaat gggactgtaa gtacagaggg aagggtggcc cttatcgcca gaagttggta     120
gatgcgtccc cgtcatgaaa tgttgtgtca ctgcccgaca tttgccgaat tactgaaatt     180
ccgtagaatt agtgcaaatt ctaacgttgt tcatctaaga ttatggttcc atgtttctag     240
tactttta                                                              248
```

<210> SEQ ID NO 219
<211> LENGTH: 530
<212> TYPE: DNA
<213> ORGANISM: Homo sapien
<220> FEATURE:
<221> NAME/KEY: misc_feature
<222> LOCATION: (1)...(530)

<223> OTHER INFORMATION: n = A,T,C or G

<400> SEQUENCE: 219

| | |
|---|---|
| tgacgcttgg ccacttgaca caagtagggg ataaggacaa agacccatna ggtggcctgt | 60 |
| cagccttttg ttactgttgc ttccctgtca ccacggcccc ctctgtaggg gtgtgctgtg | 120 |
| ctctgtggac attggtgcat tttcacacat accattctct ttctgcttca cagcagtcct | 180 |
| gaggcgggag cacacaggac taccttgtca gatgangata atgatgtctg gccaactcac | 240 |
| ccccaacct tctcactagt tatangaaga gccangccta naaccttcta tcctgnccc | 300 |
| ttgccctatg acctcatccc tgttccatgc cctattctga tttctggtga actttggagc | 360 |
| agcctggttt ntcctcctca ctccagcctc tctccatacc atggtangg ggtgctgttc | 420 |
| cacncaaaag gtcaggtgtg tctggggaat cctnananct gccnggagtt tccnangcat | 480 |
| tcttaaaaac cttcttgcct aatcanatng tgtccagtgg ccaaccntcn | 530 |

<210> SEQ ID NO 220
<211> LENGTH: 531
<212> TYPE: DNA
<213> ORGANISM: Homo sapien

<400> SEQUENCE: 220

| | |
|---|---|
| tgacgcttgg ccacttgaca ctaaatagca tcttctaaag gcctgattca gagttgtgga | 60 |
| aaattctccc agtgtcaggg attgtcagga acagggctgc tcctgtgctc actttacctg | 120 |
| ctgtgttct gctggaaaag gagggaagag gaatggctga tttttaccta atgtctccca | 180 |
| gttttttcata ttcttcttgg atcctcttct ctgacaactg ttcccttttg gtcttcttct | 240 |
| tcttgctcag agagcaggtc tctttaaaac tgagaaggga gaatgagcaa atgattaaag | 300 |
| aaaacacact tctgaggccc agagatcaaa tattaggtaa atactaaacc gcttgcctgc | 360 |
| tgtggtcact tttctcctct ttcacatgct ctatccctct atcccccacc tattcatatg | 420 |
| gcttttatct gccaagttat ccggcctctc atcaaccttc tcccctagcc tactggggga | 480 |
| tatccatctg ggtctgtctc tggtgtattg gtgtcaagtg gccaagcgtc a | 531 |

<210> SEQ ID NO 221
<211> LENGTH: 530
<212> TYPE: DNA
<213> ORGANISM: Homo sapien

<400> SEQUENCE: 221

| | |
|---|---|
| attgacgctt ggccacttga cacccgcctg cctgcaatac tggggcaagg gccttcactg | 60 |
| ctttcctgcc accagctgcc actgcacaca gagatcagaa atgctaccaa ccaagactgt | 120 |
| tggtcctcag cctctctgag gagaaagagc agaagcctgg aagtcagaag agaagctaga | 180 |
| tcggctacgg ccttggcagc cagcttcccc acctgtggca ataaagtcgt gcatggctta | 240 |
| acaatggggg cacctcctga gaaacacatt gttaggcaat tcggcgtgtg ttcatcagag | 300 |
| catatttaca caaacctcga tagtgcagcc tactatccac tattgctcct acgctgcaaa | 360 |
| cctgaacagc atgggactgt actgaatact ggaagcagct ggtgatggta cttatttgtg | 420 |
| tatctaaaca cagagaaggt acagtaagaa tatggtatca taaacttaca gggaccgcca | 480 |
| tcctatatgc agtctgttgt gaccaaaatg tgtcaagtgg ccaagcgtca | 530 |

<210> SEQ ID NO 222
<211> LENGTH: 578
<212> TYPE: DNA
<213> ORGANISM: Homo sapien

```
<220> FEATURE:
<221> NAME/KEY: misc_feature
<222> LOCATION: (1)...(578)
<223> OTHER INFORMATION: n = A,T,C or G

<400> SEQUENCE: 222
tgtatcgacg tagtggtctc cgggctacta ggccgttgtg tgctggtagt acctggttca      60
ctgaaaggcg catctccctc cccgcgtcgc cctgaagcag ggggaggact tcgcccagcc     120
aaggcagttg tatgagtttt agctgcggca cttcgagacc tctgagccca cctccttcag     180
gagccttccc cgattaagga agccagggta aggattcctt cctcccccag acaccacgaa     240
caaaccacca ccccccctat tctggcagcc catatacatc agaacgaaac aaaaataaca     300
aataaacnaa aaccaaaaaa aaaagagaag gggaaatgta tatgtctgtc catcctgttg     360
ctttagcctg tcagctccta nagggcaggg accgtgtctt ccgaatggtc tgtgcagcgc     420
cgactgcggg aagtatcgga ggaggaagca gagtcagcag aagttgaacg gtgggcccgg     480
cggctcttgg gggctggtgt tgtacttcga gaccgctttc gcttttttgtc ttagatttac     540 gtttgctctt tggagtggga naccactacn tcnataca                             578

<210> SEQ ID NO 223
<211> LENGTH: 578
<212> TYPE: DNA
<213> ORGANISM: Homo sapien

<400> SEQUENCE: 223
tgtatcgacg tagtggtctc ctcttgcaaa ggactggctg gtgaatggtt tccctgaatt      60
atggacttac cctaaacata tcttatcatc attaccagtt gcaaaatatt agaatgtgtt     120
gtcactgttt catttgattc ctagaaggtt agtcttagat atgttacttt aacctgtatg     180
ctgtagtgct ttgaatgcat ttttttgtttg cattttttgtt tgcccaacct gtcaattata     240
gctgcttagg tctggactgt cctggataaa gctgttaaaa tattcaccag tccagccatc     300
ttacaagcta attaagtcaa ctaaatgctt ccttgttttg ccagacttgt tatgtcaatc     360
ctcaatttct gggttcattt tgggtgccct aaatcttagg gtgtgacttt cttagcatcc     420
tgtaacatcc attcccaagc aagcacaact tcacataata cttttccagaa gttcattgct     480 gaagcctttc cttcacccag cggagcaact tgattttcta caacttccct catcagagcc     540
acaagagtat gggatatgga gaccactacg tcgataca                             578

<210> SEQ ID NO 224
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 224
tgtatcgacg tantggtctc ccaaggtgct gggattgcag gcatgagcca ccactcccag      60
gtggatcttt ttcttttatac ttacttcatt aggtttctgt tattcaagaa gtgtagtggt     120
aaagtctttt tcaatctaca tggttaaata atgatagcct gggaaataaa tagaaatttt     180
ttctttcatc tttaggttga ataaagaaac agaaaaaata gaacatactg aaaataatct     240
aagttccaac catagaagaa ctgcagaaga aatgaagaaa gtgatgatga tttagatttt     300
gatattgatt tagaagacac aggaggagac cactacgtcg ataca                     345
```

<210> SEQ ID NO 225
<211> LENGTH: 347
<212> TYPE: DNA
<213> ORGANISM: Homo sapien

<400> SEQUENCE: 225

| | | | | | |
|---|---|---|---|---|---|
| tgtatcgacg | tagtggtctc | caaactgagg | tatgtgtgcc | actagcacac | aaagccttcc | 60 |
| aacagggacg | caggcacagg | cagtttaaag | ggaatctgtt | tctaaattaa | tttccacctt | 120 |
| ctctaagtat | tctttcctaa | aactgatcaa | ggtgtgaagc | ctgtgctctt | tcccaactcc | 180 |
| cctttgacaa | cagccttcaa | ctaacacaag | aaaaggcatg | tctgacactc | ttcctgagtc | 240 |
| tgactctgat | acgttgttct | gatgtctaaa | gagctccaga | acaccaaagg | gacaattcag | 300 |
| aatgctggtg | tataacagac | tccaatggag | accactacgt | cgataca | | 347 |

<210> SEQ ID NO 226
<211> LENGTH: 281
<212> TYPE: DNA
<213> ORGANISM: Homo sapien
<220> FEATURE:
<221> NAME/KEY: misc_feature
<222> LOCATION: (1)...(281)
<223> OTHER INFORMATION: n = A,T,C or G

<400> SEQUENCE: 226

| | | | | | |
|---|---|---|---|---|---|
| aggngnggga | ntgtatcgac | gtagtggtct | cccaacagtc | tgtcattcag | tctgcaggtg | 60 |
| tcagtgtttt | ggacaatgag | gcaccattgt | cacttattga | ctcctcagct | ctaaatgctg | 120 |
| aaattaaatc | ttgtcatgac | aagtctggaa | ttcctgatga | ggttttacaa | agtattttgg | 180 |
| atcaatactc | caacaaatca | gaaagccaga | agaggatcc | tttcaatatt | gcagaaccac | 240 |
| gagtggattt | acacacctca | ggagaccact | acgtcgatac | a | | 281 |

<210> SEQ ID NO 227
<211> LENGTH: 3646
<212> TYPE: DNA
<213> ORGANISM: Homo sapien

<400> SEQUENCE: 227

| | | | | | |
|---|---|---|---|---|---|
| gggaaacact | tcctcccagc | cttgtaaggg | ttggagccct | ctccagtata | tgctgcagaa | 60 |
| ttttctctc | ggtttctcag | aggattatgg | agtccgcctt | aaaaaaggca | agctctggac | 120 |
| actctgcaaa | gtagaatggc | caaagtttgg | agttgagtgg | cccccttgaag | ggtcactgaa | 180 |
| cctcacaatt | gttcaagctg | tgtggcgggt | tgttactgaa | actcccggcc | tccctgatca | 240 |
| gtttccctac | attgatcaat | ggctgagttt | ggtcaggagc | accccttccg | tggctccact | 300 |
| catgcaccat | tcataatttt | acctccaagg | tcctcctgag | ccagaccgtg | ttttcgcctc | 360 |
| gaccctcagc | cggttcggct | cgccctgtac | tgcctctctc | tgaagaagag | gagagtctcc | 420 |
| ctcacccagt | cccaccgcct | taaaaccagc | ctactccctt | agggtcatcc | catgtctcct | 480 |
| cggctatgtc | ccctgtaggc | tcatcaccca | ttgcctcttg | gttgcaaccg | tggtgggagg | 540 |
| aagtagcccc | tctactacca | ctgagagagg | cacaagtccc | tctgggtgat | gagtgctcca | 600 |
| cccccttcct | ggtttatgtc | ccttctttct | acttctgact | tgtataattg | gaaaacccat | 660 |
| aatcctccct | tctctgaaaa | gccccaggct | ttgacctcac | tgatggagtc | tgtactctgg | 720 |
| acacattggc | ccacctggga | tgactgtcaa | cagctccttt | tgacccttt | cacctctgaa | 780 |
| gagagggaaa | gtatccaaag | agaggccaaa | agtacaaccc | tcacatcaac | caataggccg | 840 |
| gaggaggaag | ctagaggaat | agtgattaga | gacccaattg | ggacctaatt | gggacccaaa | 900 |

```
tttctcaagt ggagggagaa cttttgacga tttccaccgg tatctcctcg tgggtattca    960
gggagctgct cagaaaccta taaacttgtc taaggcgact gaagtcgtcc agggcatga   1020
tgagtcacca ggagtgtttt tagagcacct ccaggaggct tatcagattt acacccttt   1080
tgacctggca gcccccgaaa atagccatgc tcttaatttg gcatttgtgg ctcaggcagc   1140
cccagatagt aaaaggaaac tccaaaaact agagggattt tgctggaatg aataccagtc   1200
agcttttaga gatagcctaa aaggtttttg acagtcaaga ggttgaaaaa caaaaacaag   1260
cagctcaggc agctgaaaaa agccactgat aaagcatcct ggagtatcag agtttactgt   1320
tagatcagcc tcatttgact tcccctccca catggtgttt aaatccagct acactacttc   1380
ctgactcaaa ctccactatt cctgttcatg actgtcagga actgttggaa actactgaaa   1440
ctggccgacc tgatcttcaa aatgtgcccc taggaaaggt ggatgccacc atgttcacag   1500
acagtagcag cttcctcgag aagggactac gaaaggccgg tgcagctgtt accatggaga   1560
cagatgtgtt gtgggctcag gctttaccag caaacacctc agcacaaaag ctgaattga   1620
tcgccctcac tcaggctctc cgatgggta aggatattaa cgttaacact gacagcaggt   1680
acgcctttgc tactgtgcat gtacgtggag ccatctacca ggagcgtggg ctactcacct   1740
cagcaggtgg ctgtaatcca ctgtaaagga catcaaaagg aaaacacggc tgttgcccgt   1800
ggtaaccaga aagctgattc agcagctcaa gatgcagtgt gactttcagt cacgcctcta   1860
aacttgctgc ccacagtctc ctttccacag ccagatctgc ctgacaatcc cgcatactca   1920
acagaagaag aaaactggcc tcagaactca gagccaataa aaatcaggaa ggttggtgga   1980
ttcttcctga ctctagaatc ttcataccc gaactcttgg gaaaacttta atcagtcacc   2040
tacagtctac cacccattta ggaggagcaa agctacctca gctcctccgg agccgtttta   2100
agatccccca tcttcaaagc ctaacagatc aagcagctct ccggtgcaca acctgcgccc   2160
aggtaaatgc caaaaaggt cctaaaccca gcccaggcca ccgtctccaa gaaaactcac   2220
caggagaaaa gtgggaaatt gactttacag aagtaaaacc acaccgggct gggtacaaat   2280
accttctagt actggtagac accttctctg gatggactga agcatttgct accaaaaacg   2340
aaactgtcaa tatggtagtt aagttttttac tcaatgaaat catccctcga catgggctgc   2400
ctgtttgcca tagggtctga taatggaccg gccttcgcct tgtctatagt ttagtcagtc   2460
agtaaggcgt taaacattca atggaagctc cattgtgcct atcgacccca gagctctggg   2520
caagtagaac gcatgaactg caccctaaaa aacactctta caaaattaat cttagaaacc   2580
ggtgtaaatt gtgtaagtct ccttcctta gccctactta gagtaaggtg cacccttac   2640
tgggctgggt tcttaccttt tgaaatcatg tatgggaggg tgctgcctat cttgcctaag   2700
ctaagagatg cccaattggc aaaaatatca caaactaatt tattacagta cctacagtct   2760
ccccaacagg tacaagatat catcctgcca cttgttcgag gaacccatcc caatccaatt   2820
cctgaacaga cagggccctg ccattcattc ccgccaggtg acctgttgtt tgttaaaaag   2880
ttccagagag aaggactccc tcctgcttgg aagagacctc acaccgtcat cacgatgcca   2940
acggctctga agtggatgg cattcctgcg tggattcatc actcccgcat caaaaaggcc   3000
aacagagccc aactagaaac atgggtcccc agggctgggt caggcccctt aaaactgcac   3060
ctaagttggg tgaagccatt agattaattc ttttcttaa ttttgtaaaa caatgcatag   3120
cttctgtcaa acttatgtat cttaagactc aatataaccc ccttgttata actgaggaat   3180
caatgatttg attcccccaa aaacacaagt ggggaatgta gtgtccaacc tggttttac   3240
```

```
taaccctgtt tttagactct cccttttcctt taatcactca gcttgttcc acctgaattg    3300 actctccctt agctaagagc gccagatgga ctccatcttg gctctttcac tggcagccgc    3360
ttcctcaagg acttaacttg tgcaagctga ctcccagcac atccaagaat gcaattaact    3420
gataagatac tgtggcaagc tatatccgca gttcccagga attcgtccaa ttgatcacag    3480 ccccctctacc cttcagcaac caccaccctg atcagtcagc agccatcagc accgaggcaa    3540
ggccctccac cagcaaaaag attctgactc actgaagact tggatgatca ttagtatttt    3600
tagcagtaaa gttttttttt cttttctttt cttttttct cgtgcc                   3646

<210> SEQ ID NO 228
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 228
taagagggta caagatctaa gcacagccgt caatgcagaa cacagaacgt agcctggtaa     60
gtgtgttaag agtgggaatt tttggagtac agagtaaggc acctaaccct agctggggtt    120
tggtgacggt cccagatggc ttacagaaga aagtgtcctg agatgagttt ttaagaatga    180
ataaggatag acacaagtga ggactgactt ggcagtggtg aatggtgggt ggcaaaaaac    240
ttcgcatgta tggaaactgc acgtacagga atgaagaatg agactgtgtg gtgtttaatg    300
agctgcaaat actaatttta tcctgaaagt tttgaagagt taactaaaaa gtatttttta    360
gtaaggaaat aaccctacat ttcagggtta ttgtttgttt anatattgaa ggtgcccaa     419

<210> SEQ ID NO 229
<211> LENGTH: 148
<212> TYPE: DNA
<213> ORGANISM: Homo sapien

<400> SEQUENCE: 229
aagagggtac ctgtatgtag ccatggtggc aatgagagac tgattactac ctgctggaga     60
ttgtttaagt gagttaatat attaaggata aagggagcca ggtttttttga ctgttggaga    120 aggaaattac agatattgaa ggtcccaa                                         148

<210> SEQ ID NO 230
<211> LENGTH: 257
<212> TYPE: DNA
<213> ORGANISM: Homo sapien

<400> SEQUENCE: 230
taagagggta cmaaaaaaaa aaaatagaac gaatgagtaa gacctactat ttgatagtac     60
aacagggtga ctatagtcaa tgataactta attatacatt taacatagag tgtaattgga    120
ttgtttgtaa ctcgaaggat aaatgcttga gaggatggat accccattct ccatgatgta    180
cttatttcac attacatgcc tgtatcaaag catctcatat accctataaa tatgtacacc    240
tactatgtac cctctta                                                   257

<210> SEQ ID NO 231
<211> LENGTH: 260
<212> TYPE: DNA
<213> ORGANISM: Homo sapien

<400> SEQUENCE: 231
```

```
taagagggta cgggtatttg ctgatgggat ttttttttct ttcttttct ttggaaaaca    60 aaatgaaagc cagaacaaaa ttattgaaca aaagacaggg actaaatctg gagaaatgaa   120
gtcccctcac ctgactgcca tttcattcta tctgaccttc cagtctaggt taggagaata   180
gggggtggag gggattaatc tgatacaggt atatttaaag caactctgca tgtgtgccag   240
aagtccatgg taccctctta                                              260
```

<210> SEQ ID NO 232
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 232

```
tgctcctctt gccttaccaa ccacaaatta gaaccataat gagatgtcac ctcatacctg    60
gtgggattaa cattatttaa aaaatcagaa gtattgacaa ggatgtgaag aaattagaac   120
atctgtgcac tgttggtggg aatgtaaaaa aggtgtggcc actatgggta acagcatgaa   180
ggttcctcaa aaaaaatttt ttttaatcta ctctatgatc gatcttgagg ttgtttatgc   240
aaaagaactg aaatcaggat tttgaggaaa tattcacatt cccacatcca tttctgcttt   300
attcataata ctcaagagat ggaaacaacc taaatgtcca tcccgggatg aatggataaa   360
cacagtgtgg tatatgcata caatggaata ttatttagtc tttaaaaaga aaaattctat   420
catatactac aacttanatn aaccttgagg acacaatgct nagtgaaata agccacggaa   480
ggacgaatac tgcattattc ccttatatga agtatctaaa gtggtcaaac tcttanagca   540
naaagtaaaa atgggtggtt gccanacagt tggttaggcn agaaganaan cctant       596
```

<210> SEQ ID NO 233
<211> LENGTH: 96
<212> TYPE: DNA
<213> ORGANISM: Homo sapien

<400> SEQUENCE: 233

```
tcttctgaag acctttcgcg actcttaagc tcgtggttgg taaggcaaga ggagcgttgg    60
taaggcaaga ggagcgttgg taaggcaaga ggagca                              96
```

<210> SEQ ID NO 234
<211> LENGTH: 313
<212> TYPE: DNA
<213> ORGANISM: Homo sapien

<400> SEQUENCE: 234

```
tgtaagtcga gcagtgtgat gataaaactt gaatggatca atagttgctt cttatggatg    60
agcaaagaaa gtagtttctt gtgatggaat ctgctcctgg caaaaatgct gtgaacgttg   120
ttgaaaagac aacaaagagt ttagagtagt acataaattt agaatagtac ataaacttag   180
aatagtacat aaacttagta cataaataat gcacgaagca ggggcagggc ttgagagaat   240
tgacttcaat ttggaaagag tatctactgt aggttagatg ctctcaaaca gcatcacact   300
gctcgactta caa                                                     313
```

<210> SEQ ID NO 235
<211> LENGTH: 550
<212> TYPE: DNA

```
<213> ORGANISM: Homo sapien

<400> SEQUENCE: 235
aacgaggaca gatccttaaa aagaatgttg agtgaaaaaa gtagaaaata agataatctc      60
caaagtccag tagcattatt taaacatttt taaaaaatac actgataaaa attttgtaca     120
tttcccaaaa atacatatgg aagcacagca gcatgaatgc ctatgggrtt gaggataggg     180
gttgggagta gggatgggga taaaggggga aaataaaacc agagaggagt cttacacatt     240
tcatgaacca aggagtataa ttatttcaac tatttgtacc wgaagtccag aaagagtgga     300
ggcagaaggg ggagaagagg gcgaagaaac gttttggga gagggtccc asaagagaga       360 ttttcgcgat gtggcgctac atacgttttt ccaggatgcc ttaagctctg caccctattt     420
ttctcatcac taatattaga ttaaaccctt tgaagacagc gtctgtggtt tctctacttc     480
agctttccct ccgtgtcttg cacacagtag ctgttttaca agggttgaac tgactgaagt     540
gagattattc                                                           550

<210> SEQ ID NO 236
<211> LENGTH: 325
<212> TYPE: DNA
<213> ORGANISM: Homo sapien

<400> SEQUENCE: 236
tagactgact catgtcccct accagagtag ctagaattaa tagcacaagc ctctacaccc      60
aggaactcac tattgaatac ataaatggaa tttattcagc cttaaaaagt ttggaaggaa     120
attctgacat atgctaaaac atggatgaac cttgaagact ttatgataag taaagaagc      180 cagtcataaa aggaaaaata ttgcatgatt ccacttatat gaggtaccta gagtagtcaa     240
tttcatagaa acacaaaata gaatggtgtt tgccagggct tttgaggaaa agggaatgac     300
aagttagggg acatgagtca gtcta                                         325

<210> SEQ ID NO 237
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 237
tagactgact catgtcccct atctactcaa catttccact tgaagtctga taggcatctc      60
agacttatct tgtcccaaag caaactcttt atttcttttc atcctagtct ttatttcttg     120
tgctgtctta cccatctcaa aagagtgcca aaatccacca agttgctgaa acagaaatct     180
aagaaatatc cttgattctt cttttccca tctacttcac ttctaattca ttagtaaata     240
atctgtttca gaaaaccaaa cacctcatgt tctcactcat aagggggagt tgaacaatga     300
gaacacacag acacagggag gggaacatca cacaccacgg cccgtcaggg agtangggac     360
atgagtcagt cta                                                      373

<210> SEQ ID NO 238
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G
```

<400> SEQUENCE: 238

```
tagactgact catgtcccct ataatgctcc caggcatcag aaagcatctc aaactggagc      60
tgacaccatg gcagaggttt caggtaagtc acaaaagggg tcctaaagaa tttgccctca     120
atatcagagt gattagaaga agtggacaga gctacccaag ttaaacatat gcgagataaa     180
aaaaatatgg cacttgtgaa cacacactac aggaggaaaa taaggaacat aatagcatat     240
tgtgctatta tgatgatgaa gaacctctct anaagaaaac ataaccaaag aaacaaagaa     300
aattcctgcn aatgtttaat gctatagaag aaattaacaa aaacatatat tcaatgaatt     360
cagaaaagtt agcaggtcan aagaaaacaa atcaaagacc agaataatcc cattttagat     420
tgtcgagtaa actanaacag aaagaatacc actggaaatt gaattcctac gtangggaca     480
tgantcantc ta                                                         492
```

<210> SEQ ID NO 239
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 239

```
tggaaagtat ttaatgatgg gcaacttgct gtttacttcc tacatatccc atcatcttct      60
gtatttttt aaataacttt tttttggatt tttaaagtaa ccttattctg agaggtaaca     120
tggattacat acttctaagc cattaggaga ctctatgtta aaccaaaagg aaatgttact     180
agatcttcat ttgatcaata ggatgtgata atcatcatct ttctgctcta atggaaaagt     240
actanaaaca tggaaccata atcttagatg aacaacgtta gaatttgcac taattctacg     300
gaatttcagt aattcggcaa atgtcgggca gtgacacaac atttcatgac ggggacgcat     360
ctaccaactt ctggcgataa gggccaccct tccctctgta cttacagtcc catttcatac     420
acagtctttg attaaatatt cacattttt ctctacctaa agaccttcaa gaccagtacg     480
ta                                                                   482
```

<210> SEQ ID NO 240
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 240

```
tgtatcgacg tagtggtctc cccatgtgat agtctgaaat atagcctcat gggatgagag      60
gctgtgcccc agcccgacac ccgtaaaggg tctgtgctga ggtggattag taaaagagga     120
aagccttgca gttgagatag aggaagggca ctgtctcctg cctgccctg ggaactgaat     180
gtctcggtat aaaacccgat tgtacatttg ttcaattctg agataggaga aaaaccaccc     240
tatggcggga ggcgagacat gttggcagca atgctgcctt gttatgcttt actccacaga     300
tgtttgggcg gagggaaaca taaatctggc ctacgtgcac atccaggcat agtacctccc     360
tttgaactta attatgacac agattccttt gctcacatgt tttttgctg accttctcct     420
tattatcacc ctgctctcct accgcattcc ttgtgctgag ataatgaaaa taatatcaat     480
```

```
aaaaacttga nggaactcgg agaccactac gtcgataca                              519
```

<210> SEQ ID NO 241
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 241

```
tgtatcgacg tagtggtctc cactcccgcc ttgacggggc tgctatctgc cttccaggcc       60
actgtcacgg ctcccgggta gaagtcactt atgagacaca ccagtgtggc cttgttggct     120
tgaagctcct cagaggaggg tgggaacaga gtgaccgagg gggcagcctt gggctgacct     180
aggacggtca gcttggtccc tccgccaaac acgagagtgc tgctgcttgt atatgagctg     240
cagtaataat cagcctcgtc ctcagcctgg agcccagaga tggtcaggga ggccgtgttg     300
ccanacttgg agccagagaa gcgattagaa accccctgagg gccgattacc gacctcataa     360
atcatgaatt tggggctttt gcctgggtgc tgttggtacc angagacatt attataacca     420
ccaacgtcac tgctggttcc antgcaggga aaatggttga tcnaactgtc caagaaaacc     480
actacgtcca taccaatcca ctaattgccn gccgcctgca ggttcaacca tattggggaa     540
naactcccn ccgccgtttg ggattgncat naaccttttga aatttttttcc tattanttgt     600
ccccctaaaa taaaccnttg ggcnttaatc cattgggtcc atancttntt tncccggttt     660
ttaaaanttg tttatcccgc cncccnattt cccccccaac tttccaaaac ccgaaaccnt     720
tnaaatttnt tnaaaccctg gggggttccc nnaattnnan ttnaanctnc c               771
```

<210> SEQ ID NO 242
<211> LENGTH: 167
<212> TYPE: DNA
<213> ORGANISM: Homo sapien

<400> SEQUENCE: 242

```
tgggcaccttt caatatcggg ctcatcgata acatcacgct gctgatgctg ctgttgctgg     60
tcctctctag gaacctctgg attttcaaat tctttgagga attcatccaa attatctgcc     120
tctcctcctt tcctccttttt tctaaggtct tctggtacaa gcggtca                  167
```

<210> SEQ ID NO 243
<211> LENGTH: 338
<212> TYPE: DNA
<213> ORGANISM: Homo sapien

<400> SEQUENCE: 243

```
ttgggcacct tcaatatcta ctgatctaaa tagtgtggtt tgaggcctct tgttcctggc      60
taaaaatcct tggcaagagt caatctccac tttacaatag aggtaaaaat cttacaatgg    120
atattcttga caaagctagc atagagacag caatttttaca caaggtatttt ttcacctgtt    180
taataacagt ggttttccta caccccatagg gtgccaccaa gggaggagtg cacagttgca    240
gaaacaaatt aagatactga agacaacact acttaccatt tcccgtatag ctaaccacca    300
gttcaactgt acatgtatgt tcttatgggc aatcaaga                             338
```

<210> SEQ ID NO 244
<211> LENGTH: 346
<212> TYPE: DNA
<213> ORGANISM: Homo sapien

<400> SEQUENCE: 244

```
tttttggctc ccatacagca cactctcatg ggaaatgtct gttctaaggt caacccataa      60
tgcaaaaatc atcaatatac ttgaagatcc ccgtgtaagg tacaatgtat ttaatattat     120
cactgataca attgatccaa taccagtttt agtctggcat tgaatcaaat cactgttttt     180
gttgtataaa aagagaaata tttagcttat atttaagtac catattgtaa gaaaaaagat    240
gcttatcttt acatgctaaa atcatgatct gtacattggt gcagtgaata ttactgtaaa    300
agggaagaag gaatgaagac gagctaagga tattgaaggt gcccaa                    346
```

<210> SEQ ID NO 245
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 245

```
accaatccca cacggatact gagggacaag tatatcatcc catttcatcc ctacagcagc      60
aacttcatga ggcaggagtt attagtccca ttttacagaa gaggaaactg agacttaggg    120
agatcaagta atttgcccag gtcgcacaat tagtgataga gccagggctt gaagcgacgt    180
ctgtcttaag ccaatgaccc ctgcagatta ttagagcaac tgttctccac aacagtgtaa    240
gcctcttgct anaagctcag gtccacaagg gcagagattt ttgtctgttt tgctcattgc    300
tccttcccca ttgcttagag cagggtctgc cacgaancag gttctcaatg catagttatt    360
aaatgtatat aagagcaaac atatgttaca gagaactttc tgtatgcttg tcacttacat    420
gaatcacctg tganatgggt atgcttgttc cccantgttg cagatnaaga tattgaangt    480
gcccaaatca ctanttgcgg gcgcctgcan gtccancata t                         521
```

<210> SEQ ID NO 246
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 246

```
tggaaccaat ccaaataccc atcaatgata gactggataa agaaaatttg gcacatgttc      60
accatgaaat actatgcagc cataaaaaag gatgagttca tatcctttgc agggacatgg    120
atgaagctgg agaccatcat tctcagcaaa ctaacaaggg aacagaaaac caaacactgc    180
atgttctcac tcttaagtgg gagctgaaca atgaaacac atggacacag ggaggggaac    240
atcacacagt ggggcctgct ggtgggtagg ggtctagggg agggatagca ttaggagaaa    300
tacctaatgt agatgacggg ttgatgggtg cagcaaacca ccatgacacg tgtataccta    360
tgtaacaaac ctgcatgttc tgcacatgta ccccagaact taaagtgtta ataaaaaaat    420
taagaaaaaa gttaagtatg tcatagatac ataaaatatt gtanatattg aaggtgccca    480
aa                                                                    482
```

<210> SEQ ID NO 247
<211> LENGTH: 474
<212> TYPE: DNA

<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 247

| | | | | | |
|---|---|---|---|---|---|
| ttcgatacag | gcacagagta | agcagaaaaa | tggctgtggt | ttaaccaagt | gagtacagtt | 60 |
| aagtgagaga | ggggcagaga | agacaagggc | atatgcaggg | ggtgattata | acaggtggtt | 120 |
| gtgctgggaa | gtgagggtac | tcggggatga | ggaacagtga | aaaagtggca | aaaagtggta | 180 |
| agatcagtga | attgtacttc | tccagaattt | gatttctggn | ggagtcaaat | aactatccag | 240 |
| tttggggtat | catanggcaa | cagttgaggt | ataggaggta | gaagtcncag | tgggataatt | 300 |
| gaggttatga | anggtttggt | actgactggt | actgacaang | tctgggttat | gaccatggga | 360 |
| atgaatgact | gtanaagcgt | anaggatgaa | actattccac | ganaaagggg | tccnaaaact | 420 |
| aaaaannnaa | gnnnnngggg | aatattattt | atgtggatat | tgaangtgcc | caaa | 474 |

<210> SEQ ID NO 248
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 248

| | | | | | |
|---|---|---|---|---|---|
| ttcgatacag | gcaaacatga | actgcaggag | ggtggtgacg | atcatgatgt | tgccgatggt | 60 |
| ccggatggnc | acgaagacgc | actggancac | gtgcttacgt | ccttttgctc | tgttgatggc | 120 |
| cctgagggga | cgcaggaccc | ttatgaccct | cagaatcttc | acaacgggag | atggcactgg | 180 |
| attgantccc | antgacacca | gagacacccc | aaccaccagn | atatcantat | attgatgtag | 240 |
| ttcctgtaga | nggccccctt | gtggaggaaa | gctccatnag | ttggtcatct | tcaacaggat | 300 |
| ctcaacagtt | tccgatggct | gtgatgggca | tagtcatant | taaccntgtn | tcgaa | 355 |

<210> SEQ ID NO 249
<211> LENGTH: 434
<212> TYPE: DNA
<213> ORGANISM: Homo sapien

<400> SEQUENCE: 249

| | | | | | |
|---|---|---|---|---|---|
| ttggattggt | cctccaggag | aacaagggga | aaaaggtgac | cgagggctcc | ctggaactca | 60 |
| aggatctcca | ggagcaaaag | gggatggggg | aattcctggt | cctgctggtc | ccttaggtcc | 120 |
| acctggtcct | ccaggcttac | caggtcctca | aggcccaaag | ggtaacaaag | gctctactgg | 180 |
| acccgctggc | cagaaaggtg | acagtggtct | tccagggcct | cctgggcctc | cagtccacc | 240 |
| tggtgaagtc | attcagcctt | taccaatctt | gtcctccaaa | aaaacgagaa | gacatactga | 300 |
| aggcatgcaa | gcagatgcag | atgataatat | tcttgattac | tcggatggaa | tggaagaaat | 360 |
| atttggttcc | ctcaattccc | tgaaacaaga | catcgagcat | atgaaatttc | caatgggtac | 420 |
| tcagaccaat | ccaa | | | | | 434 |

<210> SEQ ID NO 250
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 250

```
tggattggtc acatggcaga gacaggattc caaggcagtg agaggaggat acaatgcttc      60
tcactagtta ttattattta ttttattttt gagatgaagt ctcgctttgt ctcccaggct     120
ggagagcggt ggtgcgatct tggctctctg caaccccgc ctcaagcaat tctcctgtct      180
tagcctcgcg ggtagatgga attacaggcg cccaccgcca tgcccaacta atttttttgt     240
gtcttcagta gagacagggt ttcgccatgt tgggcaggct ggtcttgaac tcctgacctc     300
nagtgatctg ccctcctcgg cctcacaaag tgctggaatt acaggcatgg gctgctgcac     360
ccagtcaact tctcactagt tatggcctta tcattttcac cacattctat tggcccaaaa     420
aaaaaaaaan                                                            430
```

<210> SEQ ID NO 251
<211> LENGTH: 329
<212> TYPE: DNA
<213> ORGANISM: Homo sapien

<400> SEQUENCE: 251

```
tggtactcca ccatyatggg gtcaaccgcc atcctcgccc tcctcctggc tgttctccaa      60
ggagtctgtg ccgaggtgca gctgrtgcag tctggagcag aggtgaaaaa gtccggggag     120
tctctgaaga tctcctgtaa gggttctgga tacacctta agatctactg gatcgcctgg      180
gtgcgccagt tgcccgggaa aggcctggag tggatggggc tcatctttcc tgatgactct     240
gataccagat acagcccgtc cttccaaggc caggtcacca tctcagtcga taagtccatc     300
agcaccgcct atctgcagtg gagtaccaa                                       329
```

<210> SEQ ID NO 252
<211> LENGTH: 536
<212> TYPE: DNA
<213> ORGANISM: Homo sapien

<400> SEQUENCE: 252

```
tggtactcca ctcagcccaa ccttaattaa gaattaagag ggaacctatt actattctcc      60
caggctcctc tgctctaacc aggcttctgg gacagtatta gaaaaggatg tctcaacaag     120
tatgtagatc ctgtactggc ctaagaagtt aaactgagaa tagcataaat cagaccaaac     180
ttaatggtcg ttgagacttg tgtcctggag cagctgggat aggaaaactt ttgggcagca     240
agaggaagaa ctgcctggaa gggggcatca tgttaaaaat tacaagggga acccacacca     300
ggcccccttc ccagctctca gcctagagta ttagcatttc tcagctagag actcacaact     360
tccttgctta gaatgtgcca ccggggggag tccctgtggg tgatgaggct ctcaagagtg     420
agagtggcat cctatcttct gtgtgcccac aggagcctgg cccgagactt agcaggtgaa     480
gtttctggtc caggctttgc ccttgactca ctatgtgacc tctggtggag taccaa         536
```

<210> SEQ ID NO 253
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 253

```
ntgttgcgat cccagtaact cgggaagctg aggcgggagg atcacctgag ctcaggaggt      60
tgaggccgca gtgagccggg accacgccac tacactccag cctgggcat agagtgagac      120 cctccaagac agaaaagaaa agaaaggaag ggaaagggaa agggaaaagg aaaaggaaaa      180
ggaaaaggaa aaggaaaaga caagacaaaa caagacttga atttggatct cctgacttca     240
attttatgtt ctttctacac cacaattcct ctgcttacta agatgataat ttagaaaccc     300
ctcgttccat tctttacagc aagctggaag tttggtcaag taattacaat aatagtaaca     360
aatttgaata ttatatgcca ggtgttttc attcctgctc tcacttaatt ctcaccactc      420
tgatataaat acaattgctg ccgggtgtgg tggctcatgc ctgtaatccc ggcactttgg     480
gagaccgagg tgggcggats gcaacaa                                         507

<210> SEQ ID NO 254
<211> LENGTH: 222
<212> TYPE: DNA
<213> ORGANISM: Homo sapien
<220> FEATURE:
<221> NAME/KEY: misc_feature
<222> LOCATION: (1)...(222)
<223> OTHER INFORMATION: n = A,T,C or G

<400> SEQUENCE: 254
ttggattggt cactgtgagg aagccaaatc ggatccgaga gtctttttct aaaggccagt     60
actggccaca ctttctcctg ccgccttcct caaagctgaa gacacacaga gcaaggcgct    120
tctgttttac tccccaatgg taactccaaa ccatagatgg ttagctncccc tgctcatctt    180 tccacatccc tgctattcag tatagtccgt ggaccaatcc aa                        222

<210> SEQ ID NO 255
<211> LENGTH: 463
<212> TYPE: DNA
<213> ORGANISM: Homo sapien

<400> SEQUENCE: 255
tgttgcgatc cataaatgct gaaatggaaa taaacaacat gatgagggag gattaagttg     60
gggagggagc acattaaggt ggccatgaag tttgttggaa gaagtgactt tgaacaagg     120 ccttggtgtt aagagctgat gagagtgtcc cagacagagg ggccactggt acaatagacg    180
agatgggaga gggcttggaa ggtgtgcgaa ataggaagga gtttgttctg gtatgagtct    240
agtgaacaca gaggcgagag gccctggtgg gtgcagctgg agagttatgc agaataacat    300
taggccctgt gggggactgt agactgtcag caataatcca cagtttggat tttattctaa    360
gagtgatggg aagccgtgga aagggggtta agcaaggagt gaaattatca gatttacagt    420
gataaaaata aattggtctg gctactgggg aaaaaaaaaa aaa                      463

<210> SEQ ID NO 256
<211> LENGTH: 262
<212> TYPE: DNA
<213> ORGANISM: Homo sapien

<400> SEQUENCE: 256
ttggattggt caacctgctc aactctacyt ttcctccttc ttcctaaaaa attaatgaat     60
ccaatacatt aatgccaaaa cccttgggtt ttatcaatat ttctgttaaa aagtattatc    120
cagaactgga cataatacta cataataata cataacaacc ccttcatctg gatgcaaaca    180
tctattaata tagcttaaga tcactttcac tttacagaag caacatcctg ttgatgttat    240
tttgatgttt ggaccaatcc aa                                              262
```

<210> SEQ ID NO 257
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 257

```
gnggnnnnnn nnncaattcg actcngttcc cntggtancc ggtcgacatg gccgcgggat      60
taccgcttgt nnctgggggt gtatggggga ctatgaccgc ttgtagctgg gggtgtatgg     120
gggactatga ccgcttgtag mtggkggtgt atggggact atgaccgctt gtcggtggt      180
cggataaacc gacgcaaggg acgtgatcga agctgcgttc ccgctctttc gcatcggtag    240
ggatcatgga cagcaatatc cgcattcgyc tgaaggcgtt cgaccatcgc gtgctcgatc    300
aggcgaccgg cgacatcgcc gacaccgcac gccgtaccgg cgcgctcatc cgcggtccga    360
tcccgcttcc cacgcgcatc gagaagttca cggtcaaccg tggcccgcac gtcgacaaga    420
agtcgcgcga gcagttcgag gtgcgtacct acaagcggtc a                        461
```

<210> SEQ ID NO 258
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 258

```
tgaccgcttg tagctggggg tgtatggggg actacgaccg cttgtagctg gggtgtatg      60
ggggactatg accgcttgta gctggggtg tatgggggac tatgaccgct tgtagctggg     120
ggtgtatggg ggactaggac cgcttgtagc tgggggtgta tggggactta tgaccgcttg    180
tagctggggg tgtatggggg actacgaccg cttgtagctg gggtgtatg ggggactatg     240
accgcttgta nctggggtg tatgggggac tatgaccgct tgtgctgcct gggggatggg     300
aggagagttg tggttgggga aaaaaaaaaa aa                                  332
```

<210> SEQ ID NO 259
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 259

```
taccgcttgt gaccgcttgt gaccgcttgt gaccgcttgt gaccgcttgt gaccgcttgt      60
gaccgcttgt gaccgcttgt gaccgcttgt gaccgcttgt gaccgcttgt gaccgcttgt    120
gaccgcttgt gaccgcttgt nacnggggt gtctggggga ctatgannga ntgtnactgg     180
gggtgtctgg gggnctatga nngantgtna cnggggtgt ctgggggact atgannact     240
gtgcnncctg gggatcnga ggagantngn ggntagngat ggttngggan a              291
```

<210> SEQ ID NO 260
<211> LENGTH: 238
<212> TYPE: DNA

<213> ORGANISM: Homo sapien

<400> SEQUENCE: 260

| taagagggta ctggttaaaa tacaggaaat ctggggtaat gaggcagaga accaggatac | 60 |
| tttgaggtca gggatgaaaa ctagaatttt tttctttttt tttgcctgag aaacttgctg | 120 |
| ctctgaagag gcccatgtat taattgcttt gatcttcctt ttcttacagc cctttcaagg | 180 |
| gcagagccct ccttatcctg aaggaatctt atccttagct atagtatgta ccctctta | 238 |

<210> SEQ ID NO 261
<211> LENGTH: 746
<212> TYPE: DNA
<213> ORGANISM: Homo sapien
<220> FEATURE:
<221> NAME/KEY: misc_feature
<222> LOCATION: (1)...(746)
<223> OTHER INFORMATION: n = A,T,C or G

<400> SEQUENCE: 261

| ttgggcacct tcaatatcaa tagctaacat ttattgagtg tttatcgtat cataaaacac | 60 |
| tgttctaagc ctttaaacgt actaattcat ttaatgctca taatcacttt agaaggtggg | 120 |
| tactagtatt agtctcattt acagatgcaa catgcaggca cagagaggtt aattaacttg | 180 |
| cccaaggtaa cacagctaag aaatagaaaa atatattgaat ctggaaagtt gggcttctgg | 240 |
| gtaacccaca gagtcttcaa tgagcctggg gcctcactca gtttgctttt acaaagcgaa | 300 |
| tgagtaacat cacttaattc agtgagtagg ccaaatggag gtcagctacg agtttctgct | 360 |
| gttcttgcag tggactgaca gatgtttaca acgtctggcc atcagtwaat ggactgatta | 420 |
| tcattgggaw gtgggtgggc tgaatgttgg ccagtgaagt ttattcawgc catattttta | 480 |
| tgtttaggat gacttttggc tggtcctagg gcaagctctg tctgscacgg aacacagaat | 540 |
| wacacaggga cccccctcaat ttctggtgtg gctagaacca tgaaccactg gttgggggaa | 600 |
| caagcggtca aaacctaagt gcggccggct ggcagggtcc acccatatgg ggaaaactcc | 660 |
| cnacgcgttt ggaatgcctn agctngaatt attctaanag ttgtccncnt aaaattagcc | 720 |
| tgggcgttaa tcangggtcn naagcc | 746 |

<210> SEQ ID NO 262
<211> LENGTH: 588
<212> TYPE: DNA
<213> ORGANISM: Homo sapien
<220> FEATURE:
<221> NAME/KEY: misc_feature
<222> LOCATION: (1)...(588)
<223> OTHER INFORMATION: n = A,T,C or G

<400> SEQUENCE: 262

| tgaccgcttg tcatctcaca tggggtcctg cacgcttttg cctttgtagg aaacctgaca | 60 |
| tttgtctgtt tcttctttct cttttccttc ccatatcctc ctaatttacg tttgacttgt | 120 |
| ttgctgagga ggcaggagct agagactgct gtgagctcat aggggtggga agtttatcct | 180 |
| tcaagtcccg cccactcatc actgcttctc accttcccct gaccaggctt acaagtgggt | 240 |
| tcttgcctgc tttcccttttg gacccaacaa gcccctgtaa tgagtgtgca tgactctgac | 300 |
| agctgtggac tcagggtcct tggctacagc tgccatgtaa aatatctcat ccagttctcg | 360 |
| caaattgtta aaataaccac atttcttaga ttccagtacc caaatcatgt ctttacgaac | 420 |
| tgctcctcac acccagaagt ggcacaataa ttcttgggga attattactt ttttttttct | 480 |
| ctctnttnnc gnnngnnnng gnnngnccag gaattaccac nttggaagac ctggccngaa | 540 | tttattatan aggggagccg attnttttc ctaacacaaa gcgggtca   588

<210> SEQ ID NO 263
<211> LENGTH: 730
<212> TYPE: DNA
<213> ORGANISM: Homo sapien
<220> FEATURE:
<221> NAME/KEY: misc_feature
<222> LOCATION: (1)...(730)
<223> OTHER INFORMATION: n = A,T,C or G

<400> SEQUENCE: 263

| | | | | | |
|---|---|---|---|---|---|
| tttttttttt | tttggcctga | gcaactgaaa | ttatgaaatt | tccatatact | caaaagagta | 60 |
| agactgcaaa | aagattaaat | gtaaaagttg | tcttgtatac | agtaatgttt | aagataccta | 120 |
| ttanatttat | aaatggaaaa | ttagggcatt | tggatataca | agttgaaaat | tcaggagtga | 180 |
| ggttgggctg | gctgggtata | tactgaaaac | tgtcagtaca | cagatgacat | ctaaaaccac | 240 |
| aaatctggtt | ttattttagc | agtgatatgt | gtcactccca | caaaagcctt | cccaattggc | 300 |
| ctcagcatac | acaacaagtc | acctccccac | agccctctac | acataaacaa | attccttagt | 360 |
| ttagttcagg | aggaaatgcg | ccctttttcct | tccgctctag | gtgaccgcaa | ggcccagttc | 420 |
| tcgtcaccaa | gatgttaagg | gaagtctgcc | aaagaggcat | ctgaaaggaa | ataaggggaa | 480 |
| tgggagtgac | cacaaaggaa | agccaaggan | aaactttgga | gaccgtttct | aganccctgg | 540 |
| catttcacaa | caaaactcng | gaacaaacct | tgtctcatca | atcatttaag | cccttcgttt | 600 |
| ggannagact | ttctgaactg | ggcgctgaac | ataaaacctca | ttgaatgtct | tcacagtctc | 660 |
| ccagctgaag | gcacaccttg | ggccagaagg | ggaatcttcc | aggtcctcaa | nacagggctc | 720 |
| gcccttttgnc | | | | | | 730 |

<210> SEQ ID NO 264
<211> LENGTH: 715
<212> TYPE: DNA
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 264

| | | | | | |
|---|---|---|---|---|---|
| tttttttttt | tttggccagt | atgatagtct | ctaccactat | attgaagctc | ttaggtcatt | 60 |
| tacacttaat | gtggttatag | atgctgttga | gcttacttct | accaccttgc | tatttctccc | 120 |
| gtctcttttt | tgttcctttt | ctcttctttt | cctcccttat | tttataattg | aattttttag | 180 |
| gattctattt | tatatagatt | tatcagctat | aacactttgt | attcttttgt | tttgtggttc | 240 |
| ttctgtcatt | tcaatgtgca | tcttaaactc | atcacaatct | attttcaaat | aatatcatat | 300 |
| aaccttacat | ataatgtaag | aatctaccac | catatatttc | catttctccc | ttccatccta | 360 |
| tgtntgtcat | attttttcct | ttatatatgt | tttaaagaca | taatagtata | tgggaggttt | 420 |
| ttgcttaaaa | tgtgatcaat | attccttcaa | ngaaacgtaa | aaattcaaaa | taatntctg | 480 |
| tttattctca | aatnnaccta | atatttccta | ccatntctna | tacntttcaa | gaatctgaag | 540 |
| gcattggttt | tttccggctt | aagaacctcc | tctaaagcac | tctaagcaga | attagtctct | 600 |
| ctgggagagg | aattctccca | agcttgggcc | ttnanntgta | ctccntnang | gttaaanttt | 660 |
| ggccgggaaa | tagaaattcc | aagttaacag | gntantttt | nttttttnttn | tcncc | 715 |

<210> SEQ ID NO 265

```
<211> LENGTH: 152
<212> TYPE: DNA
<213> ORGANISM: Homo sapien

<400> SEQUENCE: 265
tttttttttt tttcccaaca caaagcacca ttatctttcc tcacaatttt caacatagtt      60
tgattcccat gaagaggtta tgatttctaa agaaaacatg gctactatac tatcaatcag     120
ggttaaatct tttttttttg agacggagtt ta                                   152

<210> SEQ ID NO 266
<211> LENGTH: 193
<212> TYPE: DNA
<213> ORGANISM: Homo sapien
<220> FEATURE:
<221> NAME/KEY: misc_feature
<222> LOCATION: (1)...(193)
<223> OTHER INFORMATION: n = A,T,C or G

<400> SEQUENCE: 266
taaactccgt cccttcttta atcaatatgg aggctaccca ctccacatta ccttcttttc      60
aagggactgt ttccgtaact gttgtgggta ttcacgacca ggcttctaaa cctcttaaaa     120
ctccccaatt ctggtgccaa cttggacaac atgctttttt tttttttttt tttttttttn     180
gagacggagt tta                                                        193

<210> SEQ ID NO 267
<211> LENGTH: 460
<212> TYPE: DNA
<213> ORGANISM: Homo sapien

<400> SEQUENCE: 267
tgttgcgatc ccttaagcat gggtgctatt aaaaaaatgg tggagaagaa aatacctgga      60
atttacgtct tatctttaga gattgggaag accctgatgg aggacgtgga gaacagcttc     120
ttcttgaatg tcaattccca agtaacaaca gtgtgtcagg cacttgctaa ggatcctaaa     180
ttgcagcaag gctacaatgc tatgggattc tcccagggag gccaatttct gagggcagtg     240
gctcagagat gcccttcacc tcccatgatc aatctgatct cggttggggg acaacatcaa     300 ggtgttttg gactccctcg atgcccagga gagagctctc acatctgtga cttcatccga     360
aaaacactga atgctgggc gtactccaaa gttgttcagg aacgcctcgt gcaagccgaa     420
tactggcatg acccataaaa ggaggatgtg gatcgcaaca                           460

<210> SEQ ID NO 268
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 268
tgttgcgatc cgttgataga atagcgacgt ggtaatgagt gcatggcacg cctccgactt      60
accttcgccc gtggggaccc cgagtacgtc tacggcgtcg tcacttagag taccctctgg     120
acgcccgggc gcgttcgatt taccggaagc gcgagctgca gtgggcttgc gccccggcc      180 aaattctttg gggggtttaa ggccgcgggg aatttgaggt atctctatca gtatgtagcc     240
aagttggaac agtcgccatt cccgaaatcg ctttctttga atccgcaccg cctccagcat     300
tgcctcattc atcaacctga aggcacgcat aagtgacggt tgtgtcttca gcagctccac     360
```

```
tccataacta gcgcgctcga cctcgtcttc gtacgcgcca ggtccgtgcg tgcgaattcc      420
caactccggt gagttgcgca tttcaagttn cgaaactgtt cgcctccacn atttggcatg      480
ttcacgcatg acacggaata aactcgtcca gtaccgggaa tgggatcgca aca             533
```

<210> SEQ ID NO 269
<211> LENGTH: 50
<212> TYPE: DNA
<213> ORGANISM: Homo sapien

<400> SEQUENCE: 269

```
tttttttttt ttcgcctgaa ttagctacag atcctcctca caagcggtca                 50
```

<210> SEQ ID NO 270
<211> LENGTH: 519
<212> TYPE: DNA
<213> ORGANISM: Homo sapien

<400> SEQUENCE: 270

```
tgttgcgatc caaataaccc accagcttct tgcacacttc gcagaagcca ccgtcctttg      60
gctgagtcac gtgaacggtc agtgcaagca gccgcgtgcc agagcagagg tgcagcatgc     120
tgcacaccag ctcagggctg acctcctcca gcaggatgga caggatggag ctgccgtacg     180
tgtccaccac ctcctggcac tcttccgaca gggacttcgg cagcttcgag cacattttgt    240
caaaagcgtc gagtatttct ttctcagtct tgttgttgtc aatcagcttg gtcacctcct    300
tcaccaggaa ttcacacacc tcacagtaaa catcagactt tgctgggacc tcgtgcttct    360
taatgggctc caccagttcc agggcaggga tgacattctt ggaggccact ttggcgggga    420
ccagagtctg catgggcatc tctttcacct catcacagaa cccaaccagc gcacagatct    480
ccttgggttg catgtgcatc atcatctggg atcgcaaca                            519
```

<210> SEQ ID NO 271
<211> LENGTH: 457
<212> TYPE: DNA
<213> ORGANISM: Homo sapien

<400> SEQUENCE: 271

```
tttttttttt ttcgggcggc gaccggacgt gcactcctcc agtagcggct gcacgtcgtg      60
ccaatggccc gctatgagga ggtgagcgtg tccggcttcg aggagttcca ccgggccgtg     120
gaacagcaca atggcaagac cattttcgcc tactttacgg gttctaagga cgccgggggg    180
aaaagctggt gccccgactg cgtgcaggct gaaccagtcg tacgagaggg gctgaagcac    240
attagtgaag gatgtgtgtt catctactgc caagtaggag aagagcctta ttggaaagat    300
ccaaataatg acttcagaaa aaacttgaaa gtaacagcag tgcctacact acttaagtat    360
ggaacacctc aaaaactggt agaatctgag tgtcttcagg ccaacctggt ggaaatgttg    420
ttctctgaag attaagattt taggatggca atcaaga                              457
```

<210> SEQ ID NO 272
<211> LENGTH: 102
<212> TYPE: DNA
<213> ORGANISM: Homo sapien

<400> SEQUENCE: 272

```
tttttttttt ttgggcaaca acctgaatac cttttcaagg ctctggcttg ggctcaagcc      60
cgcaggggaa atgcaactgg ccaggtcaca gggcaatcaa ga                        102
```

<210> SEQ ID NO 273
<211> LENGTH: 455
<212> TYPE: DNA
<213> ORGANISM: Homo sapien
<220> FEATURE:
<221> NAME/KEY: misc_feature
<222> LOCATION: (1)...(455)
<223> OTHER INFORMATION: n = A,T,C or G

<400> SEQUENCE: 273

```
tttttttttt ttggcaatca acaggtttaa gtcttcggcc gaagttaatc tcgtgttttt      60
ggcaatcaac aggtttaagt cttcggccga agtaatctc gtgtttttgg caatcaacag     120
gtttaagtct tcgccgaag ttaatctcgt gtttttggca atcaacaggt ttaagtcttc     180
ggccgaagtt aatctcgtgt ttttggcaat caacaggttt aagtcttcgg ccgaagttaa     240
tctcgtgttt ttggcaatca acaggtttaa gtcttcggcc gaagttaatc tcgtgttttt     300
ggcaatcaag aggtttaagt cttcggccga agttaatctc gtgtttttgg caatcaacag     360
gtttaagtct tcggccgaan ttaatctcgt gtttttggca atcaacaggt ttaantcttc     420
ggccgaagtt aatctcgtgt ttttggcaat caana                                455
```

<210> SEQ ID NO 274
<211> LENGTH: 461
<212> TYPE: DNA
<213> ORGANISM: Homo sapien

<400> SEQUENCE: 274

```
tttttttttt ttggccaata cccttgatga acatcaatgt gaaatcctc ggtaaaatac      60
tggcaaacca aatccagcag cacatcaaaa agcttatcca ccatgatcaa gtgggcttca     120
tccctgggat gcaaggctgg ttcaacataa gaaaatcaat aaatgtaatc catcacataa     180
acagaaccaa agacaaaaac cacatgatta tctcaataga tgcagaaaag gccttggaca     240
aattcaacag cccttcatgc taaacactct aataaactag atattgatgg aatgtatct     300
caaaataata gagctatttt atgacaaacc cacagccaat atcatactga atgggcaaag     360
actggaagca ttccctttga aaactggcac aagacaagga tgccctctct caccgctcct     420
attcaacata gtattggaag ttctggccag ggcaatcaag a                        461
```

<210> SEQ ID NO 275
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 275

```
tttttttttt ttggccaaca ccaagtcttc cacgtgggag gttttattat gttttacaac      60
catgaaaaca taggaaggtg gctgttacag caaacatttc agatagacga atcggccaag     120
ctccccaaac cccaccttca cagcctcttc cacacgtctc ccanagattg ttgtccttca     180
cttgcaaatt canggatgtt ggaagtngac atttnnagtn gcnggaaccc catcagtgaa     240
ncantaagca gaantacgat gactttgana nacanctgat gaagaacacn ctacnganaa     300
ccctttctnt cgtgttanga tctcnngtcc ntcactaatg cggccccctg cnggtccacc     360
atttgggaga actcccccn cgttggatcc ccccttgagt ntcccattct ngtccccan      420
accngncttg ngngncantn cnncctcnca ccntgtttcc ctgnngtnaa aatnngtttt     480
```

```
nccgccnccc naattcccac ccnaatcaca gcgaanccng aaggccttcn naagtgttta    540
angcccngng gtttcctcnt ntanttgcag cctaccctcc cncttnnnnt tncgngttgg    600
tcgcgccctg gncncgcctn gttcctctt nnggnnacaa cctngntcnn nggcncntcn    660
nnnctnttcc tnnnactagc tngcctntcc ncnccgnggn ncanngcaca ttncncnnac    720 tntgtnncc                                                           729
```

<210> SEQ ID NO 276
<211> LENGTH: 339
<212> TYPE: DNA
<213> ORGANISM: Homo sapien

<400> SEQUENCE: 276

```
tgacctgaca tgtagtagat acttaataaa tatttgtgga atgaatggat gaagtggagt     60
tacagagaaa aatagaaaag tacaaattgt tgtcagtgtt ttgaaggaaa attatgatct    120
ttcccaaagt tctgacttca ttctaagaca gggttagtat ctccatacat aattttactt    180
gcttttgaaa atcaaatgag ataatctatt tagattgata atttatttag actggctata    240
aactattaag tgctagcaaa tatacatttt aatctcattt tccacctctt gtgatatagc    300
tatgtaggtg ttgactttaa tggatgtcag gtcaatccc                          339
```

<210> SEQ ID NO 277
<211> LENGTH: 664
<212> TYPE: DNA
<213> ORGANISM: Homo sapien
<220> FEATURE:
<221> NAME/KEY: misc_feature
<222> LOCATION: (1)...(664)
<223> OTHER INFORMATION: n = A,T,C or G

<400> SEQUENCE: 277

```
tgacctgaca tccataacaa aatctttctc cattatattc ttctagggga atttcttgaa     60
aagcatccaa aggaaacaaa tgatggtaag accgtgccaa gtggggagca gacaccaaag    120
taagaccaca gattttacat tcaacaggta gctcacagta ctttgcccga cactgtgggc    180
agaaatagcc tcctaatgta agccctggct cagtattgcc atccaaatgc gccatgctga    240
aagagggttt tgcatcctgg tcagatnaag aagcaatggt gtgctgagga aatcccatac    300
gaataagtga gcattcagaa cttgagctag caggaggagg actaagatga tgtgtgagca    360
actctttgta atggctttca tctaaaataa catggtacgt gccaccagtt tcacgagcaa    420
gtacagtgca aacgcgaact tctgcagaca atccaataac agatactcta attttagctg    480
cctttagggt cttgattaaa tcataaatat tagatggatc gcaagttgta aggntgctaa    540
aagatgatta gtacttctcg acttgtatgt ccaggcatgt tgttttaaan tctgccttag    600
nccctgctta ggggaattt taaagaagat ggctctccat gttcanggtc aatcacnaat    660
tgcc                                                                664
```

<210> SEQ ID NO 278
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 278

```
tgacctgaca ttgaggaaga gcacacacct ctgaaattcc ttaggttcag aagggcattt        60
gacacagagt gggcctctga taattcatga aatgcattct gaagtcatcc agaatggagg       120
ctgcaatctg ctgtgctttg ggggttgcct cactgtgctc ctggatatca cacaaaagct       180
gcaatccttc ttcttcaact aacattttgc agtatttgct gggatttttta ctgcagacat      240 gatacatagc ccatagtgcc cagagctgaa cctctggttg agagaagttg ccaaggagcg       300
ggaaaaatgt cttgaaagat ctataggtca ccaatgctgt catcttacaa cttgaacttg       360
gccaattctg tatggttgca tgcagatctt ggagaagagt acgcctctgg aagtcacggg       420
atatccaaan ctgtctgtca gatgtcaggt ca                                     452
```

```
<210> SEQ ID NO 279
<211> LENGTH: 274
<212> TYPE: DNA
<213> ORGANISM: Homo sapien

<400> SEQUENCE: 279
tttttttttt ttcggcaagg caaatttact tctgcaaaag ggtgctgctt gcacttttgg       60
ccactgcgag agcacaccaa acaaagtagg gaagggtttt ttatccctaa cgcggttatt      120
ccctggttct gtgtcgtgtc cccattggct ggagtcagac tgcacaatct acactgaccc     180
aactggctac tgtttaaaat tgaatatgaa aattaggta ggaagggga ggctgtttgt       240 tacggtacaa gacgtgtttg ggcatgtcag gtca                                  274
```

```
<210> SEQ ID NO 280
<211> LENGTH: 272
<212> TYPE: DNA
<213> ORGANISM: Homo sapien

<400> SEQUENCE: 280
tacctgacat ggagaaataa cttgtagtat tttgcgtgca atggaatact atatgagggt       60
gaaaatgaat gaactagcaa tgcgtgtatc aacatgaata aatccccaaa acataataat     120
gttgaatgga aaggtgagt ttcagaagga tatatatgcc ctctaaatcc atttatgtaa       180 accttttaaaa aactacatta tttatggtca taagtccatc cagaaaatat ttaaaaacct    240
acatgggatt gataactact gatgtcaggt ca                                    272
```

```
<210> SEQ ID NO 281
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 281
tttttttttt ttggccaata gcatgattta aacattggaa aaagtcaaat gagcaatgcg       60
aatttttatg ttctcttgaa taatcaaaag agtaggcaac attggttcct cattcttgaa     120
tagcattaat cagaaaatat tgcatagcct ctagcctcct tagagtaggt gtgctctctc     180
aaatatatca tagtcccaca gtttatttca tgtatatttt ctgcctgaat cacatagaca     240
tttgaatttg caacgcctga tgtaaatata taaattctta ccaatcagaa acatagcaag    300
aaattcaggg acttggtcat yatcaggta tgacagcana tccctgtara aacactgata      360
cacactcaca cacgtatgca acgtggagat gtcgcyttww kkktwywcwm rmrycrwcgn    420
aatcacttan n                                                           431
```

<210> SEQ ID NO 282
<211> LENGTH: 98
<212> TYPE: DNA
<213> ORGANISM: Homo sapien

<400> SEQUENCE: 282
attcgattcg atgcttgagc ccaggagttc aagactgcag tgagccactg cacttcaggc    60
tggacaacag agcgagtccc tgtgccaaaa aaaaaaaa                            98

<210> SEQ ID NO 283
<211> LENGTH: 764
<212> TYPE: DNA
<213> ORGANISM: Homo sapien
<220> FEATURE:
<221> NAME/KEY: misc_feature
<222> LOCATION: (1)...(764)
<223> OTHER INFORMATION: n = A,T,C or G

<400> SEQUENCE: 283
tttttttttt ttcgcaagca cgtgcacttt attgaatgac actgtagaca ggtgtgtggg    60
tataaactgc tgtatctagg ggcaggacca aggggcagg ggcaacagcc ccagcgtgca    120
gggccascat tgcacagtgg astgcaaagg ttgcaggcta tgggcggcta ctavtaaccc    180 cgttttcct gtattatctg taacataata tggtagactg tcacagagcc gaatwccart    240
hacasgatga atccaawggt caygaggatg cccasaatca gggcccasat sttcaggcac    300
ttggcggtgg gggcatasgc ctgkgccccg gtcacgtcsc caaccwtcty cctgtccta    360 cmcttgawtc cncnccttnn nntnccntna tntgcccgcc cncctcctng ngtcaaccng    420
natctgcact anctccctcn ccccttntgg antctcntcc ttcaantaan nttatccttn    480 acnccccct cnccttttccc ctnccncccn tnatcccngn nccnctatca ntcntncct    540 cnctntnctn cnnatcgttc cncctnntaa ctacncttn nacnanncct cactnatncc    600
ngnnanttct ttccttccct cccnacgcnn tgcgtgcgcc cgtctngcct nnnctncgna    660 cccnnactt atttacctt ncaccctagc nctctacttn acccanccnc tcctacctcc    720
nggnccaccc nncccntatc nctnnctctn tcnnctcntt cccc                    764

<210> SEQ ID NO 284
<211> LENGTH: 157
<212> TYPE: DNA
<213> ORGANISM: Homo sapien

<400> SEQUENCE: 284
caagtgtagg cacagtgatg aaagcctgga gcaaacacaa tctgtgggta attaacgttt    60
atttctcccc ttccaggaac gtcttgcatg gatgatcaaa gatcagctcc tggtcaacat    120
aaataagcta gtttaagata cgttccccta cacttga                            157

<210> SEQ ID NO 285
<211> LENGTH: 150
<212> TYPE: DNA
<213> ORGANISM: Homo sapien

<400> SEQUENCE: 285
attcgattgt actcagacaa caatatgcta agtggaagaa gtcagtcaca aaagaccaca    60
tactgtatga cttcatttac attaagtgtc cagaataggc aaatccgtag agacagaaag    120
tagatgagca gctgcctagg tctgagtaca                                    150

<210> SEQ ID NO 286
<211> LENGTH: 219
<212> TYPE: DNA
<213> ORGANISM: Homo sapien

<400> SEQUENCE: 286

```
attcgatttt ttttttttg gccatgatga aattcttact ccctcagatt ttttgtctgg      60
ataaatgcaa gtctcaccac cagatgtgaa attacagtaa actttgaagg aatctcctga    120
gcaaccttgg ttaggatcaa tccaatattc accatctggg aagtcaggat ggctgagttg    180
caggtcttta caagttcggg ctggattggt ctgagtaca                           219
```

<210> SEQ ID NO 287
<211> LENGTH: 196
<212> TYPE: DNA
<213> ORGANISM: Homo sapien

<400> SEQUENCE: 287

```
attcgattct tgaggctacc aggagctagg agaagaggca tggaacaaat tttccctcat     60
atccatactc agaaggaacc aaccctgctg acaccttaat ttcagcttct ggcctctaga   120
actgtgagag agtacatttc tcttggttta agccaagaga atctgtcttt tggtacttta   180
tatcatagcc tcaaga                                                    196
```

<210> SEQ ID NO 288
<211> LENGTH: 199
<212> TYPE: DNA
<213> ORGANISM: Homo sapien

<400> SEQUENCE: 288

```
attcgatttc agtccagtcc cagaacccac attgtcaatt actactctgt araagattca     60
tttgttgaaa ttcattgagt aaaacattta tgatcccctta atatatgcca attaccatgc   120
taggtactga agattcaagt gaccgagatg ctagcccttg ggttcaagtg atccctctcc   180
cagagtgcac tggactgaa                                                 199
```

<210> SEQ ID NO 289
<211> LENGTH: 182
<212> TYPE: DNA
<213> ORGANISM: Homo sapien

<400> SEQUENCE: 289

```
attcgattct tgaggctaca aacctgtaca gtatgttact ctactgaata ctgtaggcaa     60
tagtaataca gaagcaagta tctgtatatg taaacattaa aaaggtacag tgaaacttca   120
gtattataat cttagggacc accattatat atgtggtcca tcattggcca aaaaaaaaaa   180
aa                                                                   182
```

<210> SEQ ID NO 290
<211> LENGTH: 1646
<212> TYPE: DNA
<213> ORGANISM: Homo sapien

<400> SEQUENCE: 290

```
ggcacgagga gaaatgtaat tccatatttt atttgaaact tattccatat tttaattgga     60
tattgagtga ttgggttatc aaacacccac aaacttttaat tttgttaaat ttatatggct   120
ttgaaataga agtataagtt gctaccattt tttgataaca ttgaaagata gtattttacc   180
atctttaatc atcttggaaa atacaagtcc tgtgaacaac cactctttca cctagcagca   240
```

```
tgaggccaaa agtaaaggct ttaaattata acatatggga ttcttagtag tatgtttttt      300
tcttgaaact cagtggctct atctaacctt actatctcct cactctttct ctaagactaa      360
actctaggct cttaaaaatc tgcccacacc aatcttagaa gctctgaaaa gaatttgtct      420
ttaaatatct tttaatagta acatgtattt tatggaccaa attgacattt tcgactattt      480
tttccaaaaa agtcaggtga atttcagcac actgagttgg gaatttctta tcccagaaga      540
ccaaccaatt tcatatttat ttaagattga ttccatactc cgttttcaag gagaatccct      600
gcagtctcct taaaggtaga acaaatactt tctattttt tttcaccatt gtgggattgg       660
actttaagag gtgactctaa aaaaacagag aacaaatatg tctcagttgt attaagcacg      720
gacccatatt atcatattca cttaaaaaaa tgatttcctg tgcacctttt ggcaacttct      780
cttttcaatg tagggaaaaa cttagtcacc ctgaaaaccc acaaaataaa taaaacttgt      840
agatgtgggc agaaggtttg ggggtggaca ttgtatgtgt ttaaattaaa ccctgtatca      900
ctgagaagct gttgtatggg tcagagaaaa tgaatgctta gaagctgttc acatcttcaa      960
gagcagaagc aaaccacatg tctcagctat attattattt attttttatg cataaagtga     1020
atcatttctt ctgtattaat ttccaagggg ttttaccctc tatttaaatg ctttgaaaaa     1080
cagtgcatta acaatgggtt gatatttttc tttaaaagaa aaatataatt atgaaagcca     1140
agataatctg aagcctgttt tattttaaaa cttttttatgt tctgtggttg atgttgtttg     1200
tttgtttgtt tctattttgt tggttttta ctttgttttt tgttttgttt tgttttgttt      1260
kgcatactac atgcagttct ttaaccaatg tctgtttggc taatgtaatt aaagttgtta     1320
atttatatga gtgcatttca actatgtcaa tggtttctta atatttattg tgtagaagta     1380
ctggtaattt ttttatttac aatatgttta aagagataac agtttgatat gttttcatgt     1440
gtttatagca gaagttattt atttctatgg cattccagcg gatattttgg tgtttgcgag     1500
gcatgcagtc aatattttgt acagttagtg gacagtattc agcaacgcct gatagcttct     1560
ttggccttat gttaaataaa aagacctgtt tgggatgtat ttttttatttt taaaaaaaaa    1620 aaaaaaaaaa aaaaaaaaaa aaaaaa                                          1646
```

<210> SEQ ID NO 291
<211> LENGTH: 1851
<212> TYPE: DNA
<213> ORGANISM: Homo sapien

<400> SEQUENCE: 291

```
tcatcaccat tgccagcagc ggcaccgtta gtcaggtttt ctgggaatcc cacatgagta       60
cttccgtgtt cttcattctt cttcaatagc cataaatctt ctagctctgg ctggctgttt      120
tcacttcctt taagcctttg tgactcttcc tctgatgtca gctttaagtc ttgttctgga      180
ttgctgtttt cagaagagat ttttaacatc tgttttttctt tgtagtcaga aagtaactgg      240
caaattacat gatgatgact agaaacagca tactctctgg ccgtctttcc agatcttgag      300
aagatacatc aacattttgc tcaagtagag ggctgactat acttgctgat ccacaacata      360
cagcaagtat gagagcagtt cttccatatc tatccagcgc atttaaattc gcttttttct      420
tgattaaaaa tttcaccact tgctgttttt gctcatgtat accaagtagc agtggtgtga      480
ggccatgctt gttttttgat tcgatatcag caccgtataa gagcagtgct ttggccatta      540
atttatcttc attgtagaca gcatagtgta gagtggtatt tccatactca tctgaatat       600 ttggatcagt gccatgttcc agcaacatta acgcacattc atcttcctgg cattgtacgg      660
```

-continued

```
cctttgtcag agctgtcctc tttttgttgt caaggacatt aagttgacat cgtctgtcca    720
gcacgagttt tactacttct gaattcccat tggcagaggc cagatgtaga gcagtcctct    780
tttgcttgtc cctcttgttc acatccgtgt ccctgagcat gacgatgaga tcctttctgg    840
ggactttacc ccaccaggca gctctgtgga gcttgtccag atcttctcca tggacgtggt    900
acctgggatc catgaaggcg ctgtcatcgt agtctcccca agcgaccacg ttgctcttgc    960
cgctcccctg cagcagggga agcagtggca gcaccacttg cacctcttgc tcccaagcgt   1020
cttcacagag gagtcgttgt ggtctccaga agtgcccacg ttgctcttgc cgctcccccT   1080
gtccatccag ggaggaagaa atgcaggaaa tgaaagatgc atgcacgatg gtatactcct   1140
cagccatcaa acttctggac agcaggtcac ttccagcaag gtggagaaag ctgtccaccc   1200
acagaggatg agatccagaa accacaatat ccattcacaa acaaacactt ttcagccaga   1260
cacaggtact gaaatcatgt catctgcggc aacatggtgg aacctaccca atcacacatc   1320
aagagatgaa gacactgcag tatatctgca caacgtaata ctcttcatcc ataacaaaat   1380
aatataattt tcctctggag ccatatggat gaactatgaa ggaagaactc cccgaagaag   1440
ccagtcgcag agaagccaca ctgaagctct gtcctcagcc atcagcgcca cggacaggar   1500 tgtgttttctt ccccagtgat gcagcctcaa gttatcccga agctgccgca gcacacggtg   1560
gctcctgaga aacaccccag ctcttccggt ctaacacagg caagtcaata aatgtgataa   1620
tcacataaac agaattaaaa gcaaagtcac ataagcatct caacagacac agaaaaggca   1680
tttgacaaaa tccagcatcc ttgtatttat tgttgcagtt ctcagaggaa atgcttctaa   1740
cttttcccca tttagtatta tgttggctgt gggcttgtca taggtggttt ttattacttt   1800
aaggtatgtc ccttctatgc ctgttttgct gagggtttta attctcgtgc c             1851
```

<210> SEQ ID NO 292
<211> LENGTH: 1851
<212> TYPE: DNA
<213> ORGANISM: Homo sapien

<400> SEQUENCE: 292

```
tcatcaccat tgccagcagc ggcaccgtta gtcaggtttt ctgggaatcc cacatgagta     60
cttccgtgtt cttcattctt cttcaatagc cataaatctt ctagctctgg ctggctgttt    120
tcacttcctt taagcctttg tgactcttcc tctgatgtca gctttaagtc ttgttctgga    180
ttgctgtttt cagaagagat ttttaacatc tgttttttctt tgtagtcaga aagtaactgg    240
caaattacat gatgatgact agaaacagca tactctctgg ccgtctttcc agatcttgag    300
aagatacatc aacattttgc tcaagtagag ggctgactat acttgctgat ccacaacata    360
cagcaagtat gagagcagtt cttccatatc tatccagcgc atttaaattc gcttttttct    420
tgattaaaaa tttcaccact tgctgttttt gctcatgtat accaagtagc agtggtgtga    480
ggccatgctt gttttttgat tcgatatcag caccgtataa gagcagtgct ttggccatta    540
atttatcttc attgtagaca gcatagtgta gagtggtatt tccatactca tctggaatat    600
ttggatcagt gccatgttcc agcaacatta acgcacattc atcttcctgg cattgtacgg    660
cctttgtcag agctgtcctc tttttgttgt caaggacatt aagttgacat cgtctgtcca    720
gcacgagttt tactacttct gaattcccat tggcagaggc cagatgtaga gcagtcctct    780
tttgcttgtc cctcttgttc acatccgtgt ccctgagcat gacgatgaga tcctttctgg    840
ggactttacc ccaccaggca gctctgtgga gcttgtccag atcttctcca tggacgtggt    900
acctgggatc catgaaggcg ctgtcatcgt agtctcccca agcgaccacg ttgctcttgc    960
```

```
cgctcccctg cagcagggga agcagtggca gcaccacttg cacctcttgc tcccaagcgt    1020
cttcacagag gagtcgttgt ggtctccaga agtgcccacg ttgctcttgc cgctcccct     1080 gtccatccag ggaggaagaa atgcaggaaa tgaaagatgc atgcacgatg gtatactcct   1140
cagccatcaa acttctggac agcaggtcac ttccagcaag gtggagaaag ctgtccaccc   1200
acagaggatg agatccagaa accacaatat ccattcacaa acaaacactt ttcagccaga   1260
cacaggtact gaaatcatgt catctgcggc aacatggtgg aacctaccca atcacacatc   1320
aagagatgaa gacactgcag tatatctgca caacgtaata ctcttcatcc ataacaaaat   1380
aatataattt tcctctggag ccatatggat gaactatgaa ggaagaactc cccgaagaag   1440
ccagtcgcag agaagccaca ctgaagctct gtcctcagcc atcagcgcca cggacaggar   1500
tgtgtttctt ccccagtgat gcagcctcaa gttatcccga agctgccgca gcacacggtg   1560
gctcctgaga aacaccccag ctcttccggt ctaacacagg caagtcaata aatgtgataa   1620
tcacataaac agaattaaaa gcaaagtcac ataagcatct caacagacac agaaaaggca   1680
tttgacaaaa tccagcatcc ttgtatttat tgttgcagtt ctcagaggaa atgcttctaa   1740
cttttcccca tttagtatta tgttggctgt gggcttgtca taggtggttt ttattacttt   1800
aaggtatgtc ccttctatgc ctgttttgct gagggtttta attctcgtgc c             1851

<210> SEQ ID NO 293
<211> LENGTH: 668
<212> TYPE: DNA
<213> ORGANISM: Homo sapien

<400> SEQUENCE: 293
cttgagcttc caaataygga agactggccc ttacacasgt caatgttaaa atgaatgcat    60
ttcagtattt tgaagataaa attrgtagat ctataccttg ttttttgatt cgatatcagc   120
accrtataag agcagtgctt tggccattaa tttatctttc attrtagaca gcrtagtgya   180
gagtggtatt tccatactca tctggaatat ttggatcagt gccatgttcc agcaacatta   240
acgcacattc atcttcctgg cattgtacgg cctgtcagta ttagacccaa aaacaaatta   300
catatcttag gaattcaaaa taacattcca cagctttcac caactagtta tatttaaagg   360
agaaaactca tttttatgcc atgtattgaa atcaaaccca cctcatgctg atatagttgg   420
ctactgcata cctttatcag agctgtcctc tttttgttgt caaggacatt aagttgacat   480
cgtctgtcca gcaggagttt tactacttct gaattcccat tggcagaggc cagatgtaga   540
gcagtcctat gagagtgaga agactttta ggaaattgta gtgcactagc tacagccata   600
gcaatgattc atgtaactgc aaacactgaa tagcctgcta ttactctgcc ttcaaaaaaa   660
aaaaaaaa                                                             668

<210> SEQ ID NO 294
<211> LENGTH: 1512
<212> TYPE: DNA
<213> ORGANISM: Homo sapien

<400> SEQUENCE: 294
gggtcgccca gggggsgcgt gggctttcct cgggtgggtg tgggttttcc ctgggtgggg   60
tgggctgggc trgaatcccc tgctggggtt ggcaggtttt ggctgggatt gacttttytc   120
ttcaaacaga ttggaaaccc ggagttacct gctagttggt gaaactggtt ggtagacgcg   180
atctgttggc tactactggc ttctcctggc tgttaaaagc agatggtggt tgaggttgat   240
```

-continued

| | |
|---|---|
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatgggca agtggtgctg ccactgcttc | 540 |
| ccctgctgca gggggagcrg caagagcaag gtgggcgctt ggggagacta cgatgacagt | 600 |
| gccttcatgg agcccaggta ccacgtccgt ggagaagatc tggacaagct ccacagagct | 660 |
| gcctggtggg gtaaagtccc cagaaaggat ctcatcgtca tgctcaggga cactgacgtg | 720 |
| aacaagaagg acaagcaaaa gaggactgct ctacatctgg cctctgccaa tgggaattca | 780 |
| gaagtagtaa aactcstgct ggacagacga tgtcaactta atgtccttga caacaaaaag | 840 |
| aggacagctc tgayaaaggc cgtacaatgc caggaagatg aatgtgcgtt aatgttgctg | 900 |
| gaacatggca ctgatccaaa tattccagat gagtatggaa ataccactct rcactaygct | 960 |
| rtctayaatg aagataaatt aatggccaaa gcactgctct tatayggtgc tgatatcgaa | 1020 |
| tcaaaaaaca aggtatagat ctactaattt tatcttcaaa atactgaaat gcattcattt | 1080 |
| taacattgac gtgtgtaagg gccagtcttc cgtatttgga agctcaagca taacttgaat | 1140 |
| gaaaatattt tgaaatgacc taattatctm agactttatt ttaaatattg ttattttcaa | 1200 |
| agaagcatta gagggtacag tttttttttt ttaaatgcac ttctggtaaa tacttttgtt | 1260 |
| gaaaacactg aatttgtaaa agtaatact tactattttt caattttcc ctcctaggat | 1320 |
| ttttttcccc taatgaatgt aagatggcaa aatttgccct gaaataggtt ttacatgaaa | 1380 |
| actccaagaa aagttaaaca tgtttcagtg aatagagatc ctgctccttt ggcaagttcc | 1440 |
| taaaaaacag taatagatac gaggtgatgc gcctgtcagt ggcaaggttt aagatatttc | 1500 |
| tgatctcgtg cc | 1512 |

<210> SEQ ID NO 295
<211> LENGTH: 1853
<212> TYPE: DNA
<213> ORGANISM: Homo sapien

<400> SEQUENCE: 295

| | |
|---|---|
| gggtcgccca gggggsgcgt gggctttcct cgggtgggtg tgggttttcc ctgggtgggg | 60 |
| tgggctgggc trgaatcccc tgctggggtt ggcaggtttt ggctgggatt gacttttytc | 120 |
| ttcaaacaga ttggaaaccc ggagttacct gctagttggt gaaactggtt ggtagacgcg | 180 |
| atctgttggc tactactggc ttctcctggc tgttaaaagc agatggtggt tgaggttgat | 240 |
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatgggca agtggtgctg ccactgcttc | 540 |
| ccctgctgca gggggagcrg caagagcaag gtgggcgctt ggggagacta cgatgacagy | 600 |
| gccttcatgg akcccaggta ccacgtccrt ggagaagatc tggacaagct ccacagagct | 660 |
| gcctggtggg gtaaagtccc cagaaaggat ctcatcgtca tgctcaggga cackgaygtg | 720 |
| aacaagargg acaagcaaaa gaggactgct ctacatctgg cctctgccaa tgggaattca | 780 |
| gaagtagtaa aactcstgct ggacagacga tgtcaactta atgtccttga caacaaaaag | 840 |

```
aggacagctc tgayaaaggc cgtacaatgc caggaagatg aatgtgcgtt aatgttgctg      900
gaacatggca ctgatccaaa tattccagat gagtatggaa ataccactct rcactaygct      960
rtctayaatg aagataaatt aatggccaaa gcactgctct tataygqtgc tgatatcgaa     1020 tcaaaaaaca agcatggcct cacaccactg ytacttggtr tacatgagca aaaacagcaa     1080
gtsgtgaaat ttttaatyaa gaaaaagcg aatttaaaat gcrctggata gatatggaag     1140
ractgctctc atacttgctg tatgttgtgg atcagcaagt atagtcagcc ytctacttga     1200
gcaaaatrtt gatgtatctt ctcaagatct ggaaagacgg ccagagagta tgctgtttct     1260
agtcatcatc atgtaatttg ccagttactt tctgactaca agaaaaaca gatgttaaaa       1320 atctcttctg aaaacagcaa tccagaacaa gacttaaagc tgacatcaga ggaagagtca     1380
caaaggctta aggaagtga aacagccag ccagaggcat ggaaactttt aaatttaaac       1440
ttttggttta atgtttttt tttttgcctt aataatatta gatagtccca aatgaaatwa     1500
cctatgagac taggctttga gaatcaatag attctttttt taagaatctt ttggctagga     1560
gcggtgtctc acgcctgtaa ttccagcacc ttgagaggct gaggtgggca gatcacgaga     1620
tcaggagatc gagaccatcc tggctaacac ggtgaaaccc catctctact aaaaatacaa     1680
aaacttagct gggtgtggtg gcgggtgcct gtagtcccag ctactcagga rgctgaggca     1740
ggagaatggc atgaacccgg gaggtggagg ttgcagtgag ccgagatccg ccactacact     1800
ccagcctggg tgacagagca agactctgtc tcaaaaaaaa aaaaaaaaaa aaa            1853

<210> SEQ ID NO 296
<211> LENGTH: 2184
<212> TYPE: DNA
<213> ORGANISM: Homo sapien

<400> SEQUENCE: 296
ggcacgagaa ttaaaaccct cagcaaaaca ggcatagaag ggacataact taaagtaata      60 aaaccacct atgacaagcc cacagccaac ataatactaa atggggaaaa gttagaagca     120
tttcctctga gaactgcaac aataaataca aggatgctgg attttgtcaa atgccttttc     180
tgtgtctgtt gagatgctta tgtgactttg cttttaattc tgtttatgtg attatcacat     240
ttattgactt gcctgtgtta gaccggaaga gctgggtgt ttctcaggag ccaccgtgtg      300
ctgcggcagc ttcgggataa cttgaggctg catcactggg gaagaaacac aytcctgtcc     360
gtggcgctga tggctgagga cagagcttca gtgtggcttc tctgcgactg gcttcttcgg     420
ggagttcttc cttcatagtt catccatatg gctccagagg aaaattatat tattttgtta     480
tggatgaaga gtattacgtt gtgcagatat actgcagtgt cttcatctct tgatgtgtga     540
ttgggtaggt tccaccatgt tgccgcagat gacatgattt cagtacctgt gtctggctga     600
aaagtgtttg tttgtgaatg gatattgtgg tttctggatc tcatcctctg tgggtggaca     660
gctttctcca ccttgctgga agtgacctgc tgtccagaag tttgatggct gaggagtata     720
ccatcgtgca tgcatctttc atttcctgca tttcttcctc cctggatgga cagggggagc     780
ggcaagagca acgtgggcac ttctggagac cacaacgact cctctgtgaa gacgcttggg     840
agcaagaggt gcaagtggtg ctgccactgc ttcccctgct gcaggggagc ggcaagagca     900
acgtggtcgc ttgggagac tacgatgaca gcgccttcat ggatcccagg taccacgtcc     960
atggagaaga tctggacaag ctccacagag ctgcctggtg gggtaaagtc cccagaaagg    1020
atctcatcgt catgctcagg gacacggatg tgaacaagag ggacaagcaa aagaggactg    1080
```

```
ctctacatct ggcctctgcc aatgggaatt cagaagtagt aaaactcgtg ctggacagac    1140
gatgtcaact taatgtcctt gacaacaaaa agaggacagc tctgacaaag gccgtacaat    1200
gccaggaaga tgaatgtgcg ttaatgttgc tggaacatgg cactgatcca atatattccag   1260 atgagtatgg aaataccact ctacactatg ctgtctacaa tgaagataaa ttaatggcca    1320
aagcactgct cttatacggt gctgatatcg aatcaaaaaa caagcatggc ctcacaccac    1380
tgctacttgg tatacatgag caaaaacagc aagtggtgaa attttttaatc aagaaaaaag   1440 cgaatttaaa tgcgctggat agatatggaa gaactgctct catacttgct gtatgttgtg    1500
gatcagcaag tatagtcagc cctctacttg agcaaaatgt tgatgtatct tctcaagatc    1560
tggaaagacg gccagagagt atgctgtttc tagtcatcat catgtaattt gccagttact    1620
ttctgactac aaagaaaaac agatgttaaa aatctcttct gaaaacagca atccagaaca    1680
agacttaaag ctgacatcag aggaagagtc acaaaggctt aaaggaagtg aaaacagcca    1740
gccagaggca tggaaacttt taaatttaaa cttttggttt aatgttttt tttttgcct      1800 taataatatt agatagtccc aaatgaaatw acctatgaga ctaggctttg agaatcaata    1860
gattcttttt ttaagaatct tttggctagg agcggtgtct cacgcctgta attccagcac    1920
cttgagaggc tgaggtgggc agatcacgag atcaggagat cgagaccatc ctggctaaca    1980
cggtgaaacc ccatctctac taaaaataca aaaacttagc tgggtgtggt ggcgggtgcc    2040
tgtagtccca gctactcagg argctgaggc aggagaatgg catgaacccg ggaggtggag    2100
gttgcagtga gccgagatcc gccactacac tccagcctgg gtgacagagc aagactctgt    2160
ctcaaaaaaa aaaaaaaaa aaaa                                            2184
```

<210> SEQ ID NO 297
<211> LENGTH: 1855
<212> TYPE: DNA
<213> ORGANISM: Homo sapien
<220> FEATURE:
<221> NAME/KEY: misc_feature
<222> LOCATION: (1)...(1855)
<223> OTHER INFORMATION: n = A,T,C or G

<400> SEQUENCE: 297

```
tgcacgcatc ggccagtgtc tgtgccacgt acactgacgc cccctgagat gtgcacgccg     60
cacgcgcacg ttgcacgcgc ggcagcggct tggctggctt gtaacggctt gcacgcgcac    120
gccgcccccg cataaccgtc agactggcct gtaacggctt gcaggcgcac gccgcacgcg    180
cgtaacggct tggctgccct gtaacggctt gcacgtgcat gctgcacgcg cgttaacggc    240
ttggctggca tgtagccgct tggcttggct ttgcattytt tgctkggctk ggcgttgkty    300
tcttggattg acgcttcctc cttggatkga cgtttcctcc ttggatkgac gtttcytyty    360
tcgcgttcct ttgctggact tgacctttty tctgctgggt ttggcattcc tttggggtgg    420
gctgggtgtt ttctccgggg gggktkgccc ttcctggggt gggcgtgggk cgccccccagg   480 gggcgtgggc tttccccggg tgggtgtggg ttttcctggg gtggggtggg ctgtgctggg    540
atccccctgc tggggttggc agggattgac ttttttcttc aaacagattg gaaacccgga    600
gtaacntgct agttggtgaa actggttggt agacgcgatc tgctggtact actgtttctc    660
ctggctgtta aaagcagatg gtggctgagg ttgattcaat gccggctgct tcttctgtga    720
agaagccatt tggtctcagg agcaagatgg gcaagtggtg cgccactgct tcccctgctg    780 caggggagc ggcaagagca acgtgggcac ttctggagac acaacgact cctctgtgaa      840 gacgcttggg agcaagaggt gcaagtggtg ctgcccactg cttcccctgc tgcaggggag    900
```

```
cggcaagagc aacgtggkcg cttggggaga ctacgatgac agcgccttca tggakcccag      960
gtaccacgtc crtggagaag atctggacaa gctccacaga gctgcctggt ggggtaaagt     1020
ccccagaaag gatctcatcg tcatgctcag ggacactgay gtgaacaaga rggacaagca     1080
aaagaggact gctctacatc tggcctctgc caatgggaat tcagaagtag taaaactcgt     1140
gctggacaga cgatgtcaac ttaatgtcct tgacaacaaa agaggacag ctctgacaaa      1200
ggccgtacaa tgccaggaag atgaatgtgc gttaatgttg ctggaacatg cactgatcc     1260
aaatattcca gatgagtatg gaaataccac tctacactat gctgtctaca atgaagataa    1320
attaatggcc aaagcactgc tcttatacgg tgctgatatc gaatcaaaaa acaaggtata    1380
gatctactaa ttttatcttc aaaatactga aatgcattca ttttaacatt gacgtgtgta    1440
agggccagtc ttccgtattt ggaagctcaa gcataacttg aatgaaaata ttttgaaatg    1500
acctaattat ctaagacttt attttaaata ttgttatttt caaagaagca ttagagggta    1560
cagttttttt tttttaaatg cacttctggt aaatactttt gttgaaaaca ctgaatttgt    1620
aaaaggtaat acttactatt tttcaatttt tccctcctag gatttttttc ccctaatgaa    1680
tgtaagatgg caaaatttgc cctgaaatag gttttacatg aaaactccaa gaaaagttaa    1740
acatgtttca gtgaatagag atcctgctcc tttggcaagt tcctaaaaaa cagtaataga    1800
tacgaggtga tgcgcctgtc agtggcaagg tttaagatat ttctgatctc gtgcc         1855

<210> SEQ ID NO 298
<211> LENGTH: 1059
<212> TYPE: DNA
<213> ORGANISM: Homo sapien

<400> SEQUENCE: 298
gcaacgtggg cacttctgga gaccacaacg actcctctgt gaagacgctt gggagcaaga      60
ggtgcaagtg gtgctgccca ctgcttcccc tgctgcaggg gagcggcaag agcaacgtgg     120
gcgcttgrgg agactmcgat gacagygcct tcatggagcc caggtaccac gtccgtggag     180
aagatctgga caagctccac agagctgccc tggtggggta aagtccccag aaaggatctc     240
atcgtcatgc tcagggacac tgaygtgaac aagarggaca agcaaaagag gactgctcta     300
catctggcct ctgccaatgg gaattcagaa gtagtaaaac tcstgctgga cagacgatgt     360
caacttaatg tccttgacaa caaaagagg acagctctga yaaggccgt acaatgccag       420
gaagatgaat gtgcgttaat gttgctggaa catggcactg atccaaatat tccagatgag    480
tatggaaata ccactctrca ctaygctrtc tayaatgaag ataaattaat ggccaaagca    540
ctgctcttat ayggtgctga tatcgaatca aaaacaagg tatagatcta ctaattttat    600
cttcaaaata ctgaaatgca ttcattttaa cattgacgtg tgtaagggcc agtcttccgt    660
atttggaagc tcaagcataa cttgaatgaa aatattttga aatgacctaa ttatctaaga    720
ctttattta aatattgtta ttttcaaaga agcattagag ggtacagttt tttttttta      780
aatgcacttc tggtaaatac ttttgttgaa aacactgaat ttgtaaaagg taatacttac    840
tattttcaa tttttccctc ctaggattt tttcccctaa tgaatgtaag atggcaaaat     900
ttgccctgaa ataggtttta catgaaaact ccaagaaaag ttaaacatgt ttcagtgaat    960
agagatcctg ctcctttggc aagttcctaa aaaacagtaa tagatacgag gtgatgcgcc   1020
tgtcagtggc aaggtttaag atatttctga tctcgtgcc                          1059

<210> SEQ ID NO 299
```

```
<211> LENGTH: 329
<212> TYPE: PRT
<213> ORGANISM: Homo sapien

<400> SEQUENCE: 299

Met Asp Ile Val Val Ser Gly Ser His Pro Leu Trp Val Asp Ser Phe
1               5                   10                  15

Leu His Leu Ala Gly Ser Asp Leu Leu Ser Arg Ser Leu Met Ala Glu
            20                  25                  30

Glu Tyr Thr Ile Val His Ala Ser Phe Ile Ser Cys Ile Ser Ser Ser
        35                  40                  45

Leu Asp Gly Gln Gly Glu Arg Gln Glu Gln Arg Gly His Phe Trp Arg
    50                  55                  60

Pro Gln Arg Leu Leu Cys Glu Asp Ala Trp Glu Gln Glu Val Gln Val
65                  70                  75                  80

Val Leu Pro Leu Leu Pro Leu Leu Gln Gly Ser Gly Lys Ser Asn Val
                85                  90                  95

Val Ala Trp Gly Asp Tyr Asp Asp Ser Ala Phe Met Asp Pro Arg Tyr
            100                 105                 110

His Val His Gly Glu Asp Leu Asp Lys Leu His Arg Ala Ala Trp Trp
        115                 120                 125

Gly Lys Val Pro Arg Lys Asp Leu Ile Val Met Leu Arg Asp Thr Asp
    130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
                165                 170                 175

Gln Leu Asn Val Leu Asp Asn Lys Lys Arg Thr Ala Leu Thr Lys Ala
            180                 185                 190

Val Gln Cys Gln Glu Asp Glu Cys Ala Leu Met Leu Leu Glu His Gly
        195                 200                 205

Thr Asp Pro Asn Ile Pro Asp Glu Tyr Gly Asn Thr Thr Leu His Tyr
    210                 215                 220

Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
                245                 250                 255

Leu Gly Ile His Glu Gln Lys Gln Val Val Lys Phe Leu Ile Lys
            260                 265                 270

Lys Lys Ala Asn Leu Asn Ala Leu Asp Arg Tyr Gly Arg Thr Ala Leu
        275                 280                 285

Ile Leu Ala Val Cys Cys Gly Ser Ala Ser Ile Val Ser Pro Leu Leu
    290                 295                 300

Glu Gln Asn Val Asp Val Ser Ser Gln Asp Leu Glu Arg Arg Pro Glu
305                 310                 315                 320

Ser Met Leu Phe Leu Val Ile Ile Met
                325

<210> SEQ ID NO 300
<211> LENGTH: 148
<212> TYPE: PRT
<213> ORGANISM: Homo sapien
<220> FEATURE:
<221> NAME/KEY: VARIANT
<222> LOCATION: (1)...(148)
<223> OTHER INFORMATION: Xaa = Any Amino Acid
```

-continued

```
<400> SEQUENCE: 300

Met Thr Xaa Pro Ser Trp Ser Pro Gly Thr Thr Ser Val Glu Lys Ile
1               5                   10                  15

Trp Thr Ser Ser Thr Glu Leu Pro Trp Trp Gly Lys Val Pro Arg Lys
            20                  25                  30

Asp Leu Ile Val Met Leu Arg Asp Thr Asp Val Asn Lys Xaa Asp Lys
        35                  40                  45

Gln Lys Arg Thr Ala Leu His Leu Ala Ser Ala Asn Gly Asn Ser Glu
    50                  55                  60

Val Val Lys Leu Xaa Leu Asp Arg Arg Cys Gln Leu Asn Val Leu Asp
65                  70                  75                  80

Asn Lys Lys Arg Thr Ala Leu Xaa Lys Ala Val Gln Cys Gln Glu Asp
                85                  90                  95

Glu Cys Ala Leu Met Leu Leu Glu His Gly Thr Asp Pro Asn Ile Pro
            100                 105                 110

Asp Glu Tyr Gly Asn Thr Thr Leu His Tyr Ala Xaa Tyr Asn Glu Asp
        115                 120                 125

Lys Leu Met Ala Lys Ala Leu Leu Leu Tyr Gly Ala Asp Ile Glu Ser
    130                 135                 140

Lys Asn Lys Val
145

<210> SEQ ID NO 301
<211> LENGTH: 1155
<212> TYPE: DNA
<213> ORGANISM: Homo sapien

<400> SEQUENCE: 301
atggtggttg aggttgattc catgccggct gcctcttctg tgaagaagcc atttggtctc      60
aggagcaaga tgggcaagtg gtgctgccgt tgcttcccct gctgcaggga gagcggcaag     120
agcaacgtgg gcacttctgg agaccacgac gactctgcta tgaagacact caggagcaag     180
atgggcaagt ggtgccgcca ctgcttcccc tgctgcaggg ggagtggcaa gagcaacgtg     240
ggcgcttctg gagaccacga cgactctgct atgaagacac tcaggaacaa gatgggcaag     300
tggtgctgcc actgcttccc ctgctgcagg gggagcggca gagcaaggt gggcgcttgg      360 ggagactacg atgacagtgc cttcatggag cccaggtacc acgtccgtgg agaagatctg     420
gacaagctcc acagagctgc ctggtgggt aaagtcccca gaaggatct catcgtcatg       480 ctcagggaca ctgacgtgaa caagaaggac aagcaaaaga ggactgctct acatctggcc     540
tctgccaatg ggaattcaga agtagtaaaa ctcctgctgg acagacgatg tcaacttaat     600
gtccttgaca caaaaagag gacagctctg ataaaggccg tacaatgcca ggaagatgaa      660
tgtgcgttaa tgttgctgga acatggcact gatccaaata ttccagatga gtatggaaat     720
accactctgc actacgctat ctataatgaa gataaattaa tggccaaagc actgctctta     780
tatggtgctg atatcgaatc aaaaaacaag catggcctca caccactgtt acttggtgta     840
catgagcaaa acagcaagt cgtgaaattt taatcaaga aaaagcgaa tttaaatgca       900 ctggatagat atggaaggac tgctctcata cttgctgtat gttgtggatc agcaagtata     960
gtcagccttc tacttgagca aaatattgat gtatcttctc aagatctatc tggacagacg    1020
gccagagagt atgctgtttc tagtcatcat catgtaattt gccagttact ttctgactac    1080
aaagaaaaac agatgctaaa aatctcttct gaaaacagca atccagaaaa tgtctcaaga    1140
accagaaaat aataa                                                     1155
```

<210> SEQ ID NO 302
<211> LENGTH: 2000
<212> TYPE: DNA
<213> ORGANISM: Homo sapien

<400> SEQUENCE: 302

| | | | | | |
|---|---|---|---|---|---|
| atggtggttg | aggttgattc | catgccggct | gcctcttctg | tgaagaagcc | atttggtctc | 60 |
| aggagcaaga | tgggcaagtg | gtgctgccgt | tgcttcccct | gctgcaggga | gagcggcaag | 120 |
| agcaacgtgg | gcacttctgg | agaccacgac | gactctgcta | tgaagacact | caggagcaag | 180 |
| atgggcaagt | ggtgccgcca | ctgcttcccc | tgctgcaggg | ggagtggcaa | gagcaacgtg | 240 |
| ggcgcttctg | gagaccacga | cgactctgct | atgaagacac | tcaggaacaa | gatgggcaag | 300 |
| tggtgctgcc | actgcttccc | ctgctgcagg | gggagcggca | agagcaaggt | gggcgcttgg | 360 |
| ggagactacg | atgacagtgc | cttcatggag | cccaggtacc | acgtccgtgg | agaagatctg | 420 |
| gacaagctcc | acagagctgc | ctggtggggt | aaagtcccca | gaaaggatct | catcgtcatg | 480 |
| ctcagggaca | ctgacgtgaa | caagaaggac | aagcaaaaga | ggactgctct | acatctggcc | 540 |
| tctgccaatg | ggaattcaga | agtagtaaaa | ctcctgctgg | acagacgatg | tcaacttaat | 600 |
| gtccttgaca | caaaaagag | gacagctctg | ataaaggccg | tacaatgcca | ggaagatgaa | 660 |
| tgtgcgttaa | tgttgctgga | acatggcact | gatccaaata | ttccagatga | gtatggaaat | 720 |
| accactctgc | tactcgctat | ctataatgaa | gataaattaa | tggccaaagc | actgctctta | 780 |
| tatggtgctg | atatcgaatc | aaaaaacaag | catggcctca | caccactgtt | acttggtgta | 840 |
| catgagcaaa | acagcaagt | cgtgaaattt | ttaatcaaga | aaaaagcgaa | tttaaatgca | 900 |
| ctggatagat | atggaaggac | tgctctcata | cttgctgtat | gttgtggatc | agcaagtata | 960 |
| gtcagccttc | tacttgagca | aaatattgat | gtatcttctc | aagatctatc | tggacagacg | 1020 |
| gccagagagt | atgctgtttc | tagtcatcat | catgtaattt | gccagttact | ttctgactac | 1080 |
| aaagaaaaac | agatgctaaa | aatctcttct | gaaaacagca | atccagaaca | agacttaaag | 1140 |
| ctgacatcag | aggaagagtc | acaaaggttc | aaaggcagtg | aaaatagcca | gccagagaaa | 1200 |
| atgtctcaag | aaccagaaat | aaataaggat | ggtgatagag | aggttgaaga | agaaatgaag | 1260 |
| aagcatgaaa | gtaataatgt | gggattacta | gaaaacctga | ctaatggtgt | cactgctggc | 1320 |
| aatggtgata | atggattaat | tcctcaaagg | aagagcagaa | cacctgaaaa | tcagcaattt | 1380 |
| cctgacaacg | aaagtgaaga | gtatcacaga | atttgcgaat | tagtttctga | ctacaaagaa | 1440 |
| aaacagatgc | caaatactc | ttctgaaaac | agcaacccag | aacaagactt | aaagctgaca | 1500 |
| tcagaggaag | agtcacaaag | gcttgagggc | agtgaaaatg | ccagccaga | gctagaaaat | 1560 |
| tttatggcta | tcgaagaaat | gaagaagcac | ggaagtactc | atgtcggatt | cccagaaaac | 1620 |
| ctgactaatg | gtgccactgc | tggcaatggt | gatgatggat | taattcctcc | aaggaagagc | 1680 |
| agaacacctg | aaagccagca | atttcctgac | actgagaatg | aagagtatca | cagtgacgaa | 1740 |
| caaaatgata | ctcagaagca | attttgtgaa | gaacagaaca | ctggaatatt | acacgatgag | 1800 |
| attctgattc | atgaagaaaa | gcagatagaa | gtggttgaaa | aatgaattc | tgagctttct | 1860 |
| cttagttgta | agaagaaaa | agacatcttg | catgaaaata | gtacgttgcg | ggaagaaatt | 1920 |
| gccatgctaa | gactggagct | agacacaatg | aaacatcaga | gccagctaaa | aaaaaaaaa | 1980 |
| aaaaaaaaaa | aaaaaaaaaa | | | | | 2000 |

<210> SEQ ID NO 303

<211> LENGTH: 2040
<212> TYPE: DNA
<213> ORGANISM: Homo sapien

<400> SEQUENCE: 303

| | | | | | |
|---|---|---|---|---|---|
| atggtggttg | aggttgattc | catgccggct | gcctcttctg | tgaagaagcc | atttggtctc | 60 |
| aggagcaaga | tgggcaagtg | gtgctgccgt | tgcttcccct | gctgcaggga | gagcggcaag | 120 |
| agcaacgtgg | gcacttctgg | agaccacgac | gactctgcta | tgaagacact | caggagcaag | 180 |
| atgggcaagt | ggtgccgcca | ctgcttcccc | tgctgcaggg | ggagtggcaa | gagcaacgtg | 240 |
| ggcgcttctg | gagaccacga | cgactctgct | atgaagacac | tcaggaacaa | gatgggcaag | 300 |
| tggtgctgcc | actgcttccc | ctgctgcagg | gggagcggca | agagcaaggt | gggcgcttgg | 360 |
| ggagactacg | atgacagtgc | cttcatggag | cccaggtacc | acgtccgtgg | agaagatctg | 420 |
| gacaagctcc | acagagctgc | ctggtggggt | aaagtcccca | gaaaggatct | catcgtcatg | 480 |
| ctcagggaca | ctgacgtgaa | caagaaggac | aagcaaaaga | ggactgctct | acatctggcc | 540 |
| tctgccaatg | ggaattcaga | agtagtaaaa | ctcctgctgg | acagacgatg | tcaacttaat | 600 |
| gtccttgaca | caaaaagag | gacagctctg | ataaaggccg | tacaatgcca | ggaagatgaa | 660 |
| tgtgcgttaa | tgttgctgga | acatggcact | gatccaaata | ttccagatga | gtatggaaat | 720 |
| accactctgc | actacgctat | ctataatgaa | gataaattaa | tggccaaagc | actgctctta | 780 |
| tatggtgctg | atatcgaatc | aaaaaacaag | catggcctca | caccactgtt | acttggtgta | 840 |
| catgagcaaa | acagcaagt | cgtgaaattt | ttaatcaaga | aaaagcgaa | tttaaatgca | 900 |
| ctggatagat | atggaaggac | tgctctcata | cttgctgtat | gttgtggatc | agcaagtata | 960 |
| gtcagccttc | tacttgagca | aaatattgat | gtatcttctc | aagatctatc | tggacagacg | 1020 |
| gccagagagt | atgctgtttc | tagtcatcat | catgtaattt | gccagttact | ttctgactac | 1080 |
| aaagaaaaac | agatgctaaa | aatctcttct | gaaacagca | atccagaaca | agacttaaag | 1140 |
| ctgacatcag | aggaagagtc | acaaggttc | aaggcagtg | aaaatagcca | gccagagaaa | 1200 |
| atgtctcaag | aaccagaaat | aaataaggat | ggtgatagag | aggttgaaga | agaaatgaag | 1260 |
| aagcatgaaa | gtaataatgt | gggattacta | gaaaacctga | ctaatggtgt | cactgctggc | 1320 |
| aatggtgata | atggattaat | tcctcaaagg | aagagcagaa | cacctgaaaa | tcagcaatt | 1380 |
| cctgacaacg | aaagtgaaga | gtatcacaga | atttgcgaat | tagtttctga | ctacaaagaa | 1440 |
| aaacagatgc | caaatactc | ttctgaaaac | agcaacccag | aacaagactt | aaagctgaca | 1500 |
| tcagaggaag | agtcacaaag | gcttgagggc | agtgaaaatg | ccagccaga | gaaagatct | 1560 |
| caagaaccag | aaataaataa | ggatggtgat | agagagctag | aaaattttat | ggctatcgaa | 1620 |
| gaaatgaaga | agcacggaag | tactcatgtc | ggattcccag | aaaacctgac | taatggtgcc | 1680 |
| actgctggca | atggtgatga | tggattaatt | cctccaagga | agagcagaac | acctgaaagc | 1740 |
| cagcaatttc | ctgacactga | gaatgaagag | tatcacagtg | acgaacaaaa | tgatactcag | 1800 |
| aagcaatttt | gtgaagaaca | gaacactgga | atattacacg | atgagattct | gattcatgaa | 1860 |
| gaaaagcaga | tagaagtggt | tgaaaaaatg | aattctgagc | tttctcttag | ttgtaagaaa | 1920 |
| gaaaagaca | tcttgcatga | aaatagtacg | ttgcgggaag | aaattgccat | gctaagactg | 1980 |
| gagctagaca | caatgaaaca | tcagagccag | ctaaaaaaaa | aaaaaaaaaa | aaaaaaaaaa | 2040 |

<210> SEQ ID NO 304
<211> LENGTH: 384
<212> TYPE: PRT
<213> ORGANISM: Homo sapien

```
<400> SEQUENCE: 304

Met Val Val Glu Val Asp Ser Met Pro Ala Ala Ser Ser Val Lys Lys
  1               5                  10                  15

Pro Phe Gly Leu Arg Ser Lys Met Gly Lys Trp Cys Cys Arg Cys Phe
             20                  25                  30

Pro Cys Cys Arg Glu Ser Gly Lys Ser Asn Val Gly Thr Ser Gly Asp
         35                  40                  45

His Asp Asp Ser Ala Met Lys Thr Leu Arg Ser Lys Met Gly Lys Trp
 50                  55                  60

Cys Arg His Cys Phe Pro Cys Arg Gly Ser Gly Lys Ser Asn Val
 65                  70                  75                  80

Gly Ala Ser Gly Asp His Asp Ser Ala Met Lys Thr Leu Arg Asn
                 85                  90                  95

Lys Met Gly Lys Trp Cys Cys His Cys Phe Pro Cys Arg Gly Ser
                100                 105                 110

Gly Lys Ser Lys Val Gly Ala Trp Gly Asp Tyr Asp Ser Ala Phe
            115                 120                 125

Met Glu Pro Arg Tyr His Val Arg Gly Glu Asp Leu Asp Lys Leu His
130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
                180                 185                 190

Leu Asp Arg Arg Cys Gln Leu Asn Val Leu Asp Asn Lys Lys Arg Thr
            195                 200                 205

Ala Leu Ile Lys Ala Val Gln Cys Gln Glu Asp Glu Cys Ala Leu Met
210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Ala Asn Leu Asn Ala Leu Asp Arg Tyr
290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

<210> SEQ ID NO 305
<211> LENGTH: 656
<212> TYPE: PRT
```

```
<213> ORGANISM: Homo sapien

<400> SEQUENCE: 305

Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
             20                  25                  30

Pro Cys Cys Arg Glu Ser Gly Lys Ser Asn Val Gly Thr Ser Gly Asp
             35                  40                  45

His Asp Asp Ser Ala Met Lys Thr Leu Arg Ser Lys Met Gly Lys Trp
 50                  55                  60

Cys Arg His Cys Phe Pro Cys Cys Arg Gly Ser Gly Lys Ser Asn Val
 65                  70                  75                  80

Gly Ala Ser Gly Asp His Asp Ser Ala Met Lys Thr Leu Arg Asn
             85                  90                  95

Lys Met Gly Lys Trp Cys Cys His Cys Phe Pro Cys Cys Arg Gly Ser
             100                 105                 110

Gly Lys Ser Lys Val Gly Ala Trp Gly Asp Tyr Asp Asp Ser Ala Phe
             115                 120                 125

Met Glu Pro Arg Tyr His Val Arg Gly Glu Asp Leu Asp Lys Leu His
             130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                 165                 170                 175

Leu His Leu Ala Ser Ala Asn Gly Asn Ser Glu Val Val Lys Leu Leu
                 180                 185                 190

Leu Asp Arg Arg Cys Gln Leu Asn Val Leu Asp Asn Lys Lys Arg Thr
             195                 200                 205

Ala Leu Ile Lys Ala Val Gln Cys Gln Glu Asp Glu Cys Ala Leu Met
210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                 245                 250                 255

Ala Leu Leu Leu Tyr Gly Ala Asp Ile Glu Ser Lys Asn Lys His Gly
             260                 265                 270

Leu Thr Pro Leu Leu Leu Gly Val His Glu Gln Lys Gln Gln Val Val
             275                 280                 285

Lys Phe Leu Ile Lys Lys Ala Asn Leu Asn Ala Leu Asp Arg Tyr
             290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                 325                 330                 335

Ser Gly Gln Thr Ala Arg Glu Tyr Ala Val Ser Ser His His His Val
             340                 345                 350

Ile Cys Gln Leu Leu Ser Asp Tyr Lys Glu Lys Gln Met Leu Lys Ile
             355                 360                 365

Ser Ser Glu Asn Ser Asn Pro Glu Gln Asp Leu Lys Leu Thr Ser Glu
             370                 375                 380

Glu Glu Ser Gln Arg Phe Lys Gly Ser Glu Asn Ser Gln Pro Glu Lys
385                 390                 395                 400
```

```
Met Ser Gln Glu Pro Glu Ile Asn Lys Asp Gly Asp Arg Val Glu
            405                 410                 415
Glu Glu Met Lys Lys His Glu Ser Asn Asn Val Gly Leu Leu Glu Asn
        420                 425                 430
Leu Thr Asn Gly Val Thr Ala Gly Asn Gly Asp Asn Gly Leu Ile Pro
        435                 440                 445
Gln Arg Lys Ser Arg Thr Pro Glu Asn Gln Gln Phe Pro Asp Asn Glu
        450                 455                 460
Ser Glu Glu Tyr His Arg Ile Cys Glu Leu Val Ser Asp Tyr Lys Glu
465                 470                 475                 480
Lys Gln Met Pro Lys Tyr Ser Ser Glu Asn Ser Asn Pro Glu Gln Asp
            485                 490                 495
Leu Lys Leu Thr Ser Glu Glu Ser Gln Arg Leu Glu Gly Ser Glu
            500                 505                 510
Asn Gly Gln Pro Glu Leu Glu Asn Phe Met Ala Ile Glu Glu Met Lys
            515                 520                 525
Lys His Gly Ser Thr His Val Gly Phe Pro Glu Asn Leu Thr Asn Gly
    530                 535                 540
Ala Thr Ala Gly Asn Gly Asp Asp Gly Leu Ile Pro Pro Arg Lys Ser
545                 550                 555                 560
Arg Thr Pro Glu Ser Gln Gln Phe Pro Asp Thr Glu Asn Glu Glu Tyr
            565                 570                 575
His Ser Asp Glu Gln Asn Asp Thr Gln Lys Gln Phe Cys Glu Glu Gln
            580                 585                 590
Asn Thr Gly Ile Leu His Asp Glu Ile Leu Ile His Glu Lys Gln
            595                 600                 605
Ile Glu Val Val Glu Lys Met Asn Ser Glu Leu Ser Leu Ser Cys Lys
        610                 615                 620
Lys Glu Lys Asp Ile Leu His Glu Asn Ser Thr Leu Arg Glu Glu Ile
625                 630                 635                 640
Ala Met Leu Arg Leu Glu Leu Asp Thr Met Lys His Gln Ser Gln Leu
            645                 650                 655

<210> SEQ ID NO 306
<211> LENGTH: 671
<212> TYPE: PRT
<213> ORGANISM: Homo sapien

<400> SEQUENCE: 306

Met Val Val Glu Val Asp Ser Met Pro Ala Ser Ser Val Lys Lys
1               5                   10                  15
Pro Phe Gly Leu Arg Ser Lys Met Gly Lys Trp Cys Cys Arg Cys Phe
            20                  25                  30
Pro Cys Cys Arg Glu Ser Gly Lys Ser Asn Val Gly Thr Ser Gly Asp
        35                  40                  45
His Asp Asp Ser Ala Met Lys Thr Leu Arg Ser Lys Met Gly Lys Trp
    50                  55                  60
Cys Arg His Cys Phe Pro Cys Cys Arg Gly Ser Gly Lys Ser Asn Val
65                  70                  75                  80
Gly Ala Ser Gly Asp His Asp Asp Ser Ala Met Lys Thr Leu Arg Asn
            85                  90                  95
Lys Met Gly Lys Trp Cys Cys His Cys Phe Pro Cys Cys Arg Gly Ser
            100                 105                 110
Gly Lys Ser Lys Val Gly Ala Trp Gly Asp Tyr Asp Asp Ser Ala Phe
        115                 120                 125
```

-continued

```
Met Glu Pro Arg Tyr His Val Arg Gly Glu Asp Leu Asp Lys Leu His
    130                 135                 140
Arg Ala Ala Trp Trp Gly Lys Val Pro Arg Lys Asp Leu Ile Val Met
145                 150                 155                 160
Leu Arg Asp Thr Asp Val Asn Lys Lys Asp Lys Gln Lys Arg Thr Ala
                165                 170                 175
Leu His Leu Ala Ser Ala Asn Gly Asn Ser Glu Val Val Lys Leu Leu
                180                 185                 190
Leu Asp Arg Arg Cys Gln Leu Asn Val Leu Asp Asn Lys Lys Arg Thr
                195                 200                 205
Ala Leu Ile Lys Ala Val Gln Cys Gln Glu Asp Glu Cys Ala Leu Met
    210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
                245                 250                 255
Ala Leu Leu Leu Tyr Gly Ala Asp Ile Glu Ser Lys Asn Lys His Gly
                260                 265                 270
Leu Thr Pro Leu Leu Gly Val His Glu Gln Lys Gln Gln Val Val
                275                 280                 285
Lys Phe Leu Ile Lys Lys Ala Asn Leu Asn Ala Leu Asp Arg Tyr
    290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
                325                 330                 335
Ser Gly Gln Thr Ala Arg Glu Tyr Ala Val Ser Ser His His His Val
                340                 345                 350
Ile Cys Gln Leu Leu Ser Asp Tyr Lys Glu Lys Gln Met Leu Lys Ile
    355                 360                 365
Ser Ser Glu Asn Ser Asn Pro Glu Gln Asp Leu Lys Leu Thr Ser Glu
370                 375                 380
Glu Glu Ser Gln Arg Phe Lys Gly Ser Glu Asn Ser Gln Pro Glu Lys
385                 390                 395                 400
Met Ser Gln Glu Pro Glu Ile Asn Lys Asp Gly Asp Arg Glu Val Glu
                405                 410                 415
Glu Glu Met Lys Lys His Glu Ser Asn Asn Val Gly Leu Leu Glu Asn
                420                 425                 430
Leu Thr Asn Gly Val Thr Ala Gly Asn Gly Asp Asn Gly Leu Ile Pro
                435                 440                 445
Gln Arg Lys Ser Arg Thr Pro Glu Asn Gln Gln Phe Pro Asp Asn Glu
    450                 455                 460
Ser Glu Glu Tyr His Arg Ile Cys Glu Leu Val Ser Asp Tyr Lys Glu
465                 470                 475                 480
Lys Gln Met Pro Lys Tyr Ser Ser Glu Asn Ser Asn Pro Glu Gln Asp
                485                 490                 495
Leu Lys Leu Thr Ser Glu Glu Ser Gln Arg Leu Glu Gly Ser Glu
                500                 505                 510
Asn Gly Gln Pro Glu Lys Arg Ser Gln Glu Pro Glu Ile Asn Lys Asp
    515                 520                 525
Gly Asp Arg Glu Leu Glu Asn Phe Met Ala Ile Glu Glu Met Lys Lys
530                 535                 540
```

```
His Gly Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
            565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
            595                 600                 605

Thr Gly Ile Leu His Asp Glu Ile Leu Ile His Glu Glu Lys Gln Ile
            610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
            645                 650                 655

Met Leu Arg Leu Glu Leu Asp Thr Met Lys His Gln Ser Gln Leu
            660                 665                 670

<210> SEQ ID NO 307
<211> LENGTH: 800
<212> TYPE: DNA
<213> ORGANISM: Homo sapien

<400> SEQUENCE: 307
atkagcttcc gcttctgaca acactagaga tccctcccct ccctcagggt atggccctcc     60
acttcatttt tggtacataa catctttata ggacaggggt aaaatcccaa tactaacagg    120
agaatgctta ggactctaac aggttttga gaatgtgttg gtaagggcca ctcaatccaa    180
tttttcttgg tcctccttgt ggtctaggag gacaggcaag ggtgcagatt ttcaagaatg    240
catcagtaag ggccactaaa tccgaccttc ctcgttcctc cttgtggtct gggaggaaaa    300
ctagtgtttc tgttgctgtg tcagtgagca caactattcc gatcagcagg gtccagggac    360
cactgcaggt tcttgggcag ggggagaaac aaaacaaacc aaaaccatgg gcrgttttgt    420 cttcagatg ggaaacactc aggcatcaac aggctccacct ttgaaatgca tcctaagcca    480
atgggacaaa tttgacccac aaaccctgga aaaagaggtg gctcattttt tttgcactat    540
ggcttggccc caacattctc tctctgatgg ggaaaaatgg ccacctgagg gaagtacaga    600
ttacaatact atcctgcagc ttgacctttt ctgtaagagg gaaggcaaat ggagtgaaat    660
accttatgtc caagctttct tttcattgaa ggagaataca ctatgcaaag cttgaaattt    720
acatcccaca ggaggacctc tcagcttacc cccatatcct agcctcccta tagctcccct    780
tcctattagt gataagcctc                                                800

<210> SEQ ID NO 308
<211> LENGTH: 102
<212> TYPE: PRT
<213> ORGANISM: Homo sapien
<220> FEATURE:
<221> NAME/KEY: VARIANT
<222> LOCATION: (1)...(102)
<223> OTHER INFORMATION: Xaa = Any Amino Acid

<400> SEQUENCE: 308

Met Gly Xaa Phe Val Phe Gln Met Gly Asn Thr Gln Ala Ser Thr Gly
  1               5                  10                  15

Ser Pro Leu Lys Cys Ile Leu Ser Gln Trp Asp Lys Phe Asp Pro Gln
            20                  25                  30

Thr Leu Glu Lys Glu Val Ala His Phe Phe Cys Thr Met Ala Trp Pro
```

```
              35                  40                  45
Gln His Ser Leu Ser Asp Gly Glu Lys Trp Pro Pro Glu Gly Ser Thr
         50                  55                  60

Asp Tyr Asn Thr Ile Leu Gln Leu Asp Leu Phe Cys Lys Arg Glu Gly
 65                  70                  75                  80

Lys Trp Ser Glu Ile Pro Tyr Val Gln Ala Phe Phe Ser Leu Lys Glu
                 85                  90                  95

Asn Thr Leu Cys Lys Ala
            100
```

<210> SEQ ID NO 309
<211> LENGTH: 9
<212> TYPE: PRT
<213> ORGANISM: Artificial Sequence
<220> FEATURE:
<223> OTHER INFORMATION: Made in the lab

<400> SEQUENCE: 309

```
Leu Met Ala Glu Glu Tyr Thr Ile Val
 1               5
```

<210> SEQ ID NO 310
<211> LENGTH: 9
<212> TYPE: PRT
<213> ORGANISM: Artificial Sequence
<220> FEATURE:
<223> OTHER INFORMATION: Made in the lab

<400> SEQUENCE: 310

```
Lys Leu Met Ala Lys Ala Leu Leu Leu
 1               5
```

<210> SEQ ID NO 311
<211> LENGTH: 9
<212> TYPE: PRT
<213> ORGANISM: Artificial Sequence
<220> FEATURE:
<223> OTHER INFORMATION: Made in the lab

<400> SEQUENCE: 311

```
Gly Leu Thr Pro Leu Leu Leu Gly Ile
 1               5
```

<210> SEQ ID NO 312
<211> LENGTH: 10
<212> TYPE: PRT
<213> ORGANISM: Artificial Sequence
<220> FEATURE:
<223> OTHER INFORMATION: Made in the lab

<400> SEQUENCE: 312

```
Lys Leu Val Leu Asp Arg Arg Cys Gln Leu
 1               5                  10
```

<210> SEQ ID NO 313
<211> LENGTH: 1852
<212> TYPE: DNA
<213> ORGANISM: Homo sapiens

<400> SEQUENCE: 313

```
ggcacgagaa ttaaaaccct cagcaaaaca ggcatagaag ggacatacct taaagtaata      60
aaaaccacct atgacaagcc cacagccaac ataatactaa atggggaaaa gttagaagca     120
tttcctctga gaactgcaac aataaataca aggatgctgg attttgtcaa atgccttttc     180
```

```
tgtgtctgtt gagatgctta tgtgactttg cttttaattc tgtttatgtg attatcacat     240
ttattgactt gcctgtgtta gaccggaaga gctggggtgt ttctcaggag ccaccgtgtg     300
ctgcggcagc ttcgggataa cttgaggctg catcactggg aagaaacac aytcctgtcc      360 gtggcgctga tggctgagga cagagcttca gtgtggcttc tctgcgactg gcttcttcgg     420
ggagttcttc cttcatagtt catccatatg gctccagagg aaaattatat tattttgtta    480
tggatgaaga gtattacgtt gtgcagatat actgcagtgt cttcatctct gatgtgtga     540 ttgggtaggt tccaccatgt tgccgcagat gacatgattt cagtacctgt gtctggctga    600
aaagtgtttg tttgtgaatg gatattgtgg tttctggatc tcatcctctg tgggtggaca    660
gctttctcca ccttgctgga agtgacctgc tgtccagaag tttgatggct gaggagtata    720
ccatcgtgca tgcatctttc atttcctgca tttcttcctc cctggatgga caggggagc     780 ggcaagagca acgtgggcac ttctggagac cacaacgact cctctgtgaa gacgcttggg    840
agcaagaggt gcaagtggtg ctgccactgc ttcccctgct gcaggggag cggcaagagc     900 aacgtggtcg cttggggaga ctacgatgac agcgccttca tggatcccag gtaccacgtc    960
catggagaag atctggacaa gctccacaga gctgcctggt ggggtaaagt ccccagaaag   1020
gatctcatcg tcatgctcag ggacacggat gtgaacaaga gggacaagca aaagaggact   1080
gctctacatc tggcctctgc caatgggaat tcagaagtag taaaactcgt gctggacaga   1140
cgatgtcaac ttaatgtcct tgacaacaaa agaggacga ctctgacaaa ggccgtacaa     1200
tgccaggaag atgaatgtgc gttaatgttg ctggaacatg cactgatcc aaatattcca     1260 gatgagtatg gaaataccac tctacactat gctgtctaca atgaagataa attaatggcc   1320
aaagcactgc tcttatacgg tgctgatatc gaatcaaaaa acaagcatgg cctcacacca   1380
ctgctacttg gtatacatga gcaaaaacag caagtggtga aatttttaat caagaaaaaa   1440
gcgaatttaa atgcgctgga tagatatgga agaactgctc tcatacttgc tgtatgttgt   1500
ggatcagcaa gtatagtcag ccctctactt gagcaaaatg ttgatgtatc ttctcaagat   1560
ctggaaagac ggccagagag tatgctgttt ctagtcatca tcatgtaatt tgccagttac   1620
tttctgacta caaagaaaaa cagatgttaa aaatctcttc tgaaaacagc aatccagaac   1680
aagacttaaa gctgacatca gaggaagagt cacaaaggct taaggaagt gaaaacagcc     1740 agccagagct agaagattta tggctattga agaagaatga agaacacgga agtactcatg   1800
tgggattccc agaaaacctg actaacggtg ccgctgctgg caatggtgat ga            1852

<210> SEQ ID NO 314
<211> LENGTH: 879
<212> TYPE: DNA
<213> ORGANISM: Homo sapiens

<400> SEQUENCE: 314
atgcatcttt catttcctgc atttcttcct ccctggatgg acaggggag cggcaagagc      60 aacgtgggca cttctggaga ccacaacgac tcctctgtga agacgcttgg gagcaagagg    120
tgcaagtggt gctgccactg cttcccctgc tgcaggggga gcggcaagag caacgtggtc    180
gcttggggag actacgatga cagcgccttc atggatccca ggtaccacgt ccatggagaa    240
gatctggaca agctccacag agctgcctgg tggggtaaag tccccagaaa ggatctcatc    300
gtcatgctca gggacacgga tgtgaacaag agggacaagc aaaagaggac tgctctacat    360
ctggcctctg ccaatgggaa ttcagaagta gtaaaactcg tgctggacag acgatgtcaa    420
```

-continued

```
cttaatgtcc ttgacaacaa aaagaggaca gctctgacaa aggccgtaca atgccaggaa      480
gatgaatgtg cgttaatgtt gctggaacat ggcactgatc caaatattcc agatgagtat      540
ggaaatacca ctctacacta tgctgtctac aatgaagata aattaatggc caaagcactg      600
ctcttatacg gtgctgatat cgaatcaaaa acaagcatg gcctcacacc actgctactt       660
ggtatacatg agcaaaaaca gcaagtggtg aaattttttaa tcaagaaaaa agcgaattta     720
aatgcgctgg atagatatgg aagaactgct ctcatacttg ctgtatgttg tggatcagca      780
agtatagtca gccctctact tgagcaaaat gttgatgtat cttctcaaga tctggaaaga      840
cggccagaga gtatgctgtt tctagtcatc atcatgtaa                             879
```

<210> SEQ ID NO 315
<211> LENGTH: 292
<212> TYPE: PRT
<213> ORGANISM: Homo sapiens

<400> SEQUENCE: 315

```
Met His Leu Ser Phe Pro Ala Phe Leu Pro Pro Trp Met Asp Arg Gly
                  5                  10                  15

Ser Gly Lys Ser Asn Val Gly Thr Ser Gly Asp His Asn Asp Ser Ser
             20                  25                  30

Val Lys Thr Leu Gly Ser Lys Arg Cys Lys Trp Cys Cys His Cys Phe
         35                  40                  45

Pro Cys Cys Arg Gly Ser Gly Lys Ser Asn Val Ala Trp Gly Asp
     50                  55                  60

Tyr Asp Asp Ser Ala Phe Met Asp Pro Arg Tyr His Val His Gly Glu
 65                  70                  75                  80

Asp Leu Asp Lys Leu His Arg Ala Ala Trp Trp Gly Lys Val Pro Arg
                 85                  90                  95

Lys Asp Leu Ile Val Met Leu Arg Asp Thr Asp Val Asn Lys Arg Asp
            100                 105                 110

Lys Gln Lys Arg Thr Ala Leu His Leu Ala Ser Ala Asn Gly Asn Ser
        115                 120                 125

Glu Val Val Lys Leu Val Leu Asp Arg Arg Cys Gln Leu Asn Val Leu
    130                 135                 140

Asp Asn Lys Lys Arg Thr Ala Leu Thr Lys Ala Val Gln Cys Gln Glu
145                 150                 155                 160

Asp Glu Cys Ala Leu Met Leu Leu Glu His Gly Thr Asp Pro Asn Ile
                165                 170                 175

Pro Asp Glu Tyr Gly Asn Thr Thr Leu His Tyr Ala Val Tyr Asn Glu
            180                 185                 190

Asp Lys Leu Met Ala Lys Ala Leu Leu Leu Tyr Gly Ala Asp Ile Glu
        195                 200                 205

Ser Lys Asn Lys His Gly Leu Thr Pro Leu Leu Leu Gly Ile His Glu
    210                 215                 220

Gln Lys Gln Gln Val Val Lys Phe Leu Ile Lys Lys Ala Asn Leu
225                 230                 235                 240

Asn Ala Leu Asp Arg Tyr Gly Arg Thr Ala Leu Ile Leu Ala Val Cys
                245                 250                 255

Cys Gly Ser Ala Ser Ile Val Ser Pro Leu Leu Glu Gln Asn Val Asp
            260                 265                 270
```

```
Val Ser Ser Gln Asp Leu Glu Arg Arg Pro Glu Ser Met Leu Phe Leu
        275                 280                 285

Val Ile Ile Met
        290
```

COMPOSITIONS AND METHODS FOR THE TREATMENT AND DIAGNOSIS OF BREAST CANCER

CROSS REFERENCE TO RELATED APPLICATIONS

This application is a continuation-in-part of U.S. patent application Ser. No. 09/289,198, filed Apr. 9, 1999, which is a continuation-in-part of U.S. patent application Ser. No. 09/062,451, filed Apr. 17, 1998 now U.S. Pat. No. 6,344,550, which is a continuation in part of U.S. patent application Ser. No. 08/991,789, filed Dec. 11, 1997 now U.S. Pat. No. 6,225,054, which is a continuation-in-part of U.S. patent application Ser. No. 08/838,762, filed Apr. 9, 1997 now abandoned, which was filed as International Patent Application No. PCT/US97/00485, filed Jan. 10, 1997, and is a continuation-in-part of U.S. patent application Ser. No. 08/700,014, filed Aug. 20, 1996 now abandoned, which is a continuation-in-part of U.S. patent application Ser. No. 08/585,392, filed Jan. 11, 1996 now abandoned.

TECHNICAL FIELD

The present invention relates generally to the detection and therapy of breast cancer. The invention is more specifically related to nucleotide sequences that are preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated polynucleotides are provided, comprising (a) a nucleotide sequence preferentially expressed in breast cancer tissue, relative to normal tissue; (b) a variant of such a sequence, as defined below; or (c) a nucleotide sequence encoding an epitope of a polypeptide encoded by at least one of the above sequences. In one embodiment, the isolated polynucleotide comprises a human endogenous retroviral sequence recited in SEQ ID NO:1. In other embodiments, the isolated polynucleotide comprises a sequence recited in any one of SEQ ID NO: 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314.

In related embodiments, the isolated polynucleotide encodes an epitope of a polypeptide, wherein the polypeptide is encoded by a nucleotide sequence that: (a) hybridizes to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314 under stringent conditions; and (b) is at least 80% identical to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314.

In another embodiment, the present invention provides an isolated polynucleotide encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions, deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a polynucleotide as described above are also provided.

In related aspects, the present invention provides recombinant expression vectors comprising a polynucleotide as described above and host cells transformed or transfected with such expression vectors.

In further aspects, polypeptides comprising an amino acid sequence encoded by a polynucleotide as described above, and monoclonal antibodies that bind to such polypeptides are provided. In certain embodiments, the inventive polypeptides comprise an amino acid sequence selected from the group consisting of SEQ ID NO: 299, 300, 304–306, 308 and 315, and variants thereof as defined below.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and a detection reagent.

Diagnostic kits are also provided that comprise a first polymerase chain reaction primer and a second polymerase chain reaction primer, at least one of the primers being specific for a polynucleotide described herein. In one embodiment, at least one of the primers comprises at least about 10 contiguous nucleotides of a polynucleotide as described above, or a polynucleotide encoding a polypeptide encoded by a sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289 and 290.

Within another related aspect, the diagnostic kit comprises at least one oligonucleotide probe, the probe being specific for a polynucleotide described herein. In one embodiment, the probe comprises at least about 15 contiguous nucleotides of a polynucleotide as described above, or a polynucleotide selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immune response enhancer or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and sequences that hybridize thereto under stringent conditions.

In related, aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 5A and 5B show the sequencing strategy, genomic organization and predicted open reading frame for the retroviral element containing B18Ag1 (SEQ ID NO: 1).

FIG. 6 shows the nucleotide sequence of the representative breast tumor-specific cDNA B18Ag1 (SEQ ID NO: 11).

FIG. 7 shows the nucleotide sequence of the representative breast tumor-specific cDNA B17Ag1 (SEQ ID NO: 12).

FIG. 8 shows the nucleotide sequence of the representative breast tumor-specific cDNA B17Ag2 (SEQ ID NO: 13).

FIG. 9 shows the nucleotide sequence of the representative breast tumor-specific cDNA B13Ag2a (SEQ ID NO: 14).

FIG. 10 shows the nucleotide sequence of the representative breast tumor-specific cDNA B13Ag1b (SEQ ID NO: 15).

FIG. 11 shows the nucleotide sequence of the representative breast tumor-specific cDNA B13Ag1a (SEQ ID NO: 16).

FIG. 12 shows the nucleotide sequence of the representative breast tumor-specific cDNA B11Ag1 (SEQ ID NO: 17).

FIG. 13 shows the nucleotide sequence of the representative breast tumor-specific cDNA B3CA3c (SEQ ID NO: 18).

FIG. 14 shows the nucleotide sequence of the representative breast tumor-specific cDNA B9CG1 (SEQ ID NO: 19).

FIG. 15 shows the nucleotide sequence of the representative breast tumor-specific cDNA B9CG3 (SEQ ID NO: 20).

FIG. 16 shows the nucleotide sequence of the representative breast tumor-specific cDNA B2CA2 (SEQ ID NO: 21).

FIG. 17 shows the nucleotide sequence of the representative breast tumor-specific cDNA B3CA1 (SEQ ID NO: 22).

FIG. 18 shows the nucleotide sequence of the representative breast tumor-specific cDNA B3CA2 (SEQ ID NO: 23).

FIG. 19 shows the nucleotide sequence of the representative breast tumor-specific cDNA B3CA3 (SEQ ID NO: 24).

FIG. 20 shows the nucleotide sequence of the representative breast tumor-specific cDNA B4CA1.

DETAILED DESCRIPTION OF THE INVENTION

Figure 1:
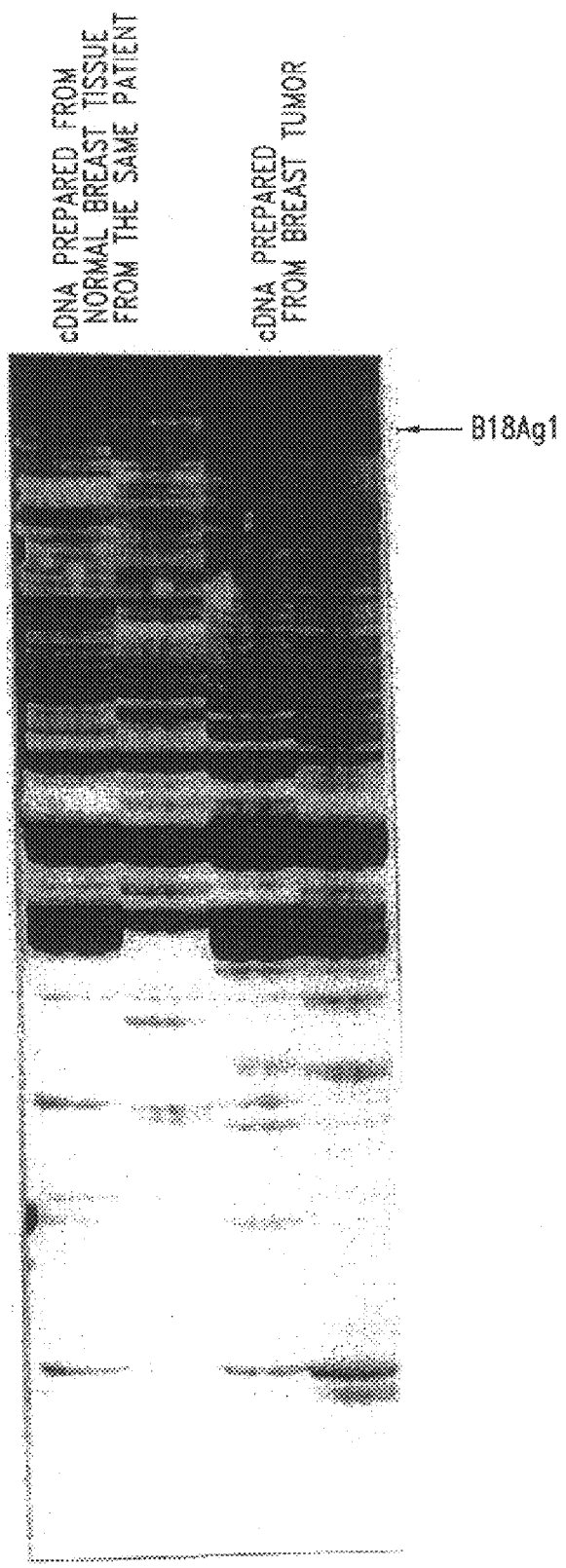
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, polynucleotides and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Polynucleotides of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO:1). Also within the scope of the present invention are polypeptides encoded by other sequences within the retroviral genome containing B18Ag1 (SEQ ID NO: 141). Such sequences include, but are not limited to, the sequences recited in SEQ ID NO:3-SEQ ID NO: 10. B18Ag1 has homology to the gag p30 gene of the endogenous human retroviral element S71, as described in Werner et al., Virology 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314.

As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, *Antibodies: A Laboratory Manual*, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5× SSC, 0.5% SDS, 1.0 mM EDTA (pH 8.0); hybridizing at 50° C. –65° C., 5× SSC, overnight or, in the event of cross-species homology, at 45° C. with 0.5× SSC; followed by washing twice at 65° C. for 20 minutes with each of 2×, 0.5× and 0.2× SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology vol.* 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical. Taxonomy*, Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over, a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity. In general, polynucleotides encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Polynucleotides encoding all or a portion of the breast tumor-specific polypeptides disclosed herein may be amplified from cDNA prepared as described above using the random primers shown in SEQ ID NO.:87–125.

Alternatively, a polynucleotide encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO:1, and may be purchased or synthesized. One suitable primer pair for amplification from breast tumor cDNA is (5'ATG GCT ATT TTC GGG GGC TGA CA) (SEQ ID NO:126) and (5° CCG GTA TCT CCT CGT GGG TAT T) (SEQ ID NO:127). An amplified portion of B18Ag1 may then be used to isolate the full length gene from a human genomic DNA library or from a breast tumor cDNA library, using well known techniques, such as those described in Sambrook et al., *Molecular Cloning: A Laboratory Manual*, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO: 11–86, 142–298, 301–303, 307, 313 and 314.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli,* yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146 (1963). Equipment for automated synthesis of polypeptides is commercially available from suppliers such as Perkin Elmer/Applied BioSystems Division, Foster City, Calif., and may be operated according to the manufacturer's instructions.

In specific embodiments, polypeptides of the present invention encompass amino acid sequences encoded by a polynucleotide having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314, and variants of such polypeptides. Polypeptides within the scope of the present invention also include polypeptides (and epitopes thereof) encoded by DNA sequences that hybridize to a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313 and 314 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6× SSC, 0.2% SDS; hybridizing at 65° C, 6× SSC, 0.2% SDS overnight; followed by two washes of 30 minutes each in 1× SSC, 0.1% SDS at 65° C. and two washes of 30 minutes each in 0.2× SSC, 0.1% SDS at 65° C. Polynucleotides according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, *Antibodies: A Laboratory Manual, Cold Spring Harbor Laboratory,* 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 $\mu$g, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 1 $\mu$g. Such tests can typically be performed with a very small amount of biological sample.

The presence or absence of breast cancer in a patient may also be determined by evaluating the level of mRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify sequences from cDNA prepared from RNA that is isolated from one of the above biological samples. Sequence-specific primers for use in such amplification may be designed based on the sequences provided in any one of SEQ ID NO: 1, 11–86, 142–298 301–303, 307, 313 and 314, and may be purchased or synthesized. In the case of B18Ag1, as noted herein, one suitable primer pair is B18Ag1-2 (5'ATG GCT ATT TTC GGG GGC TGA CA) (SEQ ID NO:126) and B18Ag1-3 (5° CCG GTA TCT CCT CGT GGG TAT T) (SEQ ID NO: 127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of cDNA spanning two orders of magnitude. A two-fold or greater increase in expression in several dilutions of the tumor sample as compared to the same dilution of the non-tumor sample is considered positive.

As used herein, the term "primer/probe specific for a polynucleotide" means an oligonucleotide sequence that has at least about 80% identity, preferably at least about 90% and more preferably at least about 95%, identity to the polynucleotide in question, or an oligonucleotide sequence that is anti-sense to a sequence that has at least about 80% identity, preferably at least about 90% and more preferably at least about 95%, identity to the polynucleotide in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a polynucleotide that encodes one of the polypeptides disclosed herein or that is anti-sense to a sequence that encodes one of the polypeptides disclosed herein. Preferably, oligonucleotide probes for use in the inventive diagnostic methods comprise at least about 15 contiguous oligonucleotides of a polynucleotide that encodes one of the polypeptides disclosed herein or that is anti-sense to a sequence that encodes one of the polypeptides disclosed herein. Techniques for both PCR based assays and in situ hybridization assays are well known in the art.

Conventional RT-PCR protocols using agarose and ethidium bromide staining, while important in defining gene specificity, do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 $\mu$g to 100 $\mu$g, preferably from about 10 $\mu$g to 50 $\mu$g in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or polynucleotides) are preferably incorporated into pharmaceutical compositions or vaccines. Pharmaceutical compositions comprise one or more such compounds and a physiologically acceptable carrier. Vaccines may comprise one or more such compounds and an immune response enhancer, such as an adjuvant or a liposome (into which the compound is incorporated). Pharmaceutical compositions and vaccines may additionally contain a delivery system, such as biodegradable microspheres as disclosed, for example, in U.S. Pat. Nos. 4,897,268 and 5,075,109. Pharmaceutical compositions and vaccines within the scope of the present invention may also contain other compounds, including one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993), and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The above pharmaceutical compositions and vaccines may be used, for example, for the therapy of breast cancer in a patient. As used herein, a "patient" refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. In a preferred embodiment, the compounds are administered either prior to or following surgical removal of primary tumors and/or treatment by administration of radiotherapy and conventional chemotherapeutic drugs. To prevent or slow the development of breast cancer, a pharmaceutical composition or vaccine comprising one or more polypeptides as described herein may be administered to a patient. Alternatively, naked DNA or plasmid or viral vector encoding the polypeptide may be administered. For treating a patient with breast cancer, the pharmaceutical composition or vaccine may comprise one or more polypeptides, antibodies or polynucleotides complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. *Ibid*).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.*, 22(3), 213, 1996).

In another embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," *Immunological Reviews*, 157:177, 1997).

Additionally vectors expressing the disclosed polynucleotides may be introduced into stem cells taken from the patient and clonally propagated in vitro for autologous transplant back into the same patient. In one embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

The following Examples are offered by way of illustration and not by way of limitation.

EXAMPLES

Example 1

Preparation of Breast Tumor-Specific cDNAs Using Differential Display RT-PCR This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO:130) anchored 3' primer. Differential display PCR was then executed using a randomly chosen primer (CTTCAACCTC) (SEQ ID NO: 103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., Virology 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
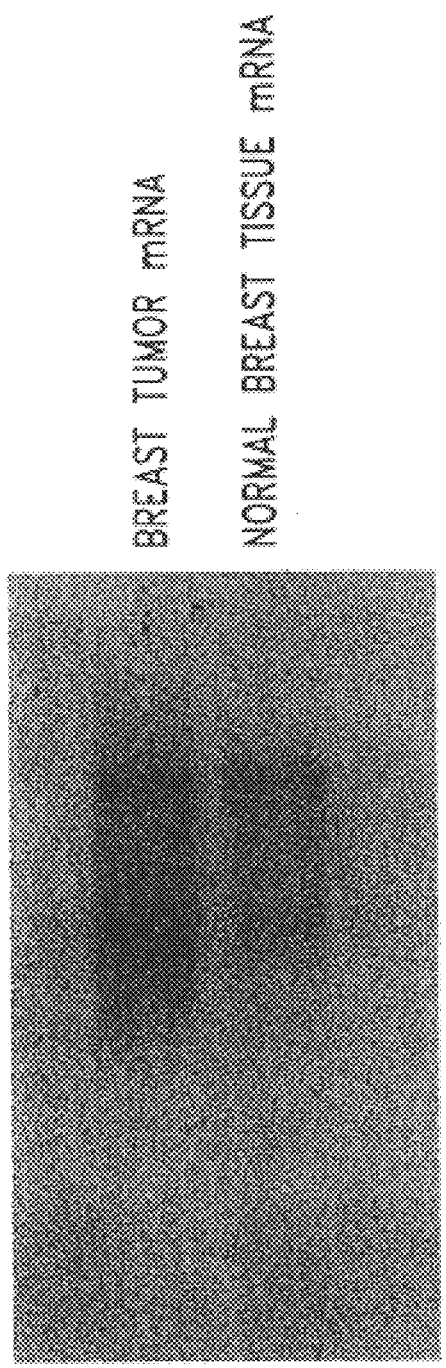
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO:128) and B18Ag1-4 (CCG GAG GAG GAA GCT AGA GGA ATA) (SEQ ID NO: 129) at a 3.5 mM magnesium concentration and a pH of 8.5, and B18Ag1-2 (ATG GCT ATT TTC GGG GCC TGA CA) (SEQ ID NO:126) and B18Ag1-3 (CCG GTA TCT CCT CGT GGG TAT T) (SEQ ID NO:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
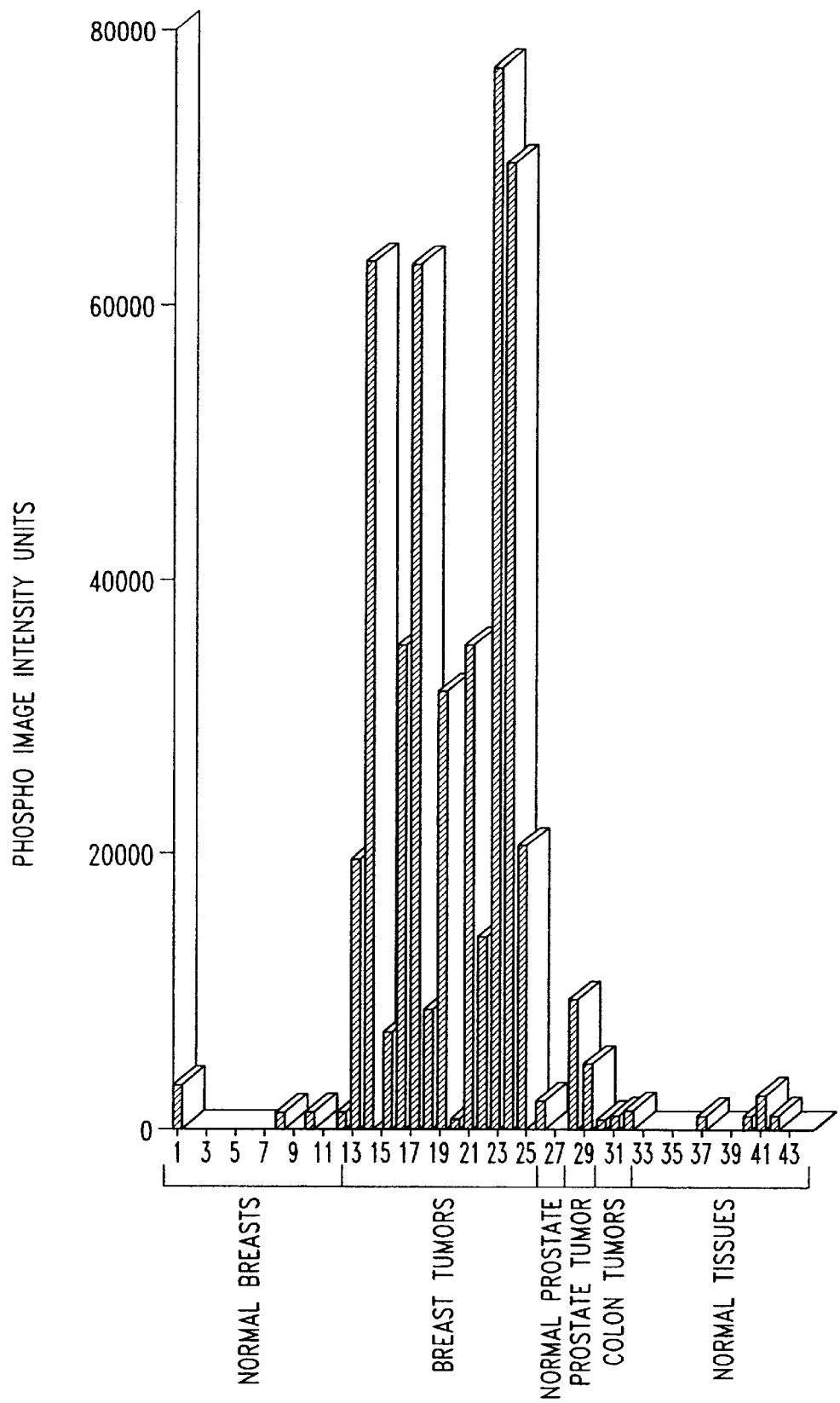
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
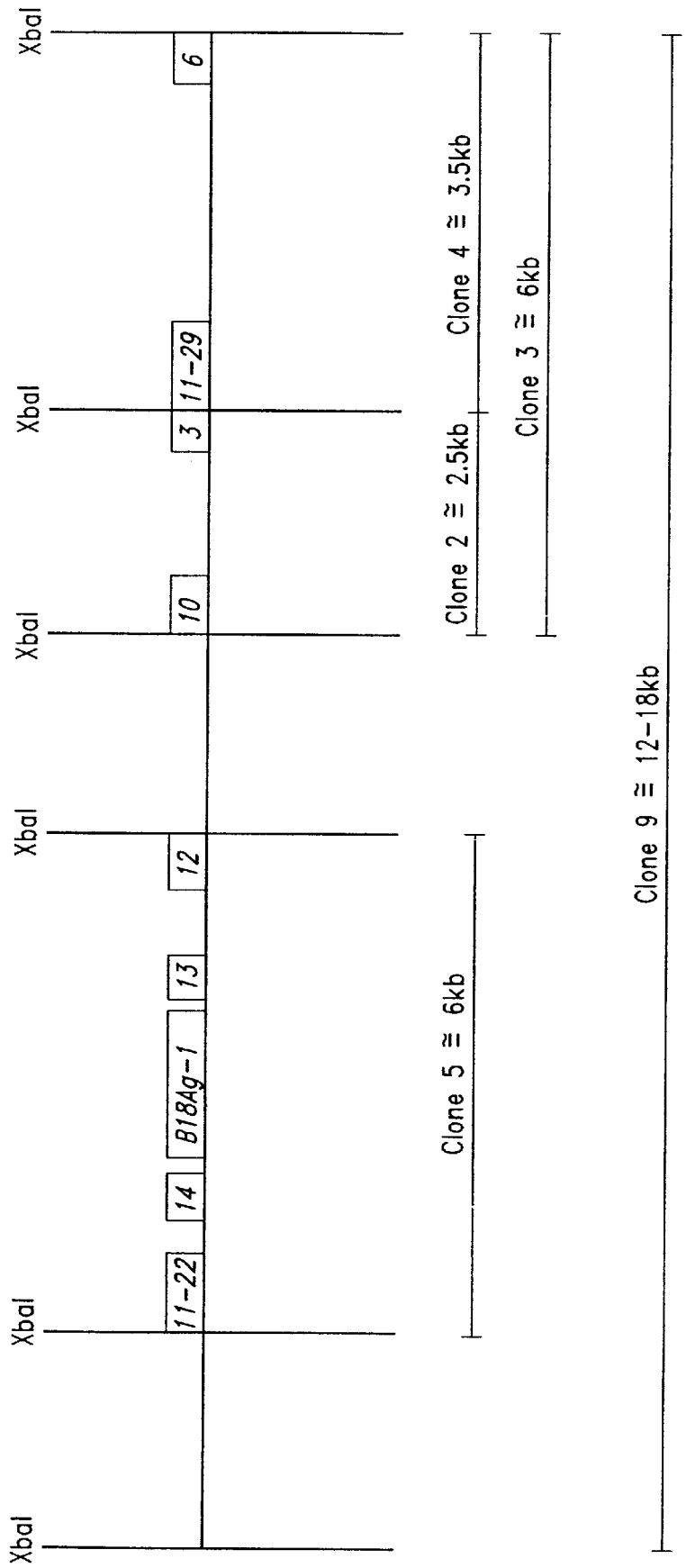
FIG. 4 is a genomic clone map showing the location of additional retroviral sequences obtained from ends of XbaI restriction digests (provided in SEQ ID NO:3–SEQ ID NO:10) relative to B18Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3-SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11–22.

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO: 1 as a probe, a longer cDNA was obtained (SEQ ID NO:227) which contains minor nucleotide differences (less than 1%) compared to the genomic sequence shown in SEQ ID NO: 141

B. Preparation of cDNA Molecules Encoding Other Breast Tumor-Specific Polypeptides Normal RNA and tumor RNA was prepared and mRNA was isolated and converted into cDNA using a $(dT)_{12}AG$ anchored 3' primer, as described above. Differential display PCR was then executed using the randomly chosen primers of SEQ ID NO: 87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO: 11–SEQ ID NO:86. Of the 79 sequences isolated, 67 were found to be novel (SEQ ID NO: 11–26 and 28–77) (see also FIGS. 6–20).

An extended DNA sequence (SEQ ID NO: 290) for the antigen B15Ag1 (originally identified partial sequence provided in SEQ ID NO: 27) was obtained in further studies. Comparison of the sequence of SEQ ID NO: 290 with those in the gene bank as described above, revealed homology to the known human β-A activin gene. Further studies led to the isolation of the full-length cDNA sequence for the antigen B21GT2 (originally identified partial cDNA sequence provided in SEQ ID NO: 56). The full-length sequence is provided in SEQ ID NO: 307.

Subsequent studies identified an additional 146 sequences (SEQ ID NOS:142–289), of which 115 appeared to be novel (SEQ ID NOS:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

In further studies, several different splice forms of the antigen B11Ag1 (also referred to as B305D) were isolated, with each of the various splice forms containing slightly different versions of the B11Ag1 coding frame. Splice junction sequences define individual exons which, in various patterns and arrangements, make up the various splice forms. Primers were designed to examine the expression pattern of each of the exons using RT-PCR as described below. Each exon was found to show the same expression pattern as the original B11Ag1 clone, with expression being breast tumor-, normal prostate- and normal testis-specific. The determined cDNA sequences for the isolated protein coding exons are provided in SEQ ID NO: 292–298, respectively. The predicted amino acid sequences corresponding to the sequences of SEQ ID NO: 292 and 298 are provided in SEQ ID NO: 299 and 300. Additional studies using rapid amplification of cDNA ends (RACE), a 5' specific primer to one of the splice forms of B11Ag1 provided above and a breast adenocarcinoma, led to the isolation of three additional, related, splice forms referred to as isoforms B11C-15, B11C-8 and B11C-9,16. The determined cDNA sequences for these isoforms are provided in SEQ ID NO: 301–303, with the corresponding predicted amino acid sequences being provided in SEQ ID NO: 304–306.

In subsequent studies on B305D isoform A (cDNA sequence provided in SEQ ID NO: 292), the cDNA sequence (provided in SEQ ID NO: 313) was found to contain an additional guanine residue at position 884, leading to a frameshift in the open reading frame. The determined DNA sequence of this ORF is provided in SEQ ID NO: 314. This frameshift generates a protein sequence (provided in SEQ ID NO: 315) of 293 amino acids that contains the C-terminal domain common to the other isoforms of B305D but that differs in the N-terminal region.

Example 2

Preparation of B18AG1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B18AG1 DNA from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+RNA, 200 pmol of the primer $(T)_{12}AG$ (i.e., TTT TTT TTT TTT AG) (SEQ ID NO: 130), IX first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 μl. After first strand synthesis, the cDNA is diluted approximately 25 fold and 1 μl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-Cell and T-Cell Epitopes of B18AG1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med* 164:1779–84 (1986) or Spouge et al., *J. Immunol.* 138:204–12 (1987). Additional Class II MHC (antibody or B-cell) epitopes can be predicted using programs such as AMPHI (e.g., Margalit et al., *J. Immunol.* 138:2213 (1987)) or the methods of Rothbard and Taylor (e.g., *EMBO J.* 7:93(1988)).

Once peptides (15–20 amino acids long) are identified using these techniques, individual peptides can be synthesized using automated peptide synthesis equipment (available from manufacturers such as Perkin Elmer/Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

Figure 21A:
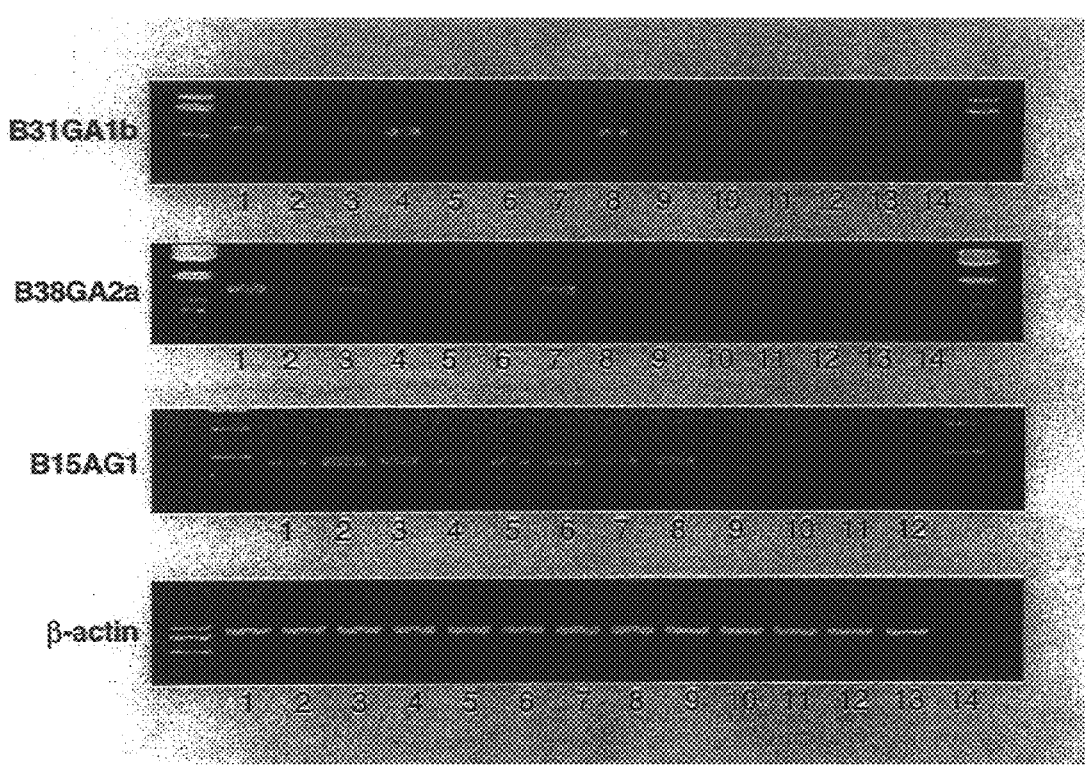
FIG. 21A depicts RT-PCR analysis of breast tumor genes in breast tumor tissues (lanes 1–8) and normal breast tissues (lanes 9–13) and $H_2O$ (lane 14).
Figure 21B:
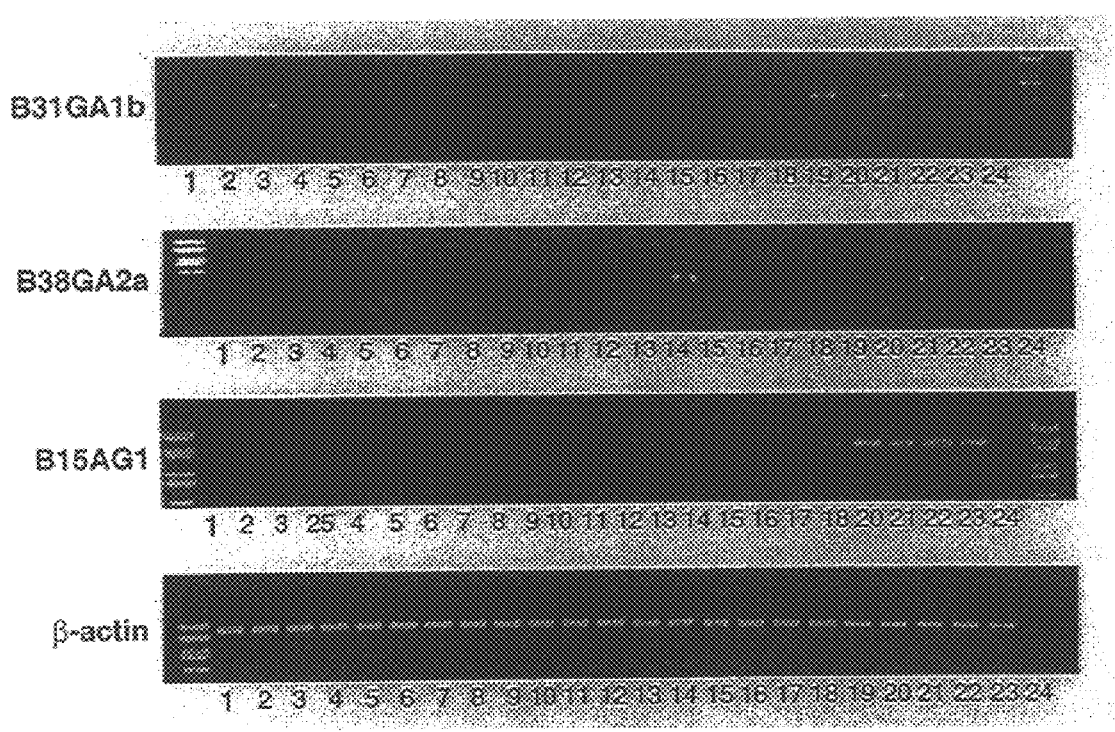
FIG. 21B depicts RT-PCR analysis of breast tumor genes in prostate tumors (lane 1, 2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), $H_2O$ (lane 24), and colon tumor (lane 25).
Figure 22:
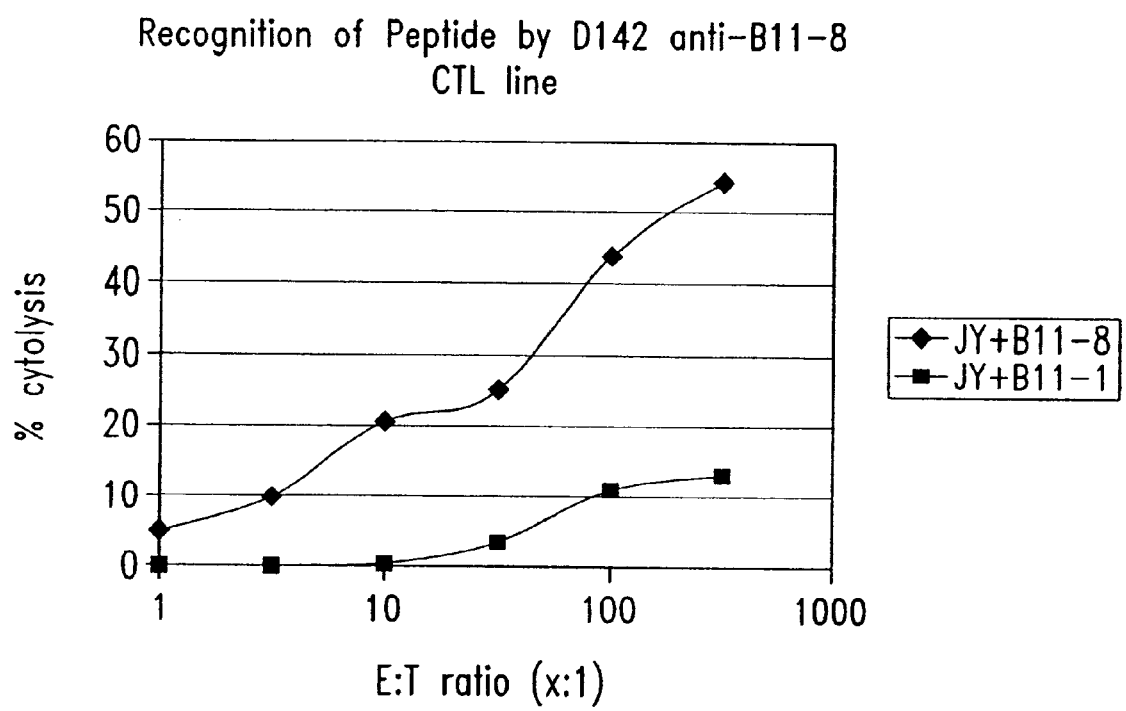
FIG. 22 shows the recognition of a B11Ag1 peptide (referred to as B11-8) by an anti-B11-8 CTL line.
Figure 23:
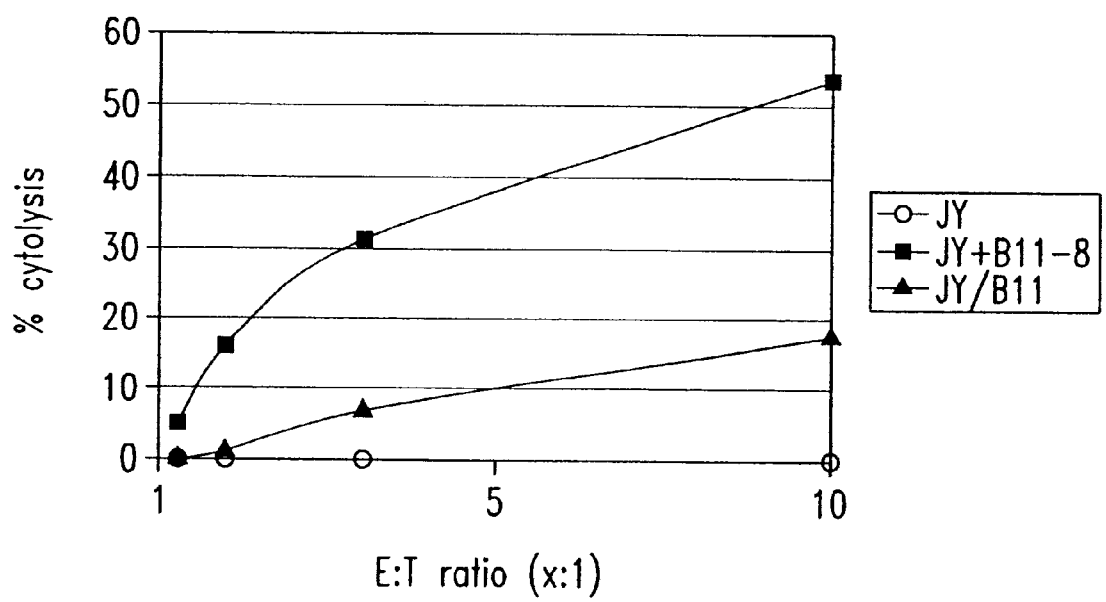
FIG. 23 shows the recognition of a cell line transduced with the antigen B11Ag1 by the B11-8 specific clone A1.
Figure 24:
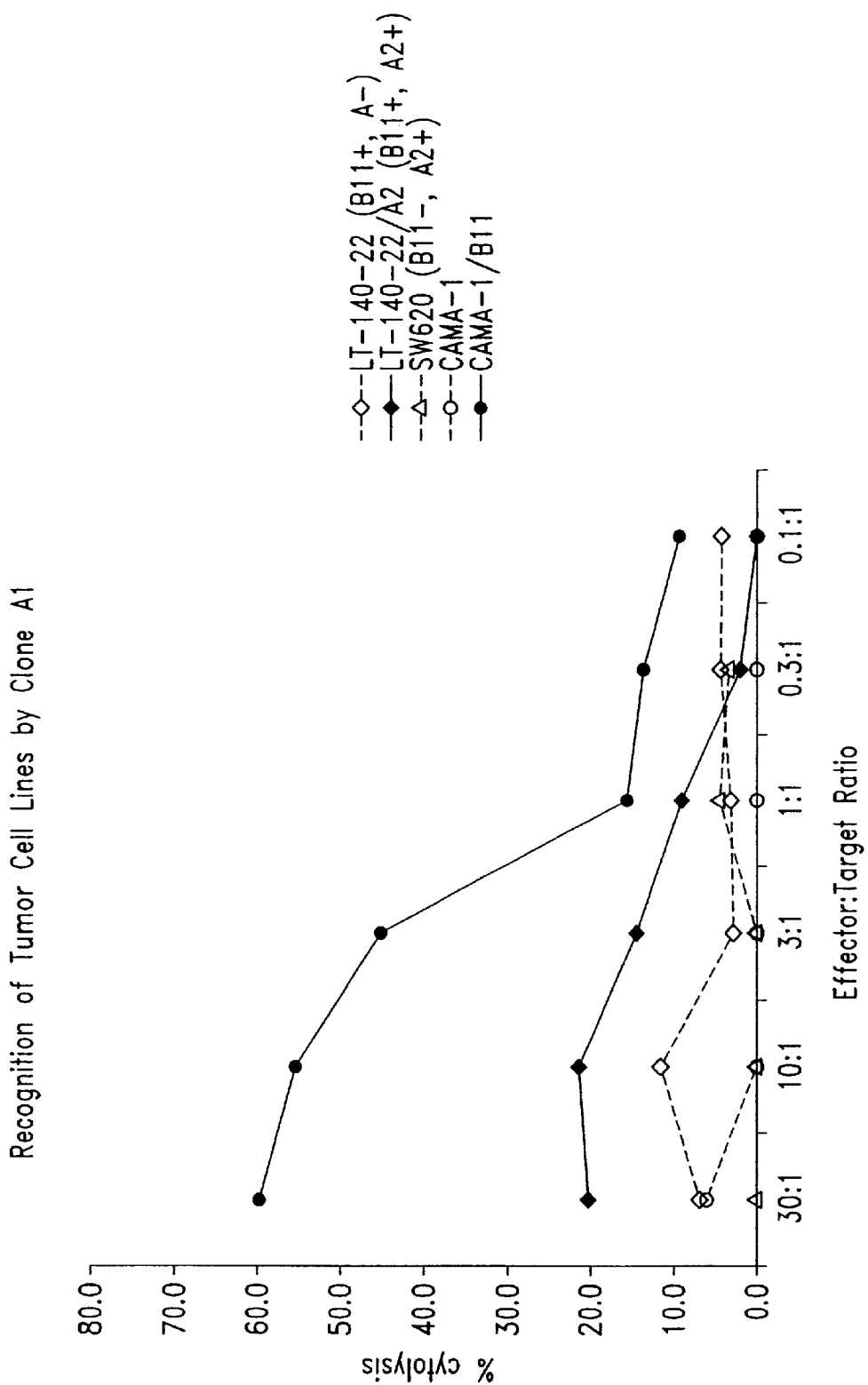
FIG. 24 shows recognition of a lung adenocarcinoma line (LT-140-22) and a breast adenocarcinoma line (CAMA-1) by the B11-8 specific clone A1.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al., *Immunogenetics* 41:178–228 (1995)). Following synthesis such peptides can be tested for their ability to bind to class I MHC using standard binding assays (e.g., Sette et al., *J. Immunol* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995); Visseren et al., *J. Immunol.* 154:3991–98 (1995); Kawakami et al., *J. Immunol.* 154:3961–68 (1995); and Kast et al., *J. Immunol.* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J. Exp. Med* 173:1007–15 (1991).

A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)

SSGGRTFDDFHRYLLVGI

QGAAQKPINLSKXIEVVQGHDE

SPGVFLEHLQEAYRIYTPFDLSA

Predicted HLA A2.1 Motifs (T-cell epitopes) (SEQ ID NOS.: 134–140)

YLLVGIQGA

GAAQKPINL

NLSKXIEVV

EVVQGHDES

HLQEAYRIY

NLAFVAQAA

FVAQAAPDS

Example 5

Identification of T-Cell Epitopes of B11AG1

This Example illustrates the identification of B11Ag1 (also referred to as B305D) epitopes. Four peptides, referred to as B11-8, B11-1, B11-5 and B11-12 (SEQ ID NO: 309–312, respectfully) were derived from the B11Ag1 gene.

Human CD8 T cells were primed in vitro to the peptide B11-8 using dendritic cells according to the protocol of Van Tsai et al. (*Critical Reviews in Immunology* 18:65–75, 1998). The resulting CD8 T cell cultures were tested for their ability to recognize the B11-8 peptide or a negative control peptide, presented by the B-LCL line, JY. Briefly, T cells were incubated with autologous monocytes in the presence of 10 ug/ml peptide, 10 ng/ml IL-7 and 10 ug/ml IL-2, and assayed for their ability to specifically lyse target cells in a standard 51-Cr release assay. As shown in FIG. 22, the bulk culture line demonstrated strong recognition of the B11-8 peptide with weaker recognition of the peptide B11-1.

A clone from this CTL line was isolated following rapid expansion using the monoclonal antibody OKT3 and human IL-2. As shown in FIG. 23, this clone (referred to as A1), in addition to being able to recognize specific peptide, recognized JY LCL transduced with the B11Ag1 gene. This data demonstrates that B11-8 is a naturally processed epitope of the B11Ag1 gene. In addition these T cells were further found to recognize and lyse, in an HLA-A2 restricted manner, an established tumor cell line naturally expressing B11Ag1 (FIG. 24). The T cells strongly recognize a lung adenocarcinoma (LT-140-22) naturally expressing B11Ag1 transduced with HLA-A2, as well as an A2+ breast carcinoma (CAMA-1) transduced with B11Ag1, but not untransduced lines or another negative tumor line (SW620).

These data clearly demonstrate that these human T cells recognize not only B11-specific peptides but also transduced cells, as well as naturally expressing tumor lines.

CTL lines raised against the antigens B11-5 and B11-12, using the procedures described above, were found to recognize corresponding peptide-coated targets.

Example 6

Characterization of Breast Tumor Genes Discovered By Differential Display PCR The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β -actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO. 157). Table I summarizes the expression level of all the genes tested in normal breast tissue and breast tumors, and also in other tissues.

TABLE I

| | Percentage of Breast Cancer Antigens that are Expressed in Various Tissues | |
|---|---|---|
| Breast Tissues | Over-expressed in Breast Tumors | 84% |
| | Equally Expressed in Normals and Tumor | 16% |

TABLE I-continued

| | Percentage of Breast Cancer Antigens that are Expressed in Various Tissues | |
|---|---|---|
| Other Tissues | Over-expressed in Breast Tumors but not in any Normal Tissues | 9% |
| | Over-expressed in Breast Tumors but Expressed in Some Normal Tissues | 30% |
| | Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising an amino acid sequence of SEQ ID NO: 315.

2. A composition, comprising a polypeptide according to claim 1, and a physiologically acceptable carrier.

3. A composition comprising a polypeptide according to claim 1, and an immune response enhancer.

4. An isolated polypeptide comprising an amino acid sequence encoded by a nucleotide sequence selected from the group consisting of:

(a) SEQ ID NO: 313; and (b) SEQ ID NO: 314.

5. An isolated polypeptide comprising an amino acid sequence encoded by a nucleotide sequence selected from the group consisting of sequences that have at least 80% identity to any one of SEQ ID NO: 313 and 314, wherein the polypeptide is expressed in breast tumor tissue at a level that is at least two times the level of expression in normal breast tissue.

6. A composition comprising a polypeptide according to any one of claims 4 or 5, and a physiologically acceptable carrier.

7. A composition comprising a polypeptide according to any one of claims 4 or 5, and an immune response enhancer.

8. An isolated polypeptide comprising an amino acid sequence encoded by a nucleotide sequence selected from the group consisting of sequences that have at least 90% identity to any one of SEQ ID NO:313 and 314; wherein the polypeptide is expressed in breast tumor tissue at a level that is at least two times the level of expression in normal breast tissue.

* * * * *